(12) United States Patent
Moonlee et al.

(10) Patent No.: US 9,303,088 B2
(45) Date of Patent: Apr. 5, 2016

(54) DETECTING AND TREATING BREAST CANCER RESISTANCE TO EGFR INHIBITORS

(75) Inventors: Sun-Young Moonlee, Busan (KR); Mina J. Bissell, Berkeley, CA (US); Saori Furuta, Emeryville, CA (US); Roland Meier, Geneva (CH); Paraic A. Kenny, Yonkers, NY (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/248,690

(22) Filed: Sep. 29, 2011

(65) Prior Publication Data

US 2012/0094843 A1  Apr. 19, 2012

Related U.S. Application Data

(63) Continuation of application No. PCT/US2010/029497, filed on Mar. 31, 2010.

(60) Provisional application No. 61/165,668, filed on Apr. 1, 2009.

(51) Int. Cl.
*A61K 39/395* (2006.01)
*C07K 16/30* (2006.01)

(52) U.S. Cl.
CPC .................................. *C07K 16/3015* (2013.01)

(58) Field of Classification Search
None
See application file for complete search history.

(56) References Cited

U.S. PATENT DOCUMENTS

2005/0106644 A1  5/2005  Cairns et al.
2008/0113874 A1  5/2008  Bunn et al.

FOREIGN PATENT DOCUMENTS

WO  WO 97/00271  1/1997
WO  WO 2008/104543  9/2008

OTHER PUBLICATIONS

Armstrong et al., "A Phase I Study of Chemically Synthesized Verotoxin (Shiga-like Toxin) Pk-Trisaccharide Receptors Attached to Chromosorb for Preventing Hemolytio-Uremic Syndrome" J. Infectious Diseases 171:1042-1045 (1995).
International Search Report and Written Opinion dated Aug. 11, 2010 for PCT/US2010/029497 filed Mar. 31, 2010.
Corkery et al. "Epidermal growth factor receptor as a potential therapeutic target in triple-negative breast cancer," Annals of Oncology 20: 862-867 (2009), published online Jan. 15, 2009.
Davidson et al., "Epidermal growth factor receptor gene expression in estrogen receptor-positive and negative human breast cancer cell lines," Molecular Endocrinology, 1(3):216-223 (1987).
Lee, Chapters 4 and 5 of "Identification and characterization of novel genes involved in signaling pathways that disrupt phenotypic reversion in a model of human breast cancer cells in 3-D IrECM cultures", University of California, Berkeley, Dissertation for the degree of Doctor of Philosophy, Fall 2007.
Lee et al. "FAM83A confers EGFR-TKI resistance in breast cancer cells and in mice," Journal of Clinical Investigation, 122(9):3211-3220 (2012).

*Primary Examiner* — Michele K Joike
(74) *Attorney, Agent, or Firm* — Knobbe Martens Olson & Bear LLP

(57) ABSTRACT

The application describes therapeutic compositions and methods for treating cancer. For example, therapeutic compositions and methods related to inhibition of FAM83A (family with sequence similarity 83) are provided. The application also describes methods for diagnosing cancer resistance to EGFR inhibitors. For example, a method of diagnosing cancer resistance to EGFR inhibitors by detecting increased FAM83A levels is described.

8 Claims, 21 Drawing Sheets

Phenotypic reversion of T4-2 cells in 3D lrECM culture

Western blot analysis

*FIG. 5A*   3D lrECM culture of vector, full-length or truncated FAM83A overexpressing T4-2 cells
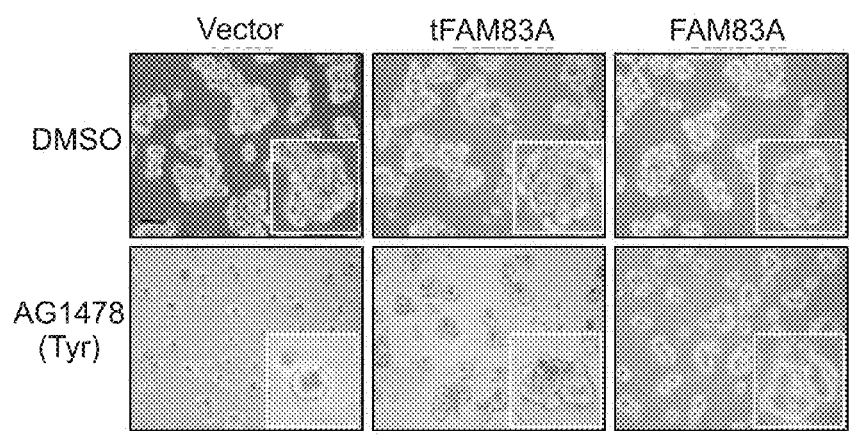
*FIG. 5B*   3D lrECM culture of vector or full-length FAM83A overexpressing T4-2 cells
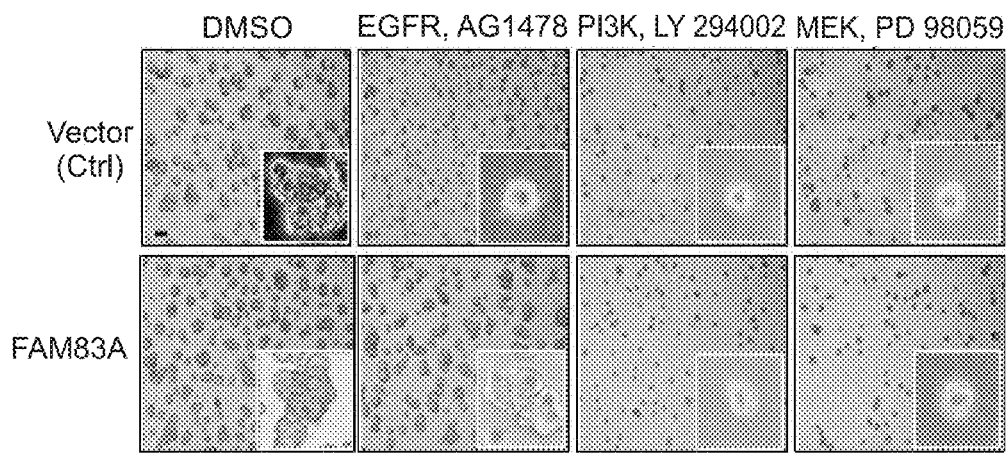

FAM83A RNA expression in T4-2 in 2D and 3D culture
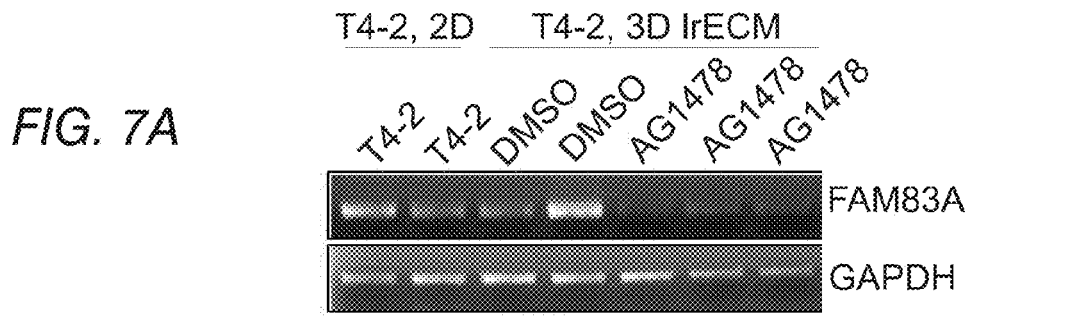
FIG. 7A
FIG. 7B
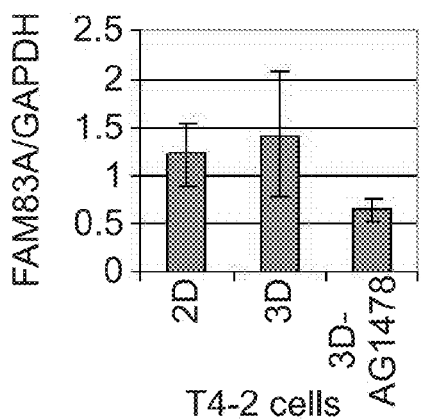
Quantification data of (A)
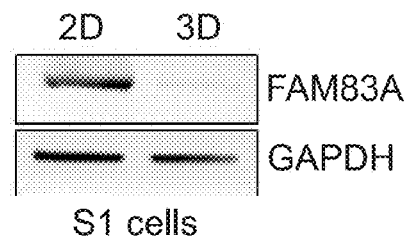
FAM83A RNA expression in S1 in 2D and 3D culture
FIG. 7C
Western blot analysis of FAM83A in S1 and T4-2 cells
FIG. 7D
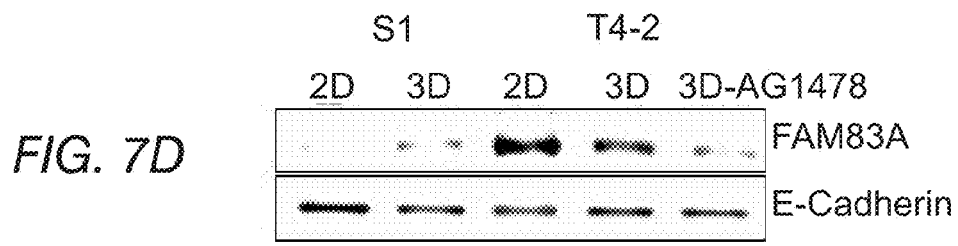

3D lrECM culture of siRNA-treated T4-2 cells mRNA level of FAM83A in siRNA-treated T4-2 cells 3D lrECM culture of siRNA-treated S1 cells mRNA level of FAM83A in siRNA-treated S1 cells Ki67 index of siRNA-treated cells in 3D culture Immunofluorescence of α6 integrin and DAPI of siRNA treated T4-2 cells in 3D culture α6 integrin
DAPI 2D culture, T4-2 cells F-actin staining with phalloidin in siRNA-treated T4-2 cells F-actin staining with phalloidin in siRNA-treated S1 cells Invasion assay of siRNA treated T4-2 cells Invasion assay of vector or FAM83A overexpressing T4-2 cells FIG. 12A   Western blot analysis of vector or FAM83A expressing S1 cells
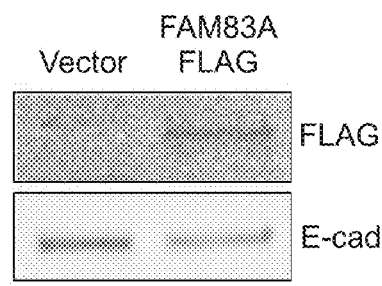
FIG. 12B   3D culture of vector or FAM83A overexpressing S1 cells
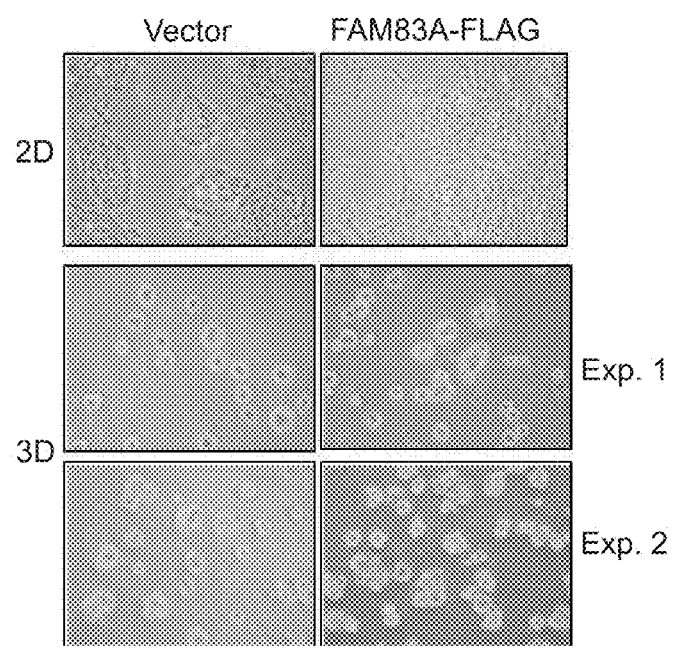
FIG. 12C   Immunofluorescence of α6-integrin in vector of FAM83A overexpressing S1 cells
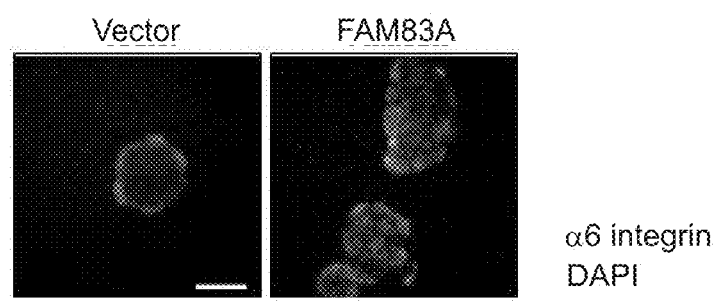
α6 integrin
DAPI

*FIG. 13A*   Western blot analysis of FAM83A
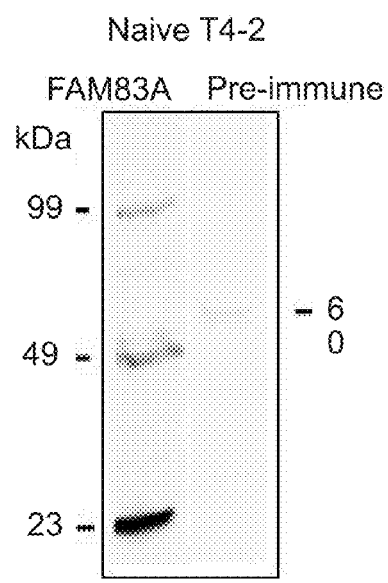
*FIG. 13B*   Schematic presentation of putative FAM83A isoforms
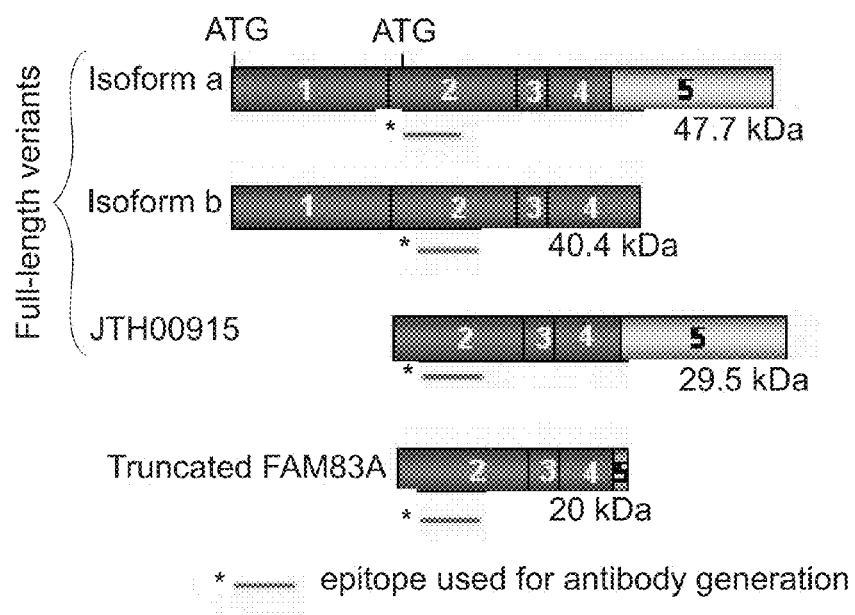

Immunofluorescence staining of FAM83A in siRNA-treated T4-2 cells

Western bolt analysis of FAM83A cultured in (A)

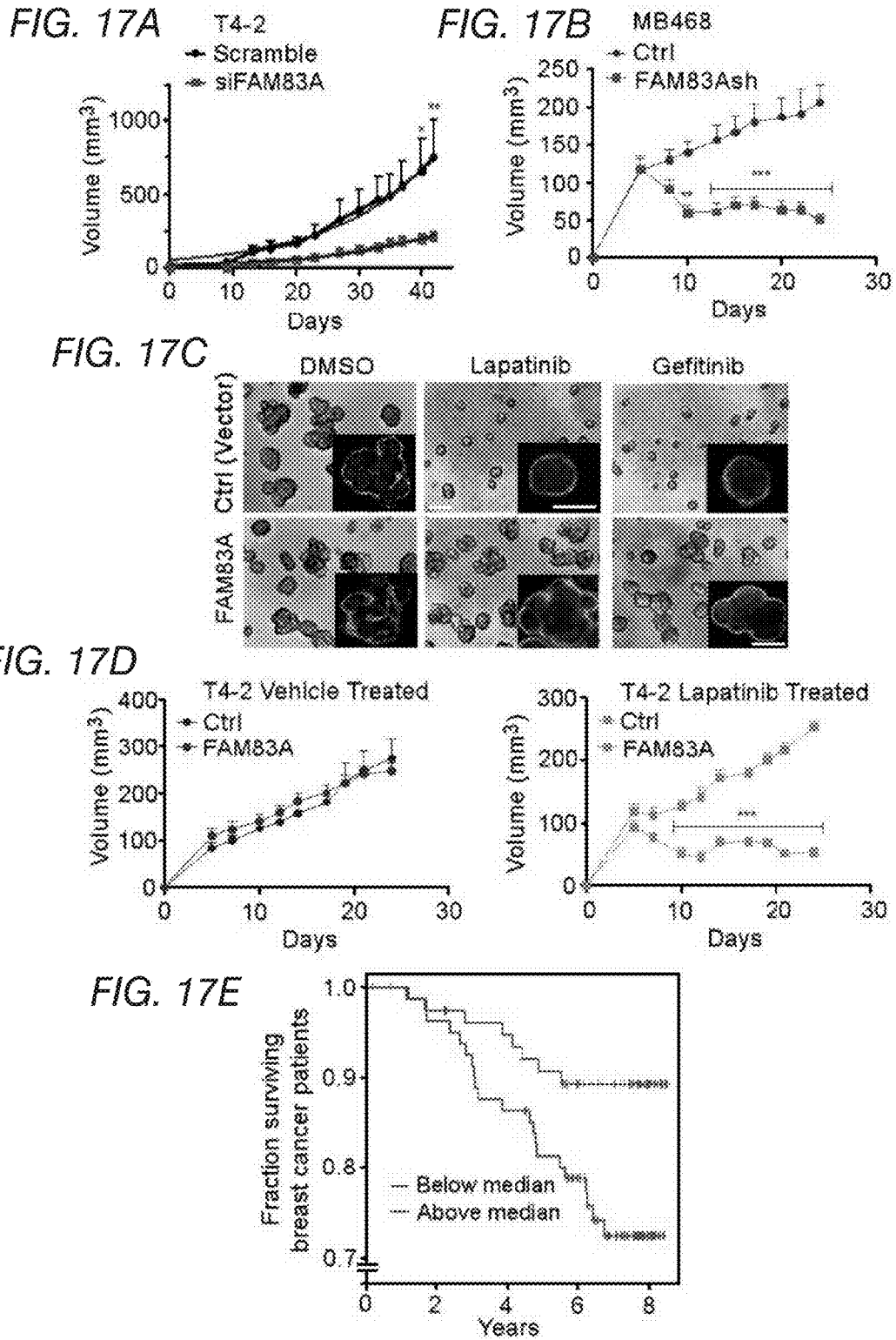

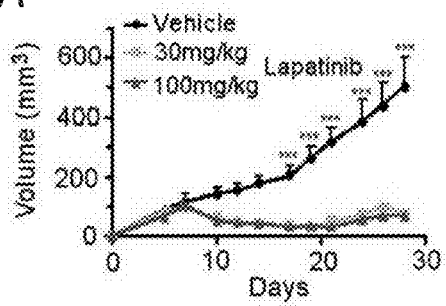
FIG. 18A
FIG. 18B
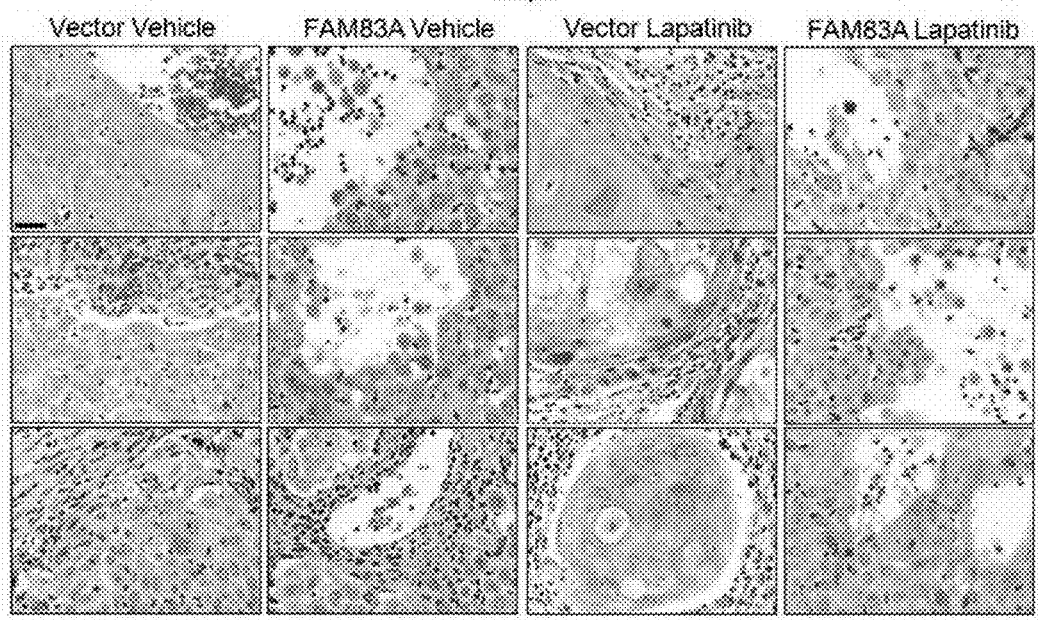

DETECTING AND TREATING BREAST CANCER RESISTANCE TO EGFR INHIBITORS

CROSS-REFERENCE TO RELATED APPLICATIONS

This application is a continuation of and claims the benefit of priority to copending International Application No. PCT/US2010/029497, filed on Mar. 31, 2010 designating the U.S. and published on Oct. 21, 2010 as WO 2010/120554, which claims the benefit under 35 U.S.C. §119(e) of U.S. Provisional Application No. 61/165,668, filed Apr. 1, 2009, all of which are herein incorporated by reference in their entirety.

STATEMENT REGARDING FEDERALLY SPONSORED R&D

This work was supported by Grant No. CA064786 awarded by the National Institutes of Health and the National Cancer Institute, Grant No. DAMD17-02-1-0441 awarded by the Department of Defense, and by Contract No. DE-AC02-05CH11231 awarded by the Department of Energy. The government has certain rights in the invention.

REFERENCE TO SEQUENCE LISTING, TABLE, OR COMPUTER PROGRAM LISTING

The present application is being filed along with a Sequence Listing in electronic format. The Sequence Listing is provided as a file entitled LBNL041C1.TXT, created Sep. 29, 2011, which is 7.83 KB in size. The information in the electronic format of the Sequence Listing is incorporated herein by reference in its entirety.

BACKGROUND OF THE INVENTION

1. Field of the Invention

Therapeutic compositions and methods for treating cancer are provided. In particular, therapeutic compositions and methods related to inhibition of FAM83A (family with sequence similarity 83) are provided. Methods for diagnosing breast cancer resistance to EGFR inhibitors are also provided.

2. Background

A. Breast Cancer

Cancer is a major public health problem throughout the world. In women, breast cancer is the most common malignancy. In year 2006, over 180,000 new cases and 40,000 breast cancer-related deaths have been reported in the United States alone (Jemal et al. 2007). The overall death rate of patients with breast cancer has declined during the past decade due to early detection of the disease by mammographic screening and implementation of adjuvant systemic treatment (Mettlin 1999; Jemal et al. 2007). However, a substantial number of patients acquire resistance to treatment, which is followed by a rapid relapse of the disease (Ranson et al. 2002; Dancey 2004; Hortobagyi 2004; Nahta et al. 2006). Although recent advancement in breast cancer research has contributed to our understanding of the molecular mechanisms underlying the disease, delineating how breast cancer cells become refractory to treatment and identifying proper therapeutic targets still remain a challenge.

Breast cancer is a diagnostically heterogeneous disease with different types and has been categorized into ~18 histological types and ~5 molecular subtypes (Perou et al. 2000). Breast cancer research has progressed our understanding of the molecular mechanisms of tumorigenesis and many therapeutic strategies have been developed. Some examples of therapies include inhibitors of receptor tyrosine kinases such as lapatinib (Rusnak et al. 2001) and humanized blocking antibodies against oncogenic receptors such as Trastuzumab (Herceptin) to block the signals that would otherwise instruct the cells to become disorganized within the tissue and grow out of control.

SUMMARY OF THE INVENTION

Provided herein are methods of detecting and treating breast cancer resistance to EGFR tyrosine kinase inhibitors.

One embodiment is a method of diagnosing breast cancer resistance to an EGFR tyrosine kinase inhibitor including obtaining a biological sample comprising mammary cells from a subject and detecting FAM83A levels in the mammary cells, wherein increased FAM83A levels relative to control indicate resistance to an EGFR tyrosine kinase inhibitor.

In one aspect of the preceding embodiment, detecting FAM83A levels comprises detecting FAM83A RNA levels. In another aspect, FAM83A protein levels are detected. In the same aspect, detecting FAM83A levels comprises detecting FAM83A protein levels using a polyclonal antibody against FAM83A. Further in the same aspect, the polyclonal antibody is raised against a peptide having an amino acid sequence of SEQ ID NO:6. In another aspect, the EGFR tyrosine kinase inhibitor is AG1478, gefitinib, or lapatinib.

One embodiment is a method of identifying a therapeutic compound for treating breast cancer cells resistant to an EGFR tyrosine kinase inhibitor including identifying a gene that confers resistance to an EGFR tyrosine kinase inhibitor, administering to the breast cancer cells a compound that inhibits expression of the gene or the activity of its encoded polypeptide, and detecting reversion of the breast cancer cells to a phenotypically normal structure in response to administration of the compound.

In one aspect of the preceding embodiment, the breast cancer cells are HMT3522 T4-2 cells. In another aspect, the compound is administered to the breast cancer cells grown in a three-dimensional culture. In the same aspect, the three-dimensional culture comprises growth factor reduced laminin rich extracellular matrix. In a further aspect, the phenotypically normal structure is acinar. In yet another aspect, the compound comprises a siRNA oligonucleotide.

One embodiment is a method of identifying a gene that confers resistance to an EGFR tyrosine inhibitor in breast cancer cells including expressing a cDNA library comprising at least one cDNA in breast cancer cells, administering the EGFR tyrosine kinase inhibitor to the breast cancer cells, detecting reversion of the breast cancer cells to a phenotypically normal structure in response to the EGFR tyrosine kinase inhibitor, and identifying cDNA from the breast cancer cells that do not undergo the reversion.

In one aspect of the preceding embodiment, the cDNA library is expressed in breast cancer cells by retroviral transduction. In another aspect, the breast cancer cells are grown in two-dimensional culture. In a further aspect, the breast cancer cells are grown in two-dimensional culture. In an additional aspect, the breast cancer cells are HMT3522 T4-2 cells.

In yet another aspect, the EGFR tyrosine kinase inhibitor is administered to the breast cancer cells grown in a three-dimensional culture. In the same aspect, the three-dimensional culture includes growth factor reduced laminin rich extracellular matrix. In still a further aspect, the phenotypically normal structure is acinar. In another aspect, the phenotypically normal structure is polarized. In an additional aspect, the EGFR tyrosine kinase inhibitor is AG1478, gefitinib, or lapatinib. In a further aspect, the cDNA is identified by nucleotide sequencing.

BRIEF DESCRIPTION OF THE DRAWINGS

FIG. 5A is a panel of microscopic fields showing T4-2 cells overexpressing a control vector, truncated FAM83A (tFAM83A), or full-length FAM83A cultured in 3D 1rECM in the presence of DMSO or AG1478. FIG. 5B is a panel of microscopic visual fields showing T4-2 cells overexpressing a control vector or full-length FAM83A cultured in 3D 1rECM in the presence of DMSO, AG1478, LY294002, or PD98059.

FIG. 7A is a RT-PCR analysis of FAM83A RNA expression in T4-2 cells grown in 2D or 3D cultures. FIG. 7B is a bar graph measurement of normalized FAM83A levels from FIG. 7A. FIG. 7C is a RT-PCR analysis of FAM83A RNA expression in S1 cells grown in 2D or 3D cultures. FIG. 7D is a western blot showing FAM83A levels in S1 and T4-2 cells grown in 2D or 3D cultures in the absence or presence of AG1478.

FIG. 12A is a western blot showing FAM83A-FLAG levels of vector or FAM83A overexpressing S1 cells. FIG. 12B is a panel of microscopic visual fields showing S1 cells overexpressing FAM83A cultured in 2D or 3D 1rECM. FIG. 12C is a panel of confocal images of α6 integrin staining of S1 cells overexpressing FAM83A or vector control grown on 3D 1rECM.

FIG. 13A is a western blot showing detection of FAM83A by a polyclonal antibody against FAM83A. FIG. 13B is a schematic illustration of putative FAM83A isoforms.

FIG. 17A is a graph measuring growth of tumors derived from T4-2 cells treated with control or FAM83A-siRNA and xenografted in nude mice. FIG. 17B is a graph measuring growth of tumors derived from T4-2 cells treated with control or FAM83A-shRNA and xenografted in nude mice. FIG. 17C is a panel of microscopic visual fields showing T4-2 cells overexpressing control vector or FAM83A in the presence of DMSO, lapatinib, or gefitinib. FIG. 17D is a graph measuring growth of tumors derived from T4-2 cells overexpressing control vector or FAM83A and xenografted in nude mice, which were treated with vehicle control or lapatinib (30 mg/kg). FIG. 17E is a Kaplan-Meier curve for a cohort of 159 patient samples.

FIG. 18A is a graph showing tumor growth of T4-2 cells in animals treated with oral gavage of vehicle control or lapatinib (30 mg/kg or 100 mg/kg). FIG. 18B is a panel of microscopic visual fields showing hematoxylin and eosin stained sections of tumors derived from T4-2 cells overexpressing control vector or FAM83A and xenografted in mice, which were treated with oral gavage of vehicle control or lapatinib (30 mg/kg).

DETAILED DESCRIPTION

Figure 1:
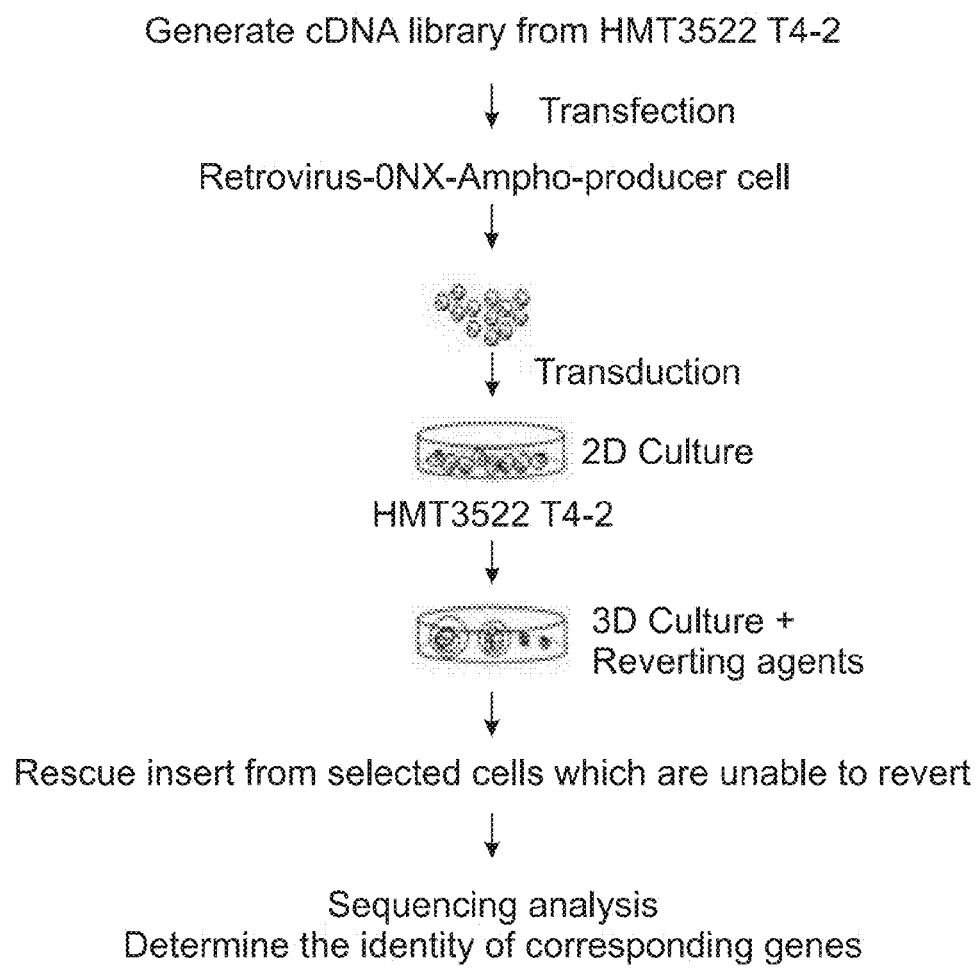
FIG. 1 is a schematic illustration of the experimental protocol of phenotypic screening to identify genes that confer resistance to EGFR tyrosine kinase inhibitors in breast cancer cells.

Embodiments of the present invention relate to methods of identifying genes that confer resistance to EGFR tyrosine kinase inhibitors in breast cancer cells. In various aspects, such methods involve expressing a cDNA library in breast cancer cells, administering an EGFR tyrosine kinase inhibitor, and detecting reversion of the breast cancer cells to a phenotypically normal structure, for example a polarized acinus, in response to the inhibitor. Genes that confer resistance to the EGFR tyrosine kinase inhibitor can be identified by nucleotide sequencing from cells that do not undergo the reversion to a phenotypically normal structure.

Other embodiments of the present invention relate to methods of diagnosing breast cancer resistance to an EGFR tyrosine kinase inhibitor. In various aspects, such methods of diagnosis involve obtaining a biological sample comprising mammary cells from a subject and detecting FAM83A levels in the mammary cells.

Additionally, several embodiments of the present invention relate to methods of identifying a therapeutic compound for treating breast cancer cells resistant to an EGFR tyrosine kinase inhibitor. In various aspects, such methods involve identifying a gene that confers resistance to an EGFR tyrosine kinase inhibitor, administering a compound that inhibits expression of the identified gene or the activity of its encoded protein to the breast cancer cells, and detecting reversion of the breast cancer cells to a phenotypically normal structure, for example a polarized acinus, in response to administration of the compound.

I. Definitions

It is to be understood that both the foregoing and the following descriptions are examples and explanatory only and are not restrictive of the invention as claimed. In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise.

All documents, or portions of documents, cited in this application, including but not limited to patents, patent applications, articles, books, and treatises, are hereby expressly incorporated by reference in their entirety for any purpose.

The term "administration" or "administering" includes routes of introducing a FAM83A inhibitor to a subject to perform its intended function. Examples of routes of administration that may be used include injection (subcutaneous, intravenous, parenterally, intraperitoneally, intrathecal), or oral routes. Pharmaceutical preparations may be given by forms suitable for each administration route. For example, these preparations are administered in tablets or capsule form, by injection, inhalation, infusion, or inhalation. Oral administration is preferred. The injection can be bolus or can be continuous infusion. Depending on the route of administration, a FAM83A inhibitor can be coated with or disposed in a selected material to protect it from natural conditions that may detrimentally affect its ability to perform its intended function. A FAM83A inhibitor can be administered alone, or in conjunction with either another agent or agents as described above or with a pharmaceutically-acceptable carrier, or both. A FAM83A inhibitor can be administered prior to the administration of the other agent, simultaneously with the agent, or after the administration of the agent. Furthermore, a FAM83A inhibitor can also be administered in a proform, which is converted into its active metabolite, or more active metabolite in vivo.

Administration "in combination with" one or more further therapeutic agents includes simultaneous (concurrent) and consecutive administration in any order.

As will be readily apparent to one skilled in the art, the useful in vivo dosage to be administered and the particular mode of administration will vary depending upon the age, weight and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved.

As used herein, an "increase" or "decrease" in a measurement, unless otherwise specified, is typically in comparison to a baseline or control value. For example, an increase in FAM83A RNA or protein levels may be in comparison to a baseline or control value of such measurements. For example, an increase in FAM83A RNA or protein levels in cancer cells such as breast cancer cells may be in comparison to corresponding levels in normal cells such as normal breast cells. In some instances an increase or decrease in a measurement can be evaluated based on the context in which the term is used. For example, an increase or decrease in a measurement can be evaluated based on comparison to control or placebo.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN, polyethylene glycol (PEG).

The term "effective amount" includes an amount effective, at dosages and for periods of time necessary, to achieve the desired result, e.g., sufficient to inhibit or reduce cell growth, inhibit or reduce cell invasion or invasiveness, inhibit or reduce cell spreading, or induce reversion to phenotypically normal structure (e.g. acinar structure). An effective amount of a FAM83A inhibitor may vary according to factors such as the disease state, age, and weight of the subject, and the ability of a FAM83A inhibitor to elicit a desired response in the subject. Dosage regimens may be adjusted to provide the optimum therapeutic response. An effective amount is also one in which any toxic or detrimental effects (e.g., side effects) of a FAM83A inhibitor are outweighed by the therapeutically beneficial effects.

"Ameliorate," "amelioration," "improve," "improvement" or the like refers to, for example, a detectable improvement or a detectable change consistent with improvement that occurs in a subject or in at least a minority of subjects, e.g., in at least about 2%, 5%, 10%, 15%, 20%, 25%, 30%, 40%, 50%, 60%, 70%, 75%, 80%, 85%, 90%, 95%, 98%, 100% or in a range between about any two of these values. Such improvement or change may be observed in treated subjects as compared to subjects not treated with a FAM83A inhibitor, where the untreated subjects have, or are subject to developing, the same or similar disease, condition, symptom or the like. Amelioration of a disease, condition, symptom or assay parameter may be determined subjectively or objectively, e.g., self assessment by a subject(s), by a clinician's assessment or by conducting an appropriate assay or measurement, including, e.g., a quality of life assessment, a slowed progression of a disease(s) or condition(s), a reduced severity of a disease(s) or condition(s), or a suitable assay(s) for the level or activity(ies) of a biomolecule(s), cell(s) or by detection of cancer. Amelioration may be transient, prolonged or permanent or it may be variable at relevant times during or after a FAM83A inhibitor is administered to a subject or is used in an assay or other method described herein or a cited reference.

The "modulation" of, e.g., a symptom, level or biological activity of a molecule, or the like, refers, for example, that the symptom or activity, or the like is detectably increased or decreased. Such increase or decrease may be observed in treated subjects as compared to subjects not treated with a FAM83A inhibitor, where the untreated subjects have, or are subject to developing, the same or similar disease, condition, symptom or the like. Such increases or decreases may be at least about 2%, 5%, 10%, 15%, 20%, 25%, 30%, 40%, 50%, 60%, 70%, 75%, 80%, 85%, 90%, 95%, 98%, 100%, 150%, 200%, 250%, 300%, 400%, 500%, 1000% or more or within any range between any two of these values. Modulation may be determined subjectively or objectively, e.g., by the subject's self assessment, by a clinician's assessment or by conducting an appropriate assay or measurement, including, e.g., quality of life assessments or suitable assays for the level or activity of molecules, for example receptors. Modulation may be transient, prolonged or permanent or it may be variable at relevant times during or after a FAM83A inhibitor is administered to a subject or is used in an assay or other method described herein or a cited reference, e.g., within times described herein.

The term "obtaining" as in "obtaining a FAM83A inhibitor" is intended to include purchasing, synthesizing or otherwise acquiring a FAM83A inhibitor.

The phrases "parenteral administration" and "administered parenterally" as used herein includes, for example, modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The language "a prophylactically effective amount" of a compound refers to an amount of a FAM83A inhibitor which is effective, upon single or multiple dose administration to the subject, in preventing or treating cancer such as breast cancer.

The term "pharmaceutical agent composition" (or agent or drug) as used herein refers to a chemical compound, composition, agent or drug capable of inducing a desired therapeutic effect when properly administered to a patient. It does not necessarily require more than one type of ingredient.

The compositions may be in the "pharmaceutical form" of tablets, capsules, powders, granules, lozenges, liquid or gel preparations. Tablets and capsules for oral administration may be in a form suitable for unit dose presentation and may contain conventional excipients. Examples of these are: binding agents such as syrup, acacia, gelatin, sorbitol, tragacanth, and polyvinylpyrrolidone; fillers such as lactose, sugar, maize-starch, calcium phosphate, sorbitol or glycine; tableting lubricants, such as magnesium stearate, silicon dioxide, talc, polyethylene glycol or silica; disintegrants, such as potato starch; or acceptable wetting agents, such as sodium lauryl sulfate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, e.g., sorbitol, syrup, methyl cellulose, glucose syrup, gelatin, hydrogenated edible fats, emulsifying agents, e.g., lecithin, sorbitan monooleate, or acacia; non-aqueous vehicles (including edible oils), e.g., almond oil, fractionated coconut oil, oily esters such as glycerine, propylene glycol, or ethyl alcohol; preservatives such as methyl or propyl p-hydroxybenzoate or sorbic acid, and, if desired, conventional flavoring or coloring agents.

The term "pharmaceutical preparation" or "pharmaceutical formulation" refers to a pharmaceutical agent composition that can be in a pharmaceutical form described herein.

The phrases "systemic administration," "administered systemically," "peripheral administration," and "administered peripherally," as used herein mean the administration of a FAM83A inhibitor, drug or other material, such that it enters the subject's system and, thus, is subject to metabolism and other like processes, for example, subcutaneous administration.

The language "therapeutically effective amount" of a FAM83A inhibitor refers to an amount of a FAM83A inhibitor which is effective, upon single or multiple dose administration to the subject, to inhibit or reduce cell growth, inhibit or reduce cell invasion or invasiveness, inhibit or reduce cell spreading, or induce reversion to phenotypically normal structure (e.g. acinar structure).

As used herein, the term "inhibit" refers to prevention or reduction.

As used herein, the term "prophylactically effective amount" refers to the amount of a therapy (e.g., a composition comprising a FAM83A inhibitor) which is sufficient to result in the prevention of the development, recurrence, or onset of cancer such as breast cancer, or to enhance or improve the prophylactic effect(s) of another therapy.

As used herein, the terms "breast cell" and "mammary cells" are interchangeable.

As used herein, the term "cDNA library" comprises one or more cDNA molecules and is understood not to be limited to a particular number of cDNA molecules or complexity.

As used herein, the term "reverting agent" refers to any agent capable of inducing reversion of a cancer cell to a phenotypically normal structure.

As used herein, the term "phenotypically normal structure" refers to a phenotype that is more normal compared to that of a cancer cell and is understood not to be limited to any particular degree or extent of normality.

As used herein, "subject" includes organisms which are capable of suffering from cancer, such as breast cancer, treatable by a FAM83A inhibitor or who could otherwise benefit from the administration of a FAM83A inhibitor as described herein, such as human and non-human animals. Preferred human animals include human subjects. The term "non-human animals" of the invention includes all vertebrates, e.g., mammals, e.g., rodents, e.g., mice, rats, and non-mammals, such as non-human primates, e.g., sheep, dog, cow, chickens, amphibians, reptiles, etc.

II. Methods of Identifying Genes that Confer Breast Cancer Resistance to EGFR Tyrosine Kinase Inhibitors Several embodiments described herein relate to the discovery that breast cancer cells growing in a three-dimensional culture in vitro can be induced by EGFR tyrosine kinase inhibitors to revert to phenotypically normal structures, such as polarized acinii. Various embodiments described herein are drawn to methods of identifying a gene by screening a cDNA library for ability to inhibit breast cancer cell reversion to a phenotypically normal structure in response to an EGFR tyrosine kinase inhibitor.

In one embodiment, a method of identifying a gene that confers resistance to EGFR tyrosine kinase inhibitor is provided comprising expressing a cDNA library in breast cancer cells; administering the EGFR tyrosine kinase inhibitor to the breast cancer cells; detecting reversion of the breast cancer cells to a phenotypically normal structure in response to the EGFR tyrosine kinase inhibitor; and identifying cDNA from the breast cancer cells that do not undergo the reversion.

In one embodiment, a method of identifying a gene that confers resistance to EGFR tyrosine kinase inhibitor is provided comprising expressing a cDNA library in breast cancer cells by retroviral transduction; administering the EGFR tyrosine kinase inhibitor to the breast cancer cells; detecting reversion of the breast cancer cells to a phenotypically normal structure in response to the EGFR tyrosine kinase inhibitor; and identifying cDNA from the breast cancer cells that do not undergo the reversion.

A cDNA library can be constructed by techniques well known in the art. Available methods in the art for retroviral vector selection, mRNA isolation, cDNA synthesis and cloning, retrovirus production and titration, and retroviral transduction can be performed to express a cDNA library in breast cancer cells in various embodiments disclosed herein. It will be understood that a cDNA library can be expressed in breast cancer cells by any means of introducing exogenous cDNA into a cell, for example via transfection or transduction.

In one embodiment, a method of identifying a gene that confers resistance to EGFR tyrosine kinase inhibitor is provided comprising expressing a cDNA library in breast cancer cells growing in two-dimensional culture; administering the EGFR tyrosine kinase inhibitor to the breast cancer cells; detecting reversion of the breast cancer cells to a phenotypically normal structure in response to the EGFR tyrosine kinase inhibitor; and identifying cDNA from the breast cancer cells that do not undergo the reversion.

In one embodiment, a method of identifying a gene that confers resistance to EGFR tyrosine kinase inhibitor is provided comprising expressing a cDNA library in breast cancer cells; administering the EGFR tyrosine kinase inhibitor to the breast cancer cells growing in a three-dimensional culture; detecting reversion of the breast cancer cells to a phenotypically normal structure in response to the EGFR tyrosine kinase inhibitor; and identifying cDNA from the breast cancer cells that do not undergo the reversion. It will be appreciated that any three-dimensional culture which permits detection of breast cancer cell reversion to a phenotypically normal structure in response to the EGFR tyrosine kinase inhibitor can be used in the present embodiment. For example, a three-dimensional culture which includes growth factor reduced laminin rich extracellular matrix (3D lrECM) may be used.

In one embodiment, a method of identifying a gene that confers resistance to EGFR tyrosine kinase inhibitor is provided comprising expressing a cDNA library in HMT3522 T4-2 cells; administering the EGFR tyrosine kinase inhibitor to the HMT3522 T4-2 cells; detecting reversion of the HMT3522 T4-2 cells to a phenotypically normal structure in response to the EGFR tyrosine kinase inhibitor; and identifying cDNA from the HMT3522 T4-2 cells that do not undergo the reversion.

In one embodiment, a method of identifying a gene that confers resistance to an EGFR tyrosine kinase inhibitor, such as AG1478 (also called Tyrphostin), gefitinib, or lapatinib, is provided comprising expressing a cDNA library in breast cancer cells; administering an EGFR tyrosine kinase inhibitor, such as AG1478, gefitinib, or lapatinib, to the breast cancer cells; detecting reversion of the breast cancer cells to a phenotypically normal structure in response to the EGFR tyrosine kinase inhibitor; and identifying cDNA from the breast cancer cells that do not undergo the reversion.

In one embodiment, a method of identifying a gene that confers resistance to EGFR tyrosine kinase inhibitor is provided comprising expressing a cDNA library in breast cancer cells; administering the EGFR tyrosine kinase inhibitor to the breast cancer cells; detecting reversion of the breast cancer cells to an acinar structure in response to the EGFR tyrosine kinase inhibitor; and identifying cDNA from the breast cancer cells that do not undergo the reversion. Detecting reversion of the breast cancer cells to an acinar structure in response to the EGFR tyrosine kinase inhibitor can be performed, for example, by visualizing cell morphology by microscopy. Additionally, detecting reversion of the breast cancer cells to an acinar structure in response to the EGFR tyrosine kinase inhibitor can be performed, for example, by visualizing basally polarized expression of a protein marker, such as α6-integrin, by immunofluorescence.

In one embodiment, a method of identifying a gene that confers resistance to an EGFR tyrosine kinase inhibitor is provided comprising expressing a cDNA library in breast cancer cells; administering the EGFR tyrosine kinase inhibitor to the breast cancer cells; detecting reversion of the breast cancer cells to a polarized structure in response to the EGFR tyrosine kinase inhibitor; and identifying cDNA from the breast cancer cells that do not undergo the reversion. Detecting reversion of the breast cancer cells to a polarized structure in response to the EGFR tyrosine kinase inhibitor can be performed, for example, by visualizing cell morphology by microscopy. Additionally, detecting reversion of the breast cancer cells to a polarized structure in response to the EGFR tyrosine kinase inhibitor can be performed, for example, by visualizing basally polarized expression of a protein marker, such as α6-integrin, by immunofluorescence.

In one embodiment, a method of identifying a gene that confers resistance to an EGFR tyrosine kinase inhibitor is provided comprising expressing a cDNA library in breast cancer cells; administering the EGFR tyrosine kinase inhibitor to the breast cancer cells; detecting reversion of the breast cancer cells to a phenotypically normal structure in response to the EGFR tyrosine kinase inhibitor; and identifying cDNA from the breast cancer cells that do not undergo the reversion by nucleotide sequencing.

III. Methods of Identifying Genes that Confer Breast Cancer Resistance to PI3K Inhibitors Several embodiments described herein relate to the discovery that breast cancer cells growing in a three-dimensional culture in vitro can be induced by phosphatidylinositol 3-kinase (PI3K) inhibitors to revert to phenotypically normal structures, such as polarized acinii. Various embodiments described herein are drawn to methods of identifying a gene by screening a cDNA library for ability to inhibit breast cancer cell reversion to a phenotypically normal structure in response to a PI3K inhibitor.

In one embodiment, a method of identifying a gene that confers resistance to PI3K inhibitor is provided comprising expressing a cDNA library in breast cancer cells; administering the PI3K inhibitor to the breast cancer cells; detecting reversion of the breast cancer cells to a phenotypically normal structure in response to the PI3K inhibitor; and identifying cDNA from the breast cancer cells that do not undergo the reversion.

In one embodiment, a method of identifying a gene that confers resistance to PI3K inhibitor is provided comprising expressing a cDNA library in breast cancer cells by retroviral transduction; administering the PI3K inhibitor to the breast cancer cells; detecting reversion of the breast cancer cells to a phenotypically normal structure in response to the PI3K inhibitor; and identifying cDNA from the breast cancer cells that do not undergo the reversion.

A cDNA library can be constructed by techniques well known in the art. Available methods in the art for retroviral vector selection, mRNA isolation, cDNA synthesis and cloning, retrovirus production and titration, and retroviral transduction can be performed to express a cDNA library in breast cancer cells in various embodiments disclosed herein. It will be understood that a cDNA library can be expressed in breast cancer cells by any means of introducing exogenous cDNA into a cell, such as via transfection, for example.

In one embodiment, a method of identifying a gene that confers resistance to PI3K inhibitor is provided comprising expressing a cDNA library in breast cancer cells growing in two-dimensional culture; administering the PI3K inhibitor to the breast cancer cells; detecting reversion of the breast cancer cells to a phenotypically normal structure in response to the PI3K inhibitor; and identifying cDNA from the breast cancer cells that do not undergo the reversion.

In one embodiment, a method of identifying a gene that confers resistance to PI3K inhibitor is provided comprising expressing a cDNA library in breast cancer cells; administering the PI3K inhibitor to the breast cancer cells growing in a three-dimensional culture; detecting reversion of the breast cancer cells to a phenotypically normal structure in response to the PI3K inhibitor; and identifying cDNA from the breast cancer cells that do not undergo the reversion. It will be appreciated that any three-dimensional culture which permits detection of breast cancer cell reversion to a phenotypically normal structure in response to the PI3K inhibitor can be used in the present embodiment. For example, a three-dimensional culture which includes growth factor reduced laminin rich extracellular matrix (3D lrECM) may be used.

In one embodiment, a method of identifying a gene that confers resistance to PI3K inhibitor is provided comprising expressing a cDNA library in HMT3522 T4-2 cells; administering the PI3K inhibitor to the HMT3522 T4-2 cells; detecting reversion of the HMT3522 T4-2 cells to a phenotypically normal structure in response to the PI3K inhibitor; and identifying cDNA from the HMT3522 T4-2 cells that do not undergo the reversion.

In one embodiment, a method of identifying a gene that confers resistance to the PI3K inhibitor LY294002 is provided comprising expressing a cDNA library in breast cancer cells; administering LY294002 to the breast cancer cells; detecting reversion of the breast cancer cells to a phenotypically normal structure in response to the PI3K inhibitor; and identifying cDNA from the breast cancer cells that do not undergo the reversion.

In one embodiment, a method of identifying a gene that confers resistance to PI3K inhibitor is provided comprising expressing a cDNA library in breast cancer cells; administering the PI3K inhibitor to the breast cancer cells; detecting reversion of the breast cancer cells to an acinar structure in response to the PI3K inhibitor; and identifying cDNA from the breast cancer cells that do not undergo the reversion. Detecting reversion of the breast cancer cells to an acinar structure in response to the PI3K inhibitor can be performed, for example, by visualizing cell morphology by microscopy. Additionally, detecting reversion of the breast cancer cells to an acinar structure in response to the PI3K inhibitor can be performed, for example, by visualizing basally polarized expression of a protein marker, such as α6-integrin, by immunofluorescence.

In one embodiment, a method of identifying a gene that confers resistance to PI3K inhibitor is provided comprising expressing a cDNA library in breast cancer cells; administering the PI3K inhibitor to the breast cancer cells; detecting reversion of the breast cancer cells to a polarized structure in response to the PI3K inhibitor; and identifying cDNA from the breast cancer cells that do not undergo the reversion. Detecting reversion of the breast cancer cells to a polarized structure in response to the PI3K inhibitor can be performed, for example, by visualizing cell morphology by microscopy. Additionally, detecting reversion of the breast cancer cells to a polarized structure in response to the PI3K inhibitor can be performed, for example, by visualizing basally polarized expression of a protein marker, such as α6-integrin, by immunofluorescence.

In one embodiment, a method of identifying a gene that confers resistance to PI3K inhibitor is provided comprising expressing a cDNA library in breast cancer cells; administering the PI3K inhibitor to the breast cancer cells; detecting reversion of the breast cancer cells to a phenotypically normal structure in response to the PI3K inhibitor; and identifying cDNA from the breast cancer cells that do not undergo the reversion by nucleotide sequencing.

IV. Methods of Identifying Therapeutic Compounds for Treating Breast Cancer Cells Resistant to Egfr Tyrosine Kinase Inhibitors Several embodiments described herein relate to the discovery of screening methods for identifying genes that confer breast cancer resistance to EGFR tyrosine kinase inhibitors. A variety of embodiments are drawn to methods of identifying therapeutic compounds for treating breast cancer cells resistant to EGFR tyrosine kinase inhibitors by targeting genes identified in the screening methods of the present invention.

In one embodiment, a method of identifying a therapeutic compound for treating breast cancer cells resistant to EGFR tyrosine kinase inhibitor is provided. In such a method, a gene that confers breast cancer resistance to an EGFR tyrosine kinase inhibitor is identified by screening a cDNA library according to the various embodiments disclosed herein. For example, a gene is identified by expressing a cDNA library in breast cancer cells; administering the EGFR tyrosine kinase inhibitor to the breast cancer cells; detecting reversion of the breast cancer cells to a phenotypically normal structure in response to the EGFR tyrosine kinase inhibitor; and identifying cDNA from the breast cancer cells that do not undergo the reversion. A therapeutic compound for treating breast cancer cells resistant to EGFR tyrosine kinase inhibitor is then identified by administering a compound that inhibits expression of the identified gene or activity of its encoded protein in breast cancer cells and detecting reversion of the breast cancer cells to a phenotypically normal structure in response to the compound.

In one embodiment, a method of identifying a therapeutic compound for treating breast cancer cells resistant to an EGFR tyrosine kinase inhibitor, such as AG1478, gefitinib, or lapatinib, is provided. In such a method, a gene that confers breast cancer resistance to an EGFR tyrosine kinase inhibitor, such as AG1478, gefitinib, or lapatinib is identified by screening a cDNA library according to the various embodiments disclosed herein. For example, a gene is identified by expressing a cDNA library in breast cancer cells; administering an EGFR tyrosine kinase inhibitor to the breast cancer cells; detecting reversion of the breast cancer cells to a phenotypically normal structure in response to an EGFR tyrosine kinase inhibitor; and identifying cDNA from the breast cancer cells that do not undergo the reversion. A therapeutic compound for treating breast cancer cells resistant to an EGFR tyrosine kinase inhibitor, such as AG1478, gefitinib, or lapatinib, is then identified by administering a compound that inhibits expression of the identified gene or activity of its encoded protein in breast cancer cells and detecting reversion of the breast cancer cells to a phenotypically normal structure in response to the compound.

It will be appreciated that a therapeutic compound can be identified by developing a compound against a gene or its encoded protein as identified by any of the foregoing embodiments related to methods of identifying such genes and screening for phenotypic reversion of breast cancer cells in response to the compound.

V. Methods of Identifying Therapeutic Compounds for Treating Breast Cancer Cells Resistant to PI3K Inhibitors Several embodiments described herein relate to the discovery of screening methods for identifying genes that confer breast cancer resistance to PI3K inhibitors. A variety of embodiments are drawn to methods of identifying therapeutic compounds for treating breast cancer cells resistant to PI3K inhibitors by targeting genes identified in the screening methods of the present invention.

In one embodiment, a method of identifying a therapeutic compound for treating breast cancer cells resistant to PI3K inhibitor is provided. In such a method, a gene that confers breast cancer resistance to a PI3K inhibitor is identified by screening a cDNA library according to the various embodiments disclosed herein. For example, a gene is identified by expressing a cDNA library in breast cancer cells; administering the PI3K inhibitor to the breast cancer cells; detecting reversion of the breast cancer cells to a phenotypically normal structure in response to the PI3K inhibitor; and identifying cDNA from the breast cancer cells that do not undergo the reversion. A therapeutic compound for treating breast cancer cells resistant to PI3K inhibitor is then identified by administering a compound that inhibits expression of the identified gene or activity of its encoded protein in breast cancer cells and detecting reversion of the breast cancer cells to a phenotypically normal structure in response to the compound.

In one embodiment, a method of identifying a therapeutic compound for treating breast cancer cells resistant to LY294002 is provided. In such a method, a gene that confers breast cancer resistance to LY294002 is identified by screening a cDNA library according to the various embodiments disclosed herein. For example, a gene is identified by expressing a cDNA library in breast cancer cells; administering LY294002 to the breast cancer cells; detecting reversion of the breast cancer cells to a phenotypically normal structure in response to LY294002; and identifying cDNA from the breast cancer cells that do not undergo the reversion. A therapeutic compound for treating breast cancer cells resistant to LY294002 is then identified by administering a compound that inhibits expression of the identified gene or activity of its encoded protein in breast cancer cells and detecting reversion of the breast cancer cells to a phenotypically normal structure in response to the compound.

It will be appreciated that a therapeutic compound can be identified by developing a compound against a gene as identified by any of the foregoing embodiments related to methods of identifying such genes and screening for phenotypic reversion of breast cancer cells in response to the compound.

VI. Methods of Diagnosing Cancer Resistance to Egfr Tyrosine Kinase Inhibitors

Several embodiments described herein relate to the discovery of FAM83A and Rab32 from the described methods of identifying genes that confer breast cancer cell resistance to an EGFR tyrosine kinase inhibitor. Various embodiments also relate to the discovery that FAM83A and Rab32 confer breast cancer cell resistance to an EGFR tyrosine kinase inhibitor. Additionally, various embodiments relate to the discovery that FAM83A is expressed at higher levels in breast cancer cells compared to non-malignant breast cells and breast cancer cells that have undergone reversion to a phenotypically normal acinar structure in response to an EGFR tyrosine kinase inhibitor.

The FAM83A cDNA (SEQ ID NO:1) encodes a protein consisting of 434 amino acids (SEQ ID NO:2) and contains a DUF1669 domain, a serine-rich domain and several protein-protein interaction domains including a proline-rich domain (PRD). Rab32 belongs to the Ras oncogene family of the small GTPases, which are involved in a variety of cellular functions including the formation of vesicles at the membrane, protein trafficking, and cytoskeleton remodeling.

It will be appreciated that FAM83A and Rab32 may confer resistance to EGFR tyrosine kinase inhibitors in any tumor, not limited to breast, in which EGFR is aberrantly active. The cancer can be selected from the group consisting of: melanoma, epithelial cancer, squamous cell cancer, small cell lung cancer, non-small cell lung cancer, glioma, hepatocellular (liver) carcinoma, thyroid tumor, a leukemia, gastric (stomach) cancer, prostate cancer, breast cancer, ovarian cancer, bladder cancer, lung cancer, glioblastoma, endometrial cancer, kidney cancer, colon cancer, ovarian cancer, hepatocellular cancer, pancreatic cancer, esophageal carcinoma, head and neck cancers, esophageal cancer, lymphoma, mesothelioma, sarcomas, carcinomas, biliary (cholangiocarcinoma), small bowel adenocarcinoma, pediatric malignancies and epidermoid carcinoma.

In one embodiment, a method of diagnosing cancer resistance to an EGFR tyrosine kinase inhibitor is provided comprising detecting FAM83A or Rab32 mRNA levels in a cancer cell from a subject, wherein increased FAM83A or Rab32 levels relative to control indicate resistance to an EGFR tyrosine kinase inhibitor. In one aspect of the embodiment, the cancer cell is a breast cancer cell.

In one embodiment, FAM83A or Rab32 mRNA levels are detected by RT-PCR. For example, after cDNA synthesis by reverse transcription of sample RNA, the following primers may be used to detect FAM83A expression: 5'-GAATTCATGAGCCGGTCAAGGCGCCT-3' (SEQ ID NO:13) and 5'-CGAGCGGCCGCTGAAGGGGTT-3' (SEQ ID NO:14). The expression level of FAM83A mRNA may be normalized with glygeraldehyde-3-phosphate dehydrogenase (GAPDH) levels by using the following primers: 5'-CCCCTGGCCAAGGTCATCCATGAC-3' (SEQ ID NO:15) and 5'-GAAACAGTTCGAGTAAAGGACCATAC-3' (SEQ ID NO:16). It will be understood that other primers may be designed and made using conventional molecular biology techniques in correspondence with the FAM83A cDNA sequence (SEQ ID NO:1).

In one embodiment, FAM83A or Rab32 mRNA levels are detected by in situ hybridization.

In one embodiment, a method of diagnosing cancer resistance to an EGFR tyrosine kinase inhibitor is provided comprising detecting FAM83A or Rab32 protein levels in a cancer cell from a subject, wherein increased FAM83A or Rab32 levels relative to control indicate resistance to an EGFR tyrosine kinase inhibitor. In one aspect of the embodiment, the cancer cell is a breast cancer cell. In another aspect of the embodiment, the FAM83A or Rab32 protein levels are detected with a specific antibody against FAM83A or Rab32.

In one embodiment, FAM83A or Rab32 protein levels are detected with a specific antibody against FAM83A or Rab32 by western blot.

In one embodiment, FAM83A or Rab32 protein levels are detected with a specific antibody against FAM83A or Rab32 by immunohistochemistry.

In the foregoing embodiments, such increase of FAM83A or Rab32 RNA or protein levels can be at least about 2%, 5%, 10%, 15%, 20%, 25%, 30%, 40%, 50%, 60%, 70%, 75%, 80%, 85%, 90%, 95%, 98%, 100%, 150%, 200%, 250%, 300%, 400%, 500%, 1000% or more or within any range between any two of these values.

It will be appreciated that a cancer cell, for example a breast cancer cell, may be obtained from a subject by techniques commonly practiced in the medical field (e.g. biopsy, reduction mammoplasty, mastectomy, etc.) in any of the foregoing embodiments.

In various embodiments, detection of increased levels of FAM83A is diagnostic of a variety of cancers resistant to EGFR tyrosine kinase inhibitors. The cancer can be selected from the group consisting of: melanoma, epithelial cancer, squamous cell cancer, small cell lung cancer, non-small cell lung cancer, glioma, hepatocellular (liver) carcinoma, thyroid tumor, a leukemia, gastric (stomach) cancer, prostate cancer, breast cancer, ovarian cancer, bladder cancer, lung cancer, glioblastoma, endometrial cancer, kidney cancer, colon cancer, ovarian cancer, hepatocellular cancer, pancreatic cancer, esophageal carcinoma, head and neck cancers, esophageal cancer, lymphoma, mesothelioma, sarcomas, carcinomas, biliary (cholangiocarcinoma), small bowel adenocarcinoma, pediatric malignancies and epidermoid carcinoma.

VII. Methods of Diagnosing Cancer Resistance to PI3K Inhibitors

Several embodiments described herein relate to the discovery of MRGBP (Mor4—related gene binding protein), PTBP1 (Polypyrimidine tract binding protein variant 1), and ZFPL1 (Zinc-finger protein like1) from the embodiments of the present invention related to methods of identifying genes that confer breast cancer cell resistance to PI3K inhibitor. Various embodiments also relate to the discovery that MRGBP, PTBP1, and ZFPL1 confer breast cancer cell resistance to PI3K inhibitor.

MRGBP (Mor4—related gene binding protein) is a component of the ATM/PI3-kinase related TRRAP protein (transformation/transcription domain-associated protein) and HAT (histone acetyltransferase)/TIP60 complex which are responsible for transcriptional regulation and chromatin remodeling. PTBP1 (Polypyrimidine tract binding protein variant 1) is an abundant eukaryotic RNA binding protein. PTBP1 has been known as a heterogeneous nuclear ribonucleoproteins (hnRNPs) involved in mRNA metabolism including mRNA stability, transport, and the repression of alternative splicing of exons. ZFPL1 (Zinc-finger protein like1) is localized on 13q region of chromosome 11 and expressed strongly in the exocrine pancreas.

It will be appreciated that MRGBP, PTBP1, or ZFPL1 may confer resistance to PI3K inhibitors in any tumor, not limited to breast, in which EGFR is aberrantly active. The cancer can be selected from the group consisting of: melanoma, epithelial cancer, squamous cell cancer, small cell lung cancer, non-small cell lung cancer, glioma, hepatocellular (liver) carcinoma, thyroid tumor, a leukemia, gastric (stomach) cancer, prostate cancer, breast cancer, ovarian cancer, bladder cancer, lung cancer, glioblastoma, endometrial cancer, kidney cancer, colon cancer, ovarian cancer, hepatocellular cancer, pancreatic cancer, esophageal carcinoma, head and neck cancers, esophageal cancer, lymphoma, mesothelioma, sarcomas, carcinomas, biliary (cholangiocarcinoma), small bowel adenocarcinoma, pediatric malignancies and epidermoid carcinoma.

In one embodiment, a method of diagnosing cancer resistance to a PI3K inhibitor is provided comprising detecting MRGBP, PTBP1, or ZFPL1 RNA levels in a cancer cell from a subject, wherein increased MRGBP, PTBP1, or ZFPL1 levels relative to control indicate resistance to an PI3K inhibitor. In one aspect of the embodiment, the cancer cell is a breast cancer cell.

In one embodiment, MRGBP, PTBP1, or ZFPL1 mRNA levels are detected by RT-PCR.

In one embodiment, MRGBP, PTBP1, or ZFPL1 mRNA levels are detected by in situ hybridization.

In one embodiment, a method of diagnosing cancer resistance to a PI3K inhibitor is provided comprising detecting MRGBP, PTBP1, or ZFPL1 protein levels in a cancer cell from a subject, wherein increased MRGBP, PTBP1, or ZFPL1 levels relative to control indicate resistance to an PI3K inhibitor. In one aspect of the embodiment, the cancer cell is a breast cancer cell. In another aspect of the embodiment, the MRGBP, PTBP1, or ZFPL1 protein levels are detected with a specific antibody against MRGBP, PTBP1, or ZFPL1.

In one embodiment, MRGBP, PTBP1, or ZFPL1 protein levels are detected with a specific antibody against MRGBP, PTBP1, or ZFPL1 by western blot.

In one embodiment, MRGBP, PTBP1, or ZFPL1 protein levels are detected with a specific antibody against MRGBP, PTBP1, or ZFPL1 by immunohistochemistry.

In the foregoing embodiments, such increase of MRGBP, PTBP1, or ZFPL1 mRNA or protein levels can be at least about 2%, 5%, 10%, 15%, 20%, 25%, 30%, 40%, 50%, 60%, 70%, 75%, 80%, 85%, 90%, 95%, 98%, 100%, 150%, 200%, 250%, 300%, 400%, 500%, 1000% or more or within any range between any two of these values.

It will be appreciated that a cancer cell, for example a breast cancer cell, may be obtained from a subject by techniques commonly practiced in the medical field (e.g. biopsy, reduction mammoplasty, mastectomy, etc.) in any of the foregoing embodiments.

In various embodiments, detection of increased levels of MRGBP, PTBP1, or ZFPL1 is diagnostic of a variety of cancers resistant to EGFR tyrosine kinase inhibitors. The cancer can be selected from the group consisting of: melanoma, epithelial cancer, squamous cell cancer, small cell lung cancer, non-small cell lung cancer, glioma, hepatocellular (liver) carcinoma, thyroid tumor, a leukemia, gastric (stomach) cancer, prostate cancer, breast cancer, ovarian cancer, bladder cancer, lung cancer, glioblastoma, endometrial cancer, kidney cancer, colon cancer, ovarian cancer, hepatocellular cancer, pancreatic cancer, esophageal carcinoma, head and neck cancers, esophageal cancer, lymphoma, mesothelioma, sarcomas, carcinomas, biliary (cholangiocarcinoma), small bowel adenocarcinoma, pediatric malignancies and epidermoid carcinoma.

VIII. Antisense and Sirna Inhibitors of Fam83A Modulation of Target Expression

Modulation of expression of a target nucleic acid can be achieved through alteration of any number of nucleic acid (DNA or RNA) functions. "Modulation" means a perturbation of function, for example, either an increase (stimulation or induction) or a decrease (inhibition or reduction) in expression. As another example, modulation of expression can include perturbing splice site selection of pre-mRNA processing. "Expression" includes all the functions by which a gene's coded information is converted into structures present and operating in a cell. These structures include the products of transcription and translation. "Modulation of expression" means the perturbation of such functions. The functions of RNA to be modulated can include translocation functions, which include, but are not limited to, translocation of the RNA to a site of protein translation, translocation of the RNA to sites within the cell which are distant from the site of RNA synthesis, and translation of protein from the RNA. RNA processing functions that can be modulated include, but are not limited to, splicing of the RNA to yield one or more RNA species, capping of the RNA, 3' maturation of the RNA and catalytic activity or complex formation involving the RNA which may be engaged in or facilitated by the RNA. Modulation of expression can result in the increased level of one or more nucleic acid species or the decreased level of one or more nucleic acid species, either temporally or by net steady state level. One result of such interference with target nucleic acid function is modulation of the expression of FAM83A. Thus, in one embodiment modulation of expression can mean increase or decrease in target RNA or protein levels. In another embodiment modulation of expression can mean a decrease or increase of one or more RNA splice products, or a change in the ratio of two or more splice products.

The effect of antisense compounds of the present invention on target nucleic acid expression can be tested in any of a variety of cell types provided that the target nucleic acid is present at measurable levels. The effect of antisense compounds of the present invention on target nucleic acid expression can be routinely determined using, for example, PCR or Northern blot analysis. Cell lines are derived from both normal tissues and cell types and from cells associated with various disorders (e.g. hyperproliferative disorders). Cell lines derived from multiple tissues and species can be obtained from American Type Culture Collection (ATCC, Manassas, Va.) and other public sources, and are well known to those skilled in the art. Primary cells, or those cells which are isolated from an animal and not subjected to continuous culture, can be prepared according to methods known in the art, or obtained from various commercial suppliers. Additionally, primary cells include those obtained from donor human subjects in a clinical setting (i.e. blood donors, surgical patients). Primary cells prepared by methods known in the art.

Active Target Segments

The locations on the target nucleic acid defined by having one or more active antisense compounds targeted thereto are referred to as "active target segments." When an active target segment is defined by multiple antisense compounds, the compounds are preferably separated by no more than about 50 nucleotides on the target sequence, more preferably no more than about 10 nucleotides on the target sequence, even more preferably the compounds are contiguous, most preferably the compounds are overlapping. There may be substantial variation in activity (e.g., as defined by percent inhibition) of the antisense compounds within an active target segment. Active antisense compounds are those that modulate the expression of their target RNA in the methods described herein. Active antisense compounds inhibit expression of their target RNA at least about 50%. In a preferred embodiment, at least about 50%, of the oligonucleotides targeted to the active target segment modulate expression of their target RNA at least 65%. In a more preferred embodiment, the level of inhibition required to define an active antisense compound is defined based on the results from the screen used to define the active target segments.

Hybridization

As used herein, "hybridization" means the pairing of complementary strands of antisense compounds to their target sequence. While not limited to a particular mechanism, the most common mechanism of pairing involves hydrogen bonding, which may be Watson-Crick, Hoogsteen or reversed Hoogsteen hydrogen bonding, between complementary nucleoside or nucleotide bases (nucleobases). For example, the natural base adenine is complementary to the natural nucleobases thymidine and uracil which pair through the formation of hydrogen bonds. The natural base guanine is complementary to the natural bases cytosine and 5-methyl cytosine. Hybridization can occur under varying circumstances.

An antisense compound is specifically hybridizable when there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

As used herein, "stringent hybridization conditions" or "stringent conditions" refers to conditions under which an antisense compound will hybridize to its target sequence, but to a minimal number of other sequences. Stringent conditions are sequence-dependent and will be different in different circumstances, and "stringent conditions" under which antisense compounds hybridize to a target sequence are determined by the nature and composition of the antisense compounds and the assays in which they are being investigated.

Complementarity

"Complementarity," as used herein, refers to the capacity for precise pairing between two nucleobases on either two oligomeric compound strands or an antisense compound with its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be a complementary position.

"Complementarity" can also be viewed in the context of an antisense compound and its target, rather than in a base by base manner. The antisense compound and the further DNA or RNA are complementary to each other when a sufficient number of complementary positions in each molecule are occupied by nucleobases which can hydrogen bond with each other. Thus, "specifically hybridizable" and "complementary" are terms which are used to indicate a sufficient degree of precise pairing or complementarity over a sufficient number of nucleobases such that stable and specific binding occurs between the antisense compound and a target nucleic acid. One skilled in the art recognizes that the inclusion of mismatches is possible without eliminating the activity of the antisense compound. The invention is therefore directed to those antisense compounds that may contain up to about 20% nucleotides that disrupt base pairing of the antisense compound to the target. Preferably the compounds contain no more than about 15%, more preferably not more than about 10%, most preferably not more than 5% or no mismatches. The remaining nucleotides do not disrupt hybridization (e.g., universal bases).

Identity

It is understood by those skilled in the art that an antisense compound need not have an identical sequence to those described herein to function similarly to the antisense compound described herein. Shortened versions of antisense compound taught herein, or non-identical versions of the antisense compound taught herein fall within the scope of the invention. Non-identical versions are those wherein each base does not have the same pairing activity as the antisense compounds disclosed herein. Bases do not have the same pairing activity by being shorter or having at least one abasic site. Alternatively, a non-identical version can include at least one base replaced with a different base with different pairing activity (e.g., G can be replaced by C, A, or T). Percent identity is calculated according to the number of bases that have identical base pairing corresponding to the SEQ ID NO or antisense compound to which it is being compared. The non-identical bases may be adjacent to each other, dispersed through out the oligonucleotide, or both.

For example, a 16-mer having the same sequence as nucleobases 2-17 of a 20-mer is 80% identical to the 20-mer. Alternatively, a 20-mer containing four nucleobases not identical to the 20-mer is also 80% identical to the 20-mer. A 14-mer having the same sequence as nucleobases 1-14 of an 18-mer is 78% identical to the 18-mer. Such calculations are well within the ability of those skilled in the art.

The percent identity is based on the percent of nucleobases in the original sequence present in a portion of the modified sequence. Therefore, a 30 nucleobase antisense compound comprising the full sequence of the complement of a 20 nucleobase active target segment would have a portion of 100% identity with the complement of the 20 nucleobase active target segment, while further comprising an additional 10 nucleobase portion. In the context of the invention, the complement of an active target segment may constitute a single portion. In a preferred embodiment, the oligonucleotides of the instant invention are at least about 80%, more preferably at least about 85%, even more preferably at least about 90%, most preferably at least 95% identical to at least a portion of the complement of the active target segments presented herein.

It is well known by those skilled in the art that it is possible to increase or decrease the length of an antisense compound and/or introduce mismatch bases without eliminating activity. It is understood that antisense compounds of the instant invention can vary in length and percent complementarity to the target provided that they maintain the desired activity. Methods to determine desired activity are disclosed herein and well known to those skilled in the art.

Therapeutics

Antisense compounds of the invention can be used to modulate the expression of FAM83A in an animal, such as a human. In one non-limiting embodiment, the methods comprise the step of administering to said animal in need of therapy for a disease or condition associated with FAM83A an effective amount of an antisense compound that inhibits expression of FAM83A. A disease or condition associated with FAM83A includes, but is not limited to cancer. FAM83A can be a therapeutic target in a variety of cancers. For example, FAM83A can be therapeutically targeted in any cancer selected from the group consisting of: melanoma, epithelial cancer, squamous cell cancer, small cell lung cancer, non-small cell lung cancer, glioma, hepatocellular (liver) carcinoma, thyroid tumor, a leukemia, gastric (stomach) cancer, prostate cancer, breast cancer, ovarian cancer, bladder cancer, lung cancer, glioblastoma, endometrial cancer, kidney cancer, colon cancer, ovarian cancer, hepatocellular cancer, pancreatic cancer, esophageal carcinoma, head and neck cancers, esophageal cancer, lymphoma, mesothelioma, sarcomas, carcinomas, biliary (cholangiocarcinoma), small bowel adenocarcinoma, pediatric malignancies and epidermoid carcinoma.

In one embodiment, the antisense compounds of the present invention effectively inhibit the levels or function of FAM83A RNA. Because reduction in FAM83A mRNA levels can lead to alteration in FAM83A protein products of expression as well, such resultant alterations can also be measured. Antisense compounds of the present invention that effectively inhibit the level or function of FAM83A RNA or protein products of expression are considered active antisense compounds. In one embodiment, the antisense compounds of the invention inhibit the expression of FAM83A causing a reduction of RNA or protein levels, preferably in target cells or tissues, by at least 10%, by at least 20%, by at least 25%, by at least 30%, by at least 40%, by at least 50%, by at least 60%, by at least 70%, by at least 75%, by at least 80%, by at least 85%, by at least 90%, by at least 95%, by at least 98%, by at least 99%, or by 100%.

For example, the reduction of the expression of FAM83A can be measured in a biological sample which may contain cells, tissues (e.g., biopsy), or organs of the subject. Methods of preparation of the samples to allow for analysis are well known to those skilled in the art. Methods for analysis of RNA and protein levels are discussed above and are well known to those skilled in the art. The effects of treatment can be assessed by measuring biomarkers associated with the target gene expression in the aforementioned fluids, tissues or organs, collected from an animal contacted with one or more compounds of the invention, by routine clinical methods known in the art. These biomarkers include but are not limited to: liver transaminases, bilirubin, albumin, blood urea nitrogen, creatine and other markers of kidney and liver function; interleukins, tumor necrosis factors, intracellular adhesion molecules, C-reactive protein, chemokines, cytokines, and other markers of inflammation.

The antisense compounds of the present invention can be utilized in pharmaceutical compositions by adding an effective amount of a compound to a suitable pharmaceutically acceptable diluent or carrier. Acceptable carriers and diluents are well known to those skilled in the art. Selection of a diluent or carrier is based on a number of factors, including, but not limited to, the solubility of the compound and the route of administration. Such considerations are well understood by those skilled in the art. In one aspect, the antisense compounds of the present invention inhibit the expression of FAM83A. The compounds of the invention can also be used in the manufacture of a medicament for the treatment of diseases and disorders related to FAM83A expression.

Methods whereby bodily fluids, organs or tissues are contacted with an effective amount of one or more of the antisense compounds or compositions of the invention are also contemplated. Bodily fluids, organs or tissues can be contacted with one or more of the compounds of the invention resulting in modulation of FAM83A expression in the cells of bodily fluids, organs or tissues. An effective amount can be determined by monitoring the modulatory effect of the antisense compound or compounds or compositions on target nucleic acids or their products by methods routine to the skilled artisan.

Thus, provided herein is the use of an isolated single- or double-stranded antisense compound targeted to FAM83A in the manufacture of a medicament for the treatment of a disease or disorder by means of the method described above. In one embodiment, the antisense compound is a single stranded antisense compound. Such antisense compounds can function by any of a number of non-autocatalytic mechanisms including by the action of RNases (e.g., RNaseH) or modulation of splicing. Alternative antisense mechanisms (e.g., RNAi) can be promoted by the inclusion of a second, complementary strand to the antisense compound and/or inclusion of specific chemical modifications which are known to those skilled in the art.

Compounds

The term "oligomeric compound" refers to a polymeric structure capable of hybridizing to a region of a nucleic acid molecule. Generally, oligomeric compounds comprise a plurality of monomeric subunits linked together by internucleoside linking groups and/or internucleoside linkage mimetics. Each of the monomeric subunits comprises a sugar, abasic sugar, modified sugar, or a sugar mimetic, and except for the abasic sugar includes a nucleobase, modified nucleobase or a nucleobase mimetic. Preferred monomeric subunits comprise nucleosides and modified nucleosides.

An "antisense compound" or "antisense oligomeric compound" refers to an oligomeric compound that is at least partially complementary to the region of a target nucleic acid molecule to which it hybridizes and which modulates (increases or decreases) its expression. This term includes oligonucleotides, oligonucleosides, oligonucleotide analogs, oligonucleotide mimetics, antisense compounds, antisense oligomeric compounds, and chimeric combinations of these. Consequently, while all antisense compounds can be said to be oligomeric compounds, not all oligomeric compounds are antisense compounds. An "antisense oligonucleotide" is an antisense compound that is a nucleic acid-based oligomer. An antisense oligonucleotide can, in some cases, include one or more chemical modifications to the sugar, base, and/or internucleoside linkages. Nonlimiting examples of antisense compounds include primers, probes, antisense compounds, antisense oligonucleotides, external guide sequence (EGS) oligonucleotides, alternate splicers, and siRNAs. As such, these compounds can be introduced in the form of single-stranded, double-stranded, circular, branched or hairpins and can contain structural elements such as internal or terminal bulges or loops. Antisense double-stranded compounds can be two strands hybridized to form double-stranded compounds or a single strand with sufficient self complementarity to allow for hybridization and formation of a fully or partially double-stranded compound. The compounds of the instant invention are not auto-catalytic. As used herein, "auto-catalytic" means a compound has the ability to promote cleavage of the target RNA in the absence of accessory factors, e.g. proteins.

In one embodiment of the invention, the antisense compound comprises a single stranded oligonucleotide. In some embodiments of the invention the antisense compound contains chemical modifications. In a preferred embodiment, the antisense compound is a single stranded, chimeric oligonucleotide wherein the modifications of sugars, bases, and internucleoside linkages are independently selected.

The antisense compounds in accordance with this invention may comprise an antisense compound from about 12 to about 35 nucleobases (i.e. from about 12 to about 35 linked nucleosides). In other words, a single-stranded compound of the invention comprises from about 12 to about 35 nucleobases, and a double-stranded antisense compound of the invention (such as a siRNA, for example) comprises two strands, each of which is independently from about 12 to about 35 nucleobases. This includes oligonucleotides 15 to 35 and 16 to 35 nucleobases in length. Contained within the antisense compounds of the invention (whether single or double stranded and on at least one strand) are antisense portions. The "antisense portion" is that part of the antisense compound that is designed to work by one of the aforementioned antisense mechanisms. One of ordinary skill in the art will appreciate that about 12 to about 35 nucleobases includes 12, 13, 14, 15, 16, 17, 18, 19, 20, 21, 22, 23, 24, 25, 26, 27, 28, 29, 30, 31, 32, 33, 34, or 35 nucleobases.

Antisense compounds about 12 to 35 nucleobases in length, preferably about 15 to 35 nucleobases in length, comprising a stretch of at least eight (8), preferably at least 12, more preferably at least 15 consecutive nucleobases targeted to the active target regions are considered to be suitable antisense compounds as well.

Modifications can be made to the antisense compounds of the instant invention and may include conjugate groups attached to one of the termini, selected nucleobase positions, sugar positions or to one of the internucleoside linkages. Possible modifications include, but are not limited to, 2'-fluoro (2'-F), 2'-OMethyl (2'-OMe), 2'-Methoxy ethoxy (2'-MOE) sugar modifications, inverted abasic caps, deoxynucleobases, and bicyclic nucleobase analogs such as locked nucleic acids (including LNA) and ENA.

In one embodiment of the invention, double-stranded antisense compounds encompass short interfering RNAs (siRNAs). As used herein, the term "siRNA" is defined as a double-stranded compound having a first and second strand, each strand having a central portion and two independent terminal portions. The central portion of the first strand is complementary to the central portion of the second strand, allowing hybridization of the strands. The terminal portions are independently, optionally complementary to the corresponding terminal portion of the complementary strand. The ends of the strands may be modified by the addition of one or more natural or modified nucleobases to form an overhang.

Each strand of the siRNA duplex may be from about 12 to about 35 nucleobases. In a preferred embodiment, each strand of the siRNA duplex is about 17 to about 25 nucleobases. The two strands may be fully complementary (i.e., form a blunt ended compound), or include a 5' or 3' overhang on one or both strands. Double-stranded compounds can be made to include chemical modifications as discussed herein. Structures of siRNAs are well known to those skilled in the art (see e.g., Guo and Kempheus, Cell, 1995, 81, 611-620; Montgomery et al., Proc. Natl. Acad. Sci. USA, 1998, 95, 15502-15507; and Fire et al., Nature, 1998, 391, 806-811).

In one embodiment, the siRNA compounds of the invention inhibit the expression of FAM83A causing a reduction of RNA or protein levels, preferably in target cells or tissues, by at least 10%, by at least 20%, by at least 25%, by at least 30%, by at least 40%, by at least 50%, by at least 60%, by at least 70%, by at least 75%, by at least 80%, by at least 85%, by at least 90%, by at least 95%, by at least 98%, by at least 99%, or by 100%.

In one embodiment, the target sequences of the siRNA oligonucleotides for FAM83A have the following nucleotide sequences: 5'-GCCCUACCUGAAGGAAAAA-3' (SEQ ID NO:3), 5'-GGAGAGAUAUACUGUGCCA'3' (SEQ ID NO:4), and 5'-GGAAAUUCGCUGGCCAAAU-3' (SEQ ID NO:5).

In one embodiment, a double-stranded DNA oligonucleotide for FAM83A shRNA production is generated from the following sequences: sense, 5'-GATCCGTGTGGAAG-GAGAGATATACTTCCTGTCA-GATATATCTCTCCTTCCAC ACTTTTTG-3' (SEQ ID NO:7); antisense, 5'-AATTCAAAAAGTGTGGAAG-GAGAGATATATCTGACAGGAAGTATATCTCTCC TTC-CACACG-3' (SEQ ID NO:8).

Chemical Modifications

As is known in the art, a nucleoside is a base-sugar combination. The base portion of the nucleoside is normally a heterocyclic base (sometimes referred to as a "nucleobase" or simply a "base"). The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. In forming oligonucleotides, the phosphate groups covalently link adjacent nucleosides to one another to form a linear polymeric compound. Within oligonucleotides, the phosphate groups are commonly referred to as forming the internucleoside backbone of the oligonucleotide. The normal linkage or backbone of RNA and DNA is a 3' to 5' phosphodiester linkage. It is often preferable to include chemical modifications in oligonucleotides to alter their activity. Chemical modifications can alter oligonucleotide activity by, for example: increasing affinity of an antisense oligonucleotide for its target RNA, increasing nuclease resistance, and/or altering the pharmacokinetics of the oligonucleotide. The use of chemistries that increase the affinity of an oligonucleotide for its target can allow for the use of shorter oligonucleotide compounds.

The term "nucleobase" or "heterocyclic base moiety" as used herein, refers to the heterocyclic base portion of a nucleoside. In general, a nucleobase is any group that contains one or more atom or groups of atoms capable of hydrogen bonding to a base of another nucleic acid. In addition to "unmodified" or "natural" nucleobases such as the purine nucleobases adenine (A) and guanine (G), and the pyrimidine nucleobases thymine (T), cytosine (C) and uracil (U), many modified nucleobases or nucleobase mimetics known to those skilled in the art are amenable to the present invention. The terms modified nucleobase and nucleobase mimetic can overlap but generally a modified nucleobase refers to a nucleobase that is fairly similar in structure to the parent nucleobase, such as for example a 7-deaza purine, a 5-methyl cytosine, or a G-clamp, whereas a nucleobase mimetic would include more complicated structures, such as for example a tricyclic phenoxazine nucleobase mimetic. Methods for preparation of the above noted modified nucleobases are well known to those skilled in the art.

Antisense compounds of the present invention may also contain one or more nucleosides having modified sugar moieties. The furanosyl sugar ring of a nucleoside can be modified in a number of ways including, but not limited to, addition of a substituent group, bridging of two non-geminal ring atoms to form a bicyclic nucleic acid (BNA) and substitution of an atom or group such as —S—, —N(R)— or —C(R$_1$)(R$_2$) for the ring oxygen at the 4'-position. Modified sugar moieties are well known and can be used to alter, typically increase, the affinity of the antisense compound for its target and/or increase nuclease resistance. A representative list of preferred modified sugars includes but is not limited to bicyclic modified sugars (BNA's), including LNA and ENA (4'-(CH$_2$)$_2$—O-2' bridge); and substituted sugars, especially 2'-substituted sugars having a 2'-F, 2'-OCH$_2$ or a 2-O(CH$_2$)$_2$—OCH$_3$ substituent group. Sugars can also be replaced with sugar mimetic groups among others. Methods for the preparations of modified sugars are well known to those skilled in the art.

The present invention includes internucleoside linking groups that link the nucleosides or otherwise modified monomer units together thereby forming an antisense compound. The two main classes of internucleoside linking groups are defined by the presence or absence of a phosphorus atom. Representative phosphorus containing internucleoside linkages include, but are not limited to, phosphodiesters, phosphotriesters, methylphosphonates, phosphoramidate, and phosphorothioates. Representative non-phosphorus containing internucleoside linking groups include, but are not limited to, methylenemethylimino (—CH$_2$—N(CH$_3$)—O—CH$_2$—), thiodiester (—O—C(O)—S—), thionocarbamate (—O—C(O)(NH)—S—); siloxane (—O—Si(H)$_2$—O—); and N,N'-dimethylhydrazine (—CH$_2$—N(CH$_3$)—N(CH$_3$)—). Antisense compounds having non-phosphorus internucleoside linking groups are referred to as oligonucleosides. Modified internucleoside linkages, compared to natural phosphodiester linkages, can be used to alter, typically increase, nuclease resistance of the antisense compound. Internucleoside linkages having a chiral atom can be prepared racemic, chiral, or as a mixture. Representative chiral internucleoside linkages include, but are not limited to, alkylphosphonates and phosphorothioates. Methods of preparation of phosphorous-containing and non-phosphorous-containing linkages are well known to those skilled in the art.

As used herein the term "mimetic" refers to groups that are substituted for a sugar, a nucleobase, and/or internucleoside linkage. Generally, a mimetic is used in place of the sugar or sugar-internucleoside linkage combination, and the nucleobase is maintained for hybridization to a selected target. Representative examples of a sugar mimetic include, but are not limited to, cyclohexenyl or morpholino. Representative examples of a mimetic for a sugar-internucleoside linkage combination include, but are not limited to, peptide nucleic acids (PNA) and morpholino groups linked by uncharged achiral linkages. In some instances a mimetic is used in place of the nucleobase. Representative nucleobase mimetics are well known in the art and include, but are not limited to, tricyclic phenoxazine analogs and universal bases (Berger et al., Nuc Acid Res. 2000, 28:2911-14, incorporated herein by reference). Methods of synthesis of sugar, nucleoside and nucleobase mimetics are well known to those skilled in the art.

As used herein the term "nucleoside" includes, nucleosides, abasic nucleosides, modified nucleosides, and nucleosides having mimetic bases and/or sugar groups.

In the context of this invention, the term "oligonucleotide" refers to an oligomeric compound which is an oligomer or polymer of ribonucleic acid (RNA) or deoxyribonucleic acid (DNA). This term includes oligonucleotides composed of naturally- and non-naturally-occurring nucleobases, sugars and covalent internucleoside linkages, possibly further including non-nucleic acid conjugates.

The present invention provides compounds having reactive phosphorus groups useful for forming internucleoside linkages including for example phosphodiester and phosphorothioate internucleoside linkages. Methods of preparation and/or purification of precursors or antisense compounds of the instant invention are not a limitation of the compositions or methods of the invention. Methods for synthesis and purification of DNA, RNA, and the antisense compounds of the instant invention are well known to those skilled in the art.

As used herein the term "chimeric antisense compound" refers to an antisense compound, having at least one sugar, nucleobase and/or internucleoside linkage that is differentially modified as compared to the other sugars, nucleobases and internucleoside linkages within the same oligomeric compound. The remainder of the sugars, nucleobases and internucleoside linkages can be independently modified or unmodified. In general a chimeric oligomeric compound will have modified nucleosides that can be in isolated positions or grouped together in regions that will define a particular motif. Any combination of modifications and or mimetic groups can comprise a chimeric oligomeric compound of the present invention.

Chimeric oligomeric compounds typically contain at least one region modified so as to confer increased resistance to nuclease degradation, increased cellular uptake, and/or increased binding affinity for the target nucleic acid. An additional region of the oligomeric compound may serve as a substrate for enzymes capable of cleaving RNA:DNA or RNA:RNA hybrids. By way of example, RNase H is a cellular endonuclease that cleaves the RNA strand of an RNA:DNA duplex. Activation of RNase H, therefore, results in cleavage of the RNA target, thereby greatly enhancing the efficiency of inhibition of gene expression. Consequently, comparable results can often be obtained with shorter oligomeric compounds when chimeras are used, compared to for example phosphorothioate deoxyoligonucleotides hybridizing to the same target region. Cleavage of the RNA target can be routinely detected by gel electrophoresis and, if necessary, associated nucleic acid hybridization techniques known in the art.

Certain chimeric as well as non-chimeric oligomeric compounds can be further described as having a particular motif. As used in the present invention the term "motif" refers to the orientation of modified sugar moieties and/or sugar mimetic groups in an antisense compound relative to like or differentially modified or unmodified nucleosides. As used in the present invention, the terms "sugars", "sugar moieties" and "sugar mimetic groups' are used interchangeably. Such motifs include, but are not limited to, gapped motifs, alternating motifs, fully modified motifs, hemimer motifs, blockmer motifs, and positionally modified motifs. The sequence and the structure of the nucleobases and type of internucleoside linkage is not a factor in determining the motif of an antisense compound.

As used in the present invention the term "gapped motif" refers to an antisense compound comprising a contiguous sequence of nucleosides that is divided into 3 regions, an internal region (gap) flanked by two external regions (wings). The regions are differentiated from each other at least by having differentially modified sugar groups that comprise the nucleosides. In some embodiments, each modified region is uniformly modified (e.g. the modified sugar groups in a given region are identical); however, other motifs can be applied to regions. For example, the wings in a gapmer could have an alternating motif. The nucleosides located in the gap of a gapped antisense compound have sugar moieties that are different than the modified sugar moieties in each of the wings. In a preferred embodiment of the invention, the antisense compounds are 5-10-5 MOE gapmers having a 2'-MOE modifications on nucleobases 1-5 and 16-20, all cytosines are 5MeC, and a full phosphorothioate backbone.

As used in the present invention the term "alternating motif" refers to an antisense compound comprising a contiguous sequence of nucleosides comprising two differentially sugar modified nucleosides that alternate for essentially the entire sequence of the antisense compound, or for essentially the entire sequence of a region of an antisense compound.

As used in the present invention the term "fully modified motif" refers to an antisense compound comprising a contiguous sequence of nucleosides wherein essentially each nucleoside is a sugar modified nucleoside having uniform modification.

As used in the present invention the term "hemimer motif" refers to a sequence of nucleosides that have uniform sugar moieties (identical sugars, modified or unmodified) and wherein one of the 5'-end or the 3'-end has a sequence of from 2 to 12 nucleosides that are sugar modified nucleosides that are different from the other nucleosides in the hemimer modified antisense compound.

As used in the present invention the term "blockmer motif" refers to a sequence of nucleosides that have uniform sugars (identical sugars, modified or unmodified) that is internally interrupted by a block of sugar modified nucleosides that are uniformly modified and wherein the modification is different from the other nucleosides. Methods of preparation of chimeric oligonucleotide compounds are well known to those skilled in the art.

As used in the present invention the term "positionally modified motif" comprises all other motifs. Methods of preparation of positionally modified oligonucleotide compounds are well known to those skilled in the art.

The compounds described herein contain one or more asymmetric centers and thus give rise to enantiomers, diastereomers, and other stereoisomeric configurations that may be defined, in terms of absolute stereochemistry, as (R) or (S), α or β, or as (D) or (L) such as for amino acids et al. The present invention is meant to include all such possible isomers, as well as their racemic and optically pure forms.

In one aspect of the present invention antisense compounds are modified by covalent attachment of one or more conjugate groups. Conjugate groups may be attached by reversible or irreversible attachments. Conjugate groups may be attached directly to antisense compounds or by use of a linker. Linkers may be mono- or bifunctional linkers. Such attachment methods and linkers are well known to those skilled in the art. In general, conjugate groups are attached to antisense compounds to modify one or more properties. Such considerations are well known to those skilled in the art.

Oligomer Synthesis

Oligomerization of modified and unmodified nucleosides can be routinely performed according to literature procedures for DNA (Protocols for Oligonucleotides and Analogs, Ed. Agrawal (1993), Humana Press) and/or RNA (Scaringe, Methods (2001), 23, 206-217. Gait et al., Applications of Chemically synthesized RNA in RNA: Protein Interactions, Ed. Smith (1998), 1-36. Gallo et al., Tetrahedron (2001), 57, 5707-5713).

Antisense compounds of the present invention can be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives. The invention is not limited by the method of antisense compound synthesis.

Oligomer Purification and Analysis

Methods of oligonucleotide purification and analysis are known to those skilled in the art. Analysis methods include capillary electrophoresis (CE) and electrospray-mass spectroscopy. Such synthesis and analysis methods can be performed in multi-well plates. The method of the invention is not limited by the method of oligomer purification.

It should be appreciated that embodiments of the invention should not be construed to be limited to the examples, which are now described; rather, the invention should be construed to include any and all applications provided herein and all equivalent variations within the skill of the ordinary artisan.

IX. Rational Drug Design

FAM83A can be a therapeutic target in a variety of cancers. For example, FAM83A can be therapeutically targeted in any cancer selected from the group consisting of: melanoma, epithelial cancer, squamous cell cancer, small cell lung cancer, non-small cell lung cancer, glioma, hepatocellular (liver) carcinoma, thyroid tumor, a leukemia, gastric (stomach) cancer, prostate cancer, breast cancer, ovarian cancer, bladder cancer, lung cancer, glioblastoma, endometrial cancer, kidney cancer, colon cancer, ovarian cancer, hepatocellular cancer, pancreatic cancer, esophageal carcinoma, head and neck cancers, esophageal cancer, lymphoma, mesothelioma, sarcomas, carcinomas, biliary (cholangiocarcinoma), small bowel adenocarcinoma, pediatric malignancies and epidermoid carcinoma. Thus, several embodiments relate to rational drug design to target FAM83A.

Rational drug design involving polypeptides requires identifying and defining a first peptide with which the designed drug is to interact, and using the first target peptide to define the requirements for a second peptide. With such requirements defined, one can find or prepare an appropriate peptide or non-peptide that meets all or substantially all of the defined requirements. Thus, one goal of rational drug design is to produce structural or functional analogs of biologically active polypeptides of interest or of small molecules with which they interact (e.g., agonists, antagonists, null compounds) in order to fashion drugs that are, for example, more or less potent forms of the ligand. (See, e.g., Hodgson, *Bio. Technology* 9:19-21 (1991)). An example of rational drug design is shown in Erickson et al., *Science* 249:527-533 (1990). Combinatorial chemistry is the science of synthesizing and testing compounds for bioactivity en masse, instead of one by one, the aim being to discover drugs and materials more quickly and inexpensively than was formerly possible. Rational drug design and combinatorial chemistry have become more intimately related in recent years due to the development of approaches in computer-aided protein modeling and drug discovery. (See e.g., U.S. Pat. Nos. 4,908,773; 5,884,230; 5,873,052; 5,331,573; and 5,888,738).

The use of molecular modeling as a tool for rational drug design and combinatorial chemistry has dramatically increased due to the advent of computer graphics. In some embodiments, software is used to compare regions of FAM83A and molecules that interact with FAM83A (collectively referred to as "binding partners"—e.g., anti-FAM83A antibodies), and fragments or derivatives of these molecules with other molecules, such as peptides, peptidomimetics, and chemicals, so that therapeutic interactions can be predicted and designed. (See Schneider, *Genetic Engineering News* December: page 20 (1998), Tempczyk et al., *Molecular Simulations Inc. Solutions* April (1997) and Butenhof, *Molecular Simulations Inc. Case Notes* (August 1998) *for a discussion of molecular modeling*).

For example, the protein sequence of an FAM83A or binding partner, or domains of these molecules (or nucleic acid sequence encoding these polypeptides or both), can be entered onto a computer readable medium for recording and manipulation. It will be appreciated by those skilled in the art that a computer readable medium having these sequences can interface with software that converts or manipulates the sequences to obtain structural and functional information, such as protein models. That is, the functionality of a software program that converts or manipulates these sequences includes the ability to compare these sequences to other sequences or structures of molecules that are present on publicly and commercially available databases so as to conduct rational drug design.

The FAM83A or binding partner polypeptide or nucleic acid sequence or both can be stored, recorded, and manipulated on any medium that can be read and accessed by a computer. As used herein, the words "recorded" and "stored" refer to a process for storing information on computer readable medium. A skilled artisan can readily adopt any of the presently known methods for recording information on a computer readable medium to generate manufactures comprising the nucleotide or polypeptide sequence information of this embodiment.

As a starting point to rational drug design, a two or three dimensional model of a polypeptide of interest is created (e.g., FAM83A, or a binding partner). In the past, the three-dimensional structure of proteins has been determined in a number of ways. Perhaps the best known way of determining protein structure involves the use of x-ray crystallography. A general review of this technique can be found in Van Holde, K. E. Physical Biochemistry, Prentice-Hall, N.J. pp. 221-239 (1971). Using this technique, it is possible to elucidate three-dimensional structure with good precision. Additionally, protein structure can be determined through the use of techniques of neutron diffraction, or by nuclear magnetic resonance (NMR). (See, e.g., Moore, W. J., Physical Chemistry, $4^{th}$ Edition, Prentice-Hall, N.J. (1972)).

Alternatively, protein models of a polypeptide of interest can be constructed using computer-based protein modeling techniques. By one approach, the protein folding problem is solved by finding target sequences that are most compatible with profiles representing the structural environments of the residues in known three-dimensional protein structures. (See, e.g., U.S. Pat. No. 5,436,850). In another technique, the known three-dimensional structures of proteins in a given family are superimposed to define the structurally conserved regions in that family. This protein modeling technique also uses the known three-dimensional structure of a homologous protein to approximate the structure of a polypeptide of interest. (See e.g., U.S. Pat. Nos. 5,557,535; 5,884,230; and 5,873,052). Conventional homology modeling techniques have been used routinely to build models of proteases and antibodies. (Sowdhamini et al., *Protein Engineering* 10:207, 215 (1997)). Comparative approaches can also be used to develop three-dimensional protein models when the protein of interest has poor sequence identity to template proteins. In some cases, proteins fold into similar three-dimensional structures despite having very weak sequence identities. For example, the three-dimensional structures of a number of helical cytokines fold in similar three-dimensional topology in spite of weak sequence homology.

Additionally, the techniques described above can be supplemented with techniques in molecular biology to design models of the protein of interest. For example, a polypeptide of interest can be analyzed by an alanine scan (Wells, Methods in Enzymol. 202:390-411 (1991)) or other types of site-directed mutagenesis analysis.

Once a model of the polypeptide of interest is created, it can be compared to other models so as to identify new members of the FAM83A family and binding partners. By starting with the amino acid sequence or protein model of FAM83A or a binding partner, for example, molecules having two-dimensional and/or three-dimensional homology can be rapidly identified. In one approach, a percent sequence identity can be determined by standard methods that are commonly used to compare the similarity and position of the amino acid of two polypeptides. Using a computer program such as BLAST or FASTA, two polypeptides can be aligned for optimal matching of their respective amino acids (either along the full length of one or both sequences, or along a predetermined portion of one or both sequences).

Accordingly, the protein sequence corresponding to an FAM83A or a binding partner or a fragment or derivative of these molecules can be compared to known sequences on a protein basis. Protein sequences corresponding to an FAM83A, or a binding partner or a fragment or derivative of these molecules are compared, for example, to known amino acid sequences found in Swissprot release 35, PIR release 53 and Genpept release 108 public databases using BLASTP with the parameter W=8 and allowing a maximum of 10 matches. In addition, the protein sequences are compared to publicly known amino acid sequences of Swissprot using BLASTX with the parameter E=0.001. The molecules identified as members of the family of FAM83A or candidate binding partners desirably have at least 35% homology and preferably have 40%, 45%, 50% or 55% or greater homology to FAM83A.

In another embodiment, computer modeling and the sequence-to-structure-to-function paradigm is exploited to identify more members of the FAM83A family candidate binding partners. By this approach, first the structure of an FAM83A or a candidate binding partner having a known response in a characterization assay is determined from its sequence using a threading algorithm, which aligns the sequence to the best matching structure in a structural database. Next, the protein's active site (i.e., the site important for a desired response in the characterization assay) is identified and a "fuzzy functional form" (FFF)—a three-dimensional descriptor of the active site of a protein—is created. (See e.g., Fetrow et al., *J. Mol. Biol.* 282:703-711 (1998) and Fetrow and Skolnick, *J. Mol. Biol.* 281: 949-968 (1998).

By a similar approach, a candidate binding partner can be identified and manufactured as follows. First, a molecular model of one or more molecules that are known to interact with FAM83A or portions of these molecules that interact with an FAM83A are created using one of the techniques discussed above or as known in the art. Next, chemical libraries and databases are searched for molecules similar in structure to the known molecule. That is, a search can be made of a three dimensional data base for non-peptide (organic) structures (e.g., non-peptide analogs, and/or dipeptide analogs) having three dimensional similarity to the known structure of the target compound. See, e.g., the Cambridge Crystal Structure Data Base, Crystallographic Data Center, Lensfield Road, Cambridge, CB2 1EW, England; and Allen, F. H., et al., *Acta Crystallogr.*, B35: 2331-2339 (1979). The identified candidate binding partners that interact with FAM83A can then be analyzed in a functional assay and new molecules can be modeled after the candidate binding partners that produce a desirable response. By cycling in this fashion, libraries of molecules that interact with FAM83A and produce a desirable or optimal response in a functional assay can be selected.

By another approach, protein models of binding partners that interact with an FAM83A can be made by the methods described above and these models can be used to predict the interaction of new molecules. Once a model of a binding partner is identified, the active sites or regions of interaction can be identified. Such active sites might typically be ligand binding sites. The active site can be identified using methods known in the art including, for example, from the amino acid sequences of peptides, from the nucleotide sequences of nucleic acids, or from study of complexes of the FAM83A with a ligand. In the latter case, chemical or X-ray crystallographic methods can be used to find the active site by finding where on the FAM83A the complexed ligand is found (e.g. protein-protein module). Next, the three dimensional geometric structure of the active site is determined. This can be done by known methods, including X-ray crystallography, which can determine a complete molecular structure. On the other hand, solid or liquid phase NMR can be used to determine certain intra-molecular distances. Any other experimental method of structure determination can be used to obtain partial or complete geometric structures. The geometric structures can be measured with a complexed ligand, natural or artificial, which may increase the accuracy of the active site structure determined Finally, having determined the structure of the active site of the known binding partner, either experimentally, by modeling, or by a combination, candidate binding partners can be identified by searching databases containing compounds along with information on their molecular structure. Such a search seeks compounds having structures that match the determined active site structure and that interact with the groups defining the active site. Such a search can be manual, but is preferably computer assisted. One program that allows for such analysis is Insight II having the Ludi module. Further, the Ludi/ACD module allows a user access to over 65,000 commercially available drug candidates (MDL's Available Chemicals Directory) and provides the ability to screen these compounds for interactions with the protein of interest.

Alternatively, these methods can be used to identify improved binding partners from an already known binding partner. The composition of the known binding partner can be modified and the structural effects of modification can be determined using the experimental and computer modeling methods described above applied to the new composition. The altered structure is then compared to the active site structure of the compound to determine if an improved fit or interaction results. In this manner systematic variations in composition, such as by varying side groups, can be quickly evaluated to obtain modified modulating compounds or ligands of improved specificity or activity.

Once candidate binding partners have been identified, desirably, they are analyzed in a functional assay. Further cycles of modeling and functional assays can be employed to more narrowly define the parameters needed in a binding partner. Each binding partner and its response in a functional assay can be recorded on a computer readable media and a database or library of binding partners and respective responses in a functional assay can be generated. These databases or libraries can be used by researchers to identify important differences between active and inactive molecules so that compound libraries are enriched for binding partners that have favorable characteristics. The section below describes several FAM83A functional assays that can be used to characterize new FAM83A family members and candidate binding partners.

FAM83A Characterization Assays

The term "FAM83A characterization assay" or "FAM83A functional assay" or "functional assay" the results of which can be recorded as a value in a "FAM83A functional profile", include assays that directly or indirectly evaluate the presence of an FAM83A nucleic acid or protein in a cell and FAM83A activity, ability to interact with another molecule, and/or modulate activity.

Some functional assays involve binding assays that utilize multimeric agents. One form of multimeric agent concerns a manufacture comprising an FAM83A, hybrid, binding partner, or fragment thereof disposed on a support. These multimeric agents provide the FAM83A, hybrid, binding partner, or fragment thereof in such a form or in such a way that a sufficient affinity is achieved. A multimeric agent having an FAM83A, hybrid, or binding partner or fragment thereof is obtained by joining the desired polypeptide to a macromolecular support. A "support" can be a termed a carrier, a protein, a resin, a cell membrane, or any macromolecular structure used to join or immobilize such molecules. Solid supports include, but are not limited to, the walls of wells of a reaction tray, test tubes, polystyrene beads, magnetic beads, nitrocellulose strips, membranes, microparticles such as latex particles, animal cells, Duracyte®, artificial cells, and others. An FAM83A, hybrid, or binding partner or fragment thereof can also be joined to inorganic carriers, such as silicon oxide material (e.g., silica gel, zeolite, diatomaceous earth or aminated glass) by, for example, a covalent linkage through a hydroxy, carboxy or amino group and a reactive group on the carrier.

In several multimeric agents, the macromolecular support has a hydrophobic surface that interacts with a portion of the FAM83A, hybrid, or binding partner or fragment thereof by a hydrophobic non-covalent interaction. In some cases, the hydrophobic surface of the support is a polymer such as plastic or any other polymer in which hydrophobic groups have been linked such as polystyrene, polyethylene or polyvinyl. Additionally, an FAM83A, hybrid, or binding partner or fragment thereof can be covalently bound to carriers including proteins and oligo/polysaccharides (e.g. cellulose, starch, glycogen, chitosane or aminated sepharose). In these later multimeric agents, a reactive group on the molecule, such as a hydroxy or an amino group, is used to join to a reactive group on the carrier so as to create the covalent bond. Additional multimeric agents comprise a support that has other reactive groups that are chemically activated so as to attach the FAM83A, hybrid, or binding partner or fragment thereof. For example, cyanogen bromide activated matrices, epoxy activated matrices, thio and thiopropyl gels, nitrophenyl chloroformate and N-hydroxy succinimide chlorformate linkages, or oxirane acrylic supports are used. (Sigma).

Furthermore, in some embodiments, a liposome or lipid bilayer (natural or synthetic) is contemplated as a support and FAM83A, hybrids, or binding partners are attached to the membrane surface or are incorporated into the membrane by techniques in liposome engineering. By one approach, liposome multimeric supports comprise an FAM83A, hybrid, or binding partner that is exposed on the surface. A hydrophobic domain can be joined to the FAM83A, hybrid, or binding partner so as to facilitate the interaction with the membrane. Carriers for use in the body, (i.e. for prophylactic or therapeutic applications) are desirably physiological, non-toxic and preferably, non-immunoresponsive. Suitable carriers for use in the body include poly-L-lysine, poly-D, L-alanine, liposomes, and Chromosorb® (Johns-Manville Products, Denver Co.). Ligand conjugated Chromosorb® (Synsorb-Pk) has been tested in humans for the prevention of hemolytic-uremic syndrome and was reported as not presenting adverse reactions. (Armstrong et al. *J. Infectious Diseases* 171:1042-1045 (1995)). For some embodiments, a "naked" carrier (i.e., lacking an attached binding partner) that has the capacity to attach an FAM83A or binding partner in the body of a organism is administered. By this approach, a "prodrug-type" therapy is envisioned in which the naked carrier is administered separately from the FAM83A or binding partner and, once both are in the body of the organism, the carrier and the FAM83A or binding partner are assembled into a multimeric complex.

The insertion of linkers, such as linkers (e.g., "λ linkers" engineered to resemble the flexible regions of λ phage) of an appropriate length between the FAM83A, hybrid, or binding partner and the support are also contemplated so as to encourage greater flexibility of the FAM83A, hybrid, or binding partner and thereby overcome any steric hindrance that can be presented by the support. The determination of an appropriate length of linker that allows for an optimal cellular response or lack thereof, can be determined by screening the FAM83A, hybrids, or binding partners with varying linkers in the assays detailed in the present disclosure.

A composite support comprising more than one type of FAM83A, hybrid, or binding partner is also envisioned. A "composite support" can be a carrier, a resin, or any macromolecular structure used to attach or immobilize two or more different binding partners or FAM83A. In some embodiments, a liposome or lipid bilayer (natural or synthetic) is contemplated for use in constructing a composite support and FAM83A or binding partners are attached to the membrane surface or are incorporated into the membrane using techniques in liposome engineering.

As above, the insertion of linkers, such as λ linkers, of an appropriate length between the FAM83A or binding partner and the support is also contemplated so as to encourage greater flexibility in the molecule and thereby overcome any steric hindrance that can occur. The determination of an appropriate length of linker that allows for an optimal cellular response or lack thereof, can be determined by screening the FAM83A or binding partners with varying linkers in the assays detailed in the present disclosure.

In other Embodiments, the multimeric and composite supports discussed above can have attached multimerized FAM83A, hybrids, or binding partners so as to create a "multimerized-multimeric support" and a "multimerized-composite support", respectively. A multimerized ligand can, for example, be obtained by coupling two or more binding partners in tandem using conventional techniques in molecular biology. The multimerized form of the FAM83A, hybrid, or binding partner can be advantageous for many applications because of the ability to obtain an agent with a higher affinity for FAM83A, for example. The incorporation of linkers or spacers, such as flexible λ linkers, between the individual domains that make-up the multimerized agent can also be advantageous for some embodiments. The insertion of λ linkers of an appropriate length between protein binding domains, for example, can encourage greater flexibility in the molecule and can overcome steric hindrance. Similarly, the insertion of linkers between the multimerized binding partner or FAM83A or hybrid and the support can encourage greater flexibility and limit steric hindrance presented by the support. The determination of an appropriate length of linker can be determined by screening the FAM83A, hybrids, and binding partners with varying linkers in the assays detailed in this disclosure.

Thus, several approaches to identify agents that interact with an FAM83A, employ FAM83A or a fragment thereof joined to a support. Once the support-bound FAM83A is obtained, for example, candidate binding partners are contacted to the support-bound FAM83A and an association is determined directly (e.g., by using labeled binding partner) or indirectly (e.g., by using a labeled antibody directed to the binding partner). Candidate binding partners are identified as binding partners by virtue of the association with the support-bound FAM83A. The properties of the binding partners are analyzed and derivatives are made using rational drug design and combinatorial chemistry. Candidate binding partners can be obtained from random chemical or peptide libraries but, preferably, are rationally selected. For example, monoclonal antibodies that bind to an FAM83A can be created and the nucleic acids encoding the VH and VL domains of the antibodies can be sequenced. These sequences can then be used to synthesize peptides that bind to FAM83A. Further, peptidomimetics corresponding to these sequences can be created. These molecules can then be used as candidate binding partners.

Additionally, a cell based approach can be used characterize new FAM83A family members or FAM83A hybrids or to rapidly identify binding partners that interact with an FAM83A and, thereby, modulate activity. Preferably, molecules identified in the support-bound FAM83A assay described above are used in the cell based approach, however, randomly generated compounds can also be used.

Other FAM83A characterization assays take advantage of techniques in molecular biology that are employed to discover protein:protein interactions. One method that detects protein-protein interactions in vivo, the two-hybrid system, is described in detail for illustration only and not by way of limitation. Other similar assays that can be adapted to identify binding partners include:

the two-hybrid systems (Field & Song, Nature 340:245-246 (1989); Chien et al., Proc. Natl. Acad. Sci. USA 88:9578-9582 (1991); and Young K H, Biol. Reprod. 58:302-311 (1998), all references herein expressly incorporated by reference);

reverse two-hybrid system (Leanna & Hannink, Nucl. Acid Res. 24:3341-3347 (1996), herein incorporated by reference);

repressed transactivator system (Sadowski et al., U.S. Pat. No. 5,885,779), herein incorporated by reference);

phage display (Lowman H B, Annu. Rev. Biophys. Biomol. Struct. 26:401-424 (1997), herein incorporated by reference); and GST/HIS pull down assays, mutant operators (Granger et al., WO 98/01879) and the like (See also Mathis G., Clin. Chem. 41:139-147 (1995); Lam K. S. Anticancer Drug Res., 12:145-167 (1997); and Phizicky et al., Microbiol. Rev. 59:94-123 (1995), all references herein expressly incorporated by reference).

An adaptation of the system described by Chien et al., 1991, Proc. Natl. Acad. Sci. USA, 88:9578-9582, herein incorporated by reference), which is commercially available from Clontech (Palo Alto, Calif.) is as follows. Plasmids are constructed that encode two hybrid proteins: one plasmid consists of nucleotides encoding the DNA-binding domain of a transcription activator protein fused to a nucleotide sequence encoding an FAM83A or fragment thereof, and the other plasmid consists of nucleotides encoding the transcription activator protein's activation domain fused to a cDNA encoding an unknown protein that has been recombined into this plasmid as part of a cDNA library. The DNA-binding domain fusion plasmid and the cDNA library are transformed into a strain of the yeast Saccharomyces cerevisiae that contains a reporter gene (e.g., HBS or lacZ) whose regulatory region contains the transcription activator's binding site. Either hybrid protein alone cannot activate transcription of the reporter gene: the DNA-binding domain hybrid cannot because it does not provide activation function and the activation domain hybrid cannot because it cannot localize to the activator's binding sites. Interaction of the two hybrid proteins reconstitutes the functional activator protein and results in expression of the reporter gene, which is detected by an assay for the reporter gene product.

The two-hybrid system or related methodology can be used to screen activation domain libraries for proteins that interact with the "bait" gene product. By way of example, and not by way of limitation, FAM83A can be used as the bait gene product. Total genomic or cDNA sequences are fused to the DNA encoding an activation domain. This library and a plasmid encoding a hybrid of a bait gene encoding the FAM83A product fused to the DNA-binding domain are cotransformed into a yeast reporter strain, and the resulting transformants are screened for those that express the reporter gene. For example, and not by way of limitation, a bait gene sequence encoding an FAM83A can be cloned into a vector such that it is translationally fused to the DNA encoding the DNA-binding domain of the GAL4 protein. These colonies are purified and the library plasmids responsible for reporter gene expression are isolated. DNA sequencing is then used to identify the proteins encoded by the library plasmids.

A cDNA library of the cell line from which proteins that interact with bait FAM83A are to be detected can be made using methods routinely practiced in the art. According to the particular system described herein, for example, the cDNA fragments can be inserted into a vector such that they are translationally fused to the transcriptional activation domain of GAL4. This library can be co-transformed along with the bait FAM83A gene-GAL4 fusion plasmid into a yeast strain which contains a lacZ gene driven by a promoter which contains GAL4 activation sequence. A cDNA encoded protein, fused to GAL4 transcriptional activation domain that interacts with bait FAM83A gene product will reconstitute an active GAL4 protein and thereby drive expression of the lacZ gene. Colonies that express lacZ can be detected and the cDNA can then be purified from these strains, and used to produce and isolate the binding partner by techniques routinely practiced in the art.

Identification of Binding Agents

Further contemplated is the use of the polypeptides of the embodiments disclosed herein, or the polynucleotides encoding these polypeptides, to screen for molecules which modify the activities of the polypeptides of the embodiments disclosed herein. Such a method would include contacting the polypeptide of the embodiments disclosed herein with a selected compound(s) suspected of having antagonist or agonist activity, and assaying the activity of these polypeptides following binding.

Embodiments disclosed herein relate to screening therapeutic compounds by using the FAM83A polypeptides described herein in any of a variety of drug screening techniques. The polypeptide or fragment employed in such a test may be affixed to a solid support, expressed on a cell surface, free in solution, or located intracellularly. One method of drug screening utilizes eukaryotic or prokaryotic host cells which are stably transformed with recombinant nucleic acids expressing the polypeptide or fragment. Drugs are screened against such transformed cells in competitive binding assays. One may measure, for example, the formulation of complexes between the agent being tested and a polypeptide of the embodiments disclosed herein.

Thus, the embodiments disclosed herein provide methods of screening for drugs or any other agents which affect activities mediated by FAM83A polypeptides described herein. These methods comprise contacting such an agent with a polypeptide of the embodiments disclosed herein or a fragment thereof and assaying for the presence of a complex between the agent and the polypeptide or a fragment thereof, by methods well known in the art. In such a competitive binding assay, the agents to screen are typically labeled. Following incubation, free agent is separated from that present in bound form, and the amount of free or uncomplexed label is a measure of the ability of a particular agent to bind to the polypeptides of the embodiments disclosed herein.

Another technique for drug screening provides high throughput screening for compounds having suitable binding affinity to the polypeptides of the embodiments disclosed herein, and is described in great detail in European Patent Application 84/03564, published on Sep. 13, 1984, which is incorporated herein by reference herein. Briefly stated, large numbers of different small peptide test compounds are synthesized on a solid substrate, such as plastic pins or some other surface. The peptide test compounds are reacted with polypeptides of the embodiments disclosed herein and washed. Bound polypeptides are then detected by methods well known in the art. Purified polypeptides are coated directly onto plates for use in the aforementioned drug screening techniques. In addition, non-neutralizing antibodies may be used to capture the peptide and immobilize it on the solid support.

This embodiments disclosed herein also contemplates the use of competitive drug screening assays in which neutralizing antibodies capable of binding FAM83A polypeptides specifically compete with a test compound for binding to the polypeptides or fragments thereof. In this manner, the antibodies are used to detect the presence of any peptide which shares one or more antigenic epitopes with a polypeptide of the embodiments disclosed herein.

FAM83A polypeptides, immunogenic fragments, or oligopeptides thereof can be used for screening therapeutic drugs or compounds in a variety of drug screening techniques. The fragment employed in such a screening assay may be free in solution, affixed to a solid support, borne on a cell surface, or located intracellularly. The reduction or abolition of activity of the formation of binding complexes between the ion channel protein and the agent being tested can be measured. Thus, the embodiments disclosed herein provides a method for screening or assessing a plurality of compounds for their specific binding affinity with a FAM83A polypeptide, or a bindable peptide fragment, of this embodiments disclosed herein, comprising providing a plurality of compounds, combining the FAM83A polypeptide, or a bindable peptide fragment, with each of a plurality of compounds for a time sufficient to allow binding under suitable conditions and detecting binding of the FAM83A polypeptide or peptide to each of the plurality of test compounds, thereby identifying the compounds that specifically bind to the FAM83A polypeptide or peptide.

Methods of identifying compounds that modulate the activity of the FAM83A polypeptides are provided by the embodiments disclosed herein and comprise combining a potential or candidate compound or drug modulator of immunoglobulin biological activity with an FAM83A polypeptide or peptide and measuring an effect of the candidate compound or drug modulator on the biological activity of the FAM83A polypeptide or peptide. Such measurable effects include, for example, physical binding interaction.

Another method of identifying compounds that modulate the biological activity of the FAM83A polypeptides of the embodiments disclosed herein comprises combining a potential or candidate compound or drug modulator of a immunoglobulin biological activity with a host cell that expresses the FAM83A polypeptide and measuring an effect of the candidate compound or drug modulator on the biological activity of the FAM83A polypeptide. The host cell can also be capable of being induced to express the FAM83A polypeptide, e.g., via inducible expression. Physiological effects of a given modulator candidate on the FAM83A polypeptide can also be measured. Thus, cellular assays for particular immunoglobulin modulators may be either direct measurement or quantification of the physical biological activity of the FAM83A polypeptide, or they may be measurement or quantification of a physiological effect. Such methods preferably employ a FAM83A polypeptide as described herein, or an overexpressed recombinant FAM83A polypeptide in suitable host cells containing an expression vector as described herein, wherein the FAM83A polypeptide is expressed, overexpressed, or undergoes upregulated expression.

Another aspect of the embodiments disclosed herein relates to a method of screening for a compound that is capable of modulating the biological activity of a FAM83A polypeptide, comprising providing a host cell containing an expression vector harboring a nucleic acid sequence encoding a FAM83A polypeptide or fragment thereof determining the biological activity of the expressed FAM83A polypeptide or fragment in the absence of a modulator compound; contacting the cell with the modulator compound and determining the biological activity of the expressed FAM83A polypeptide or fragment in the presence of the modulator compound. In such a method, a difference between the activity of the FAM83A polypeptide or fragment in the presence of the modulator compound and in the absence of the modulator compound indicates a modulating effect of the compound.

Chemical Libraries and Drug Screening

Any chemical compound can be employed as a potential modulator or ligand in the assays according to the embodiments disclosed herein. Compounds tested as immunoglobulin modulators can be any small chemical compound, or biological entity (e.g., protein, sugar, nucleic acid, lipid). Test compounds will typically be small chemical molecules and peptides. Generally, the compounds used as potential modulators can be dissolved in aqueous or organic (e.g., DMSO-based) solutions. The assays are designed to screen large chemical libraries by automating the assay steps and providing compounds from any convenient source. Assays are typically run in parallel, for example, in microtiter formats on microtiter plates in robotic assays. There are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs, Switzerland), for example. Also, compounds may be synthesized by methods known in the art.

High throughput screening methodologies can be used for the detection of modulators of FAM83A polynucleotides. Such high throughput screening methods can involve providing a combinatorial chemical or peptide library containing a large number of potential therapeutic compounds (e.g., ligand or modulator compounds). Such combinatorial chemical libraries or ligand libraries are then screened in one or more assays to identify those library members (e.g., particular chemical species or subclasses) that display a desired characteristic activity. The compounds so identified can serve as conventional lead compounds, or can themselves be used as potential or actual therapeutics.

A combinatorial chemical library is a collection of diverse chemical compounds generated either by chemical synthesis or biological synthesis, by combining a number of chemical building blocks (i.e., reagents such as amino acids). As an example, a linear combinatorial library, e.g., a polypeptide or peptide library, is formed by combining a set of chemical building blocks in every possible way for a given compound length (i.e., the number of amino acids in a polypeptide or peptide compound). Millions of chemical compounds can be synthesized through such combinatorial mixing of chemical building blocks.

The preparation and screening of combinatorial chemical libraries is well known to those having skill in the pertinent art. Combinatorial libraries include, without limitation, peptide libraries (e.g. U.S. Pat. No. 5,010,175; Furka, 1991, Int. J. Pept. Prot. Res., 37:487-493; and Houghton et al., 1991, Nature, 354:84-88). Other chemistries for generating chemical diversity libraries can also be used. Nonlimiting examples of chemical diversity library chemistries include, peptides (PCT Publication No. WO 91/019735), encoded peptides (PCT Publication No. WO 93/20242), random bio-oligomers (PCT Publication No. WO 92/00091), benzodiazepines (U.S. Pat. No. 5,288,514), diversomers such as hydantoins, benzodiazepines and dipeptides (Hobbs et al., 1993, Proc. Natl. Acad. Sci. USA, 90:6909-6913), vinylogous polypeptides (Hagihara et al., 1992, J. Amer. Chem. Soc., 114:6568), nonpeptidal peptidomimetics with glucose scaffolding (Hirschmann et al., 1992, J. Amer. Chem. Soc., 114:9217-9218), analogous organic synthesis of small compound libraries (Chen et al., 1994, J. Amer. Chem. Soc., 116:2661), oligocarbamates (Cho et al., 1993, Science, 261:1303), and/or peptidyl phosphonates (Campbell et al., 1994, J. Org. Chem., 59:658), nucleic acid libraries (see Ausubel, Berger and Sambrook, all supra), peptide nucleic acid libraries (U.S. Pat. No. 5,539,083), antibody libraries (e.g., Vaughn et al., 1996, Nature Biotechnology, 14(3):309-314) and PCT/US96/10287), carbohydrate libraries (e.g., Liang et al., 1996, Science, 274-1520-1522) and U.S. Pat. No. 5,593,853), small organic molecule libraries (e.g., benzodiazepines, Baum C&EN, Jan. 18, 1993, page 33; and U.S. Pat. No. 5,288,514; isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; and the like).

Devices for the preparation of combinatorial libraries are commercially available (e.g., 357 MPS, 390 MPS, Advanced Chem Tech, Louisville Ky.; Symphony, Rainin, Woburn, Mass.; 433A Applied Biosystems, Foster City, Calif.; 9050 Plus, Millipore, Bedford, Mass.). In addition, a large number of combinatorial libraries are commercially available (e.g., ComGenex, Princeton, N.J.; Asinex, Moscow, Russia; Tripos, Inc., St. Louis, Mo.; ChemStar, Ltd., Moscow, Russia; 3D Pharmaceuticals, Exton, Pa.; Martek Biosciences, Columbia, Md., and the like).

One embodiment provides solid phase based in vitro assays in a high throughput format, where the cell or tissue expressing an ion channel is attached to a solid phase substrate. In such high throughput assays, it is possible to screen up to several thousand different modulators or ligands in a single day. In particular, each well of a microtiter plate can be used to perform a separate assay against a selected potential modulator, or, if concentration or incubation time effects are to be observed, every 5-10 wells can test a single modulator. Thus, a single standard microtiter plate can assay about 96 modulators. If 1536 well plates are used, then a single plate can easily assay from about 100 to about 1500 different compounds. It is possible to assay several different plates per day; thus, for example, assay screens for up to about 6,000-20,000 different compounds are possible using the described integrated systems.

Various embodiments disclosed herein relate to screening and small molecule (e.g., drug) detection assays which involve the detection or identification of small molecules that can bind to a FAM83A polypeptide or peptide. Particularly preferred are assays suitable for high throughput screening methodologies.

In such binding-based detection, identification, or screening assays, a functional assay is not typically required. All that is needed is a target protein, preferably substantially purified, and a library or panel of compounds (e.g., ligands, drugs, small molecules) or biological entities to be screened or assayed for binding to the protein target. Preferably, most small molecules that bind to the target protein will modulate activity in some manner, due to preferential, higher affinity binding to functional areas or sites on the protein.

Any method known in the art for selecting and synthesizing small molecule libraries for screening is contemplated for use various embodiments disclosed herein. Small molecules to be screened are advantageously collected in the form of a combinatorial library. For example, libraries of drug-like small molecules, such as beta-turn mimetic libraries and the like, may be purchased from for example ChemDiv, Pharmacopia or Combichem or synthesized and are described in Tietze and Lieb, Curr. Opin. Chem. Biol. 2:363-371, 1998; Carrell et al., Chem. Biol. 2:171-183, 1995; U.S. Pat. Nos. 5,880,972, 6,087,186 and 6,184,223, the disclosures of which are hereby incorporated by reference.

Any of these libraries known in the art are suitable for screening, as are random libraries or individual compounds. In general, hydrophilic compounds are preferred because they are more easily soluble, more easily synthesized, and more easily compounded. Compounds having an average molecular weight of about 500 often are most useful, however, compounds outside this range, or even far outside this range also may be used. Generally, compounds having c log P scores of about 5.0 are preferred, however the methods are useful with all types of compounds. Simple filters like Lipinski's "rule of five" have predictive value and may be used to improve the quality of leads discovered by this inventive strategy by using only those small molecules which are bioavailable. See Lipinski et al., Adv. Drug Delivery Rev. 23:3-25, 1997.

Combinatorial chemistry small molecule "libraries" can be screened against drug targets. These collections provide an excellent source of novel, readily available leads. For example, ChemDiv uses more than 800 individual chemical cores, a unique Building Block Library, and proprietary chemistry in designing its Diversity Collections (small molecule libraries) to assemble 80,000-100,000 compounds a year. CombiLab lead library sets of 200-400 compounds also can be produced as a follow-up. In addition, ChemDiv's compounds are designed to ensure their similarity to drugs adjusted according to proprietary algorithms of "drug-likeness definitions" (group similarity and advanced neural net approaches), and a variety of intelligent instruments for ADME&T (Absorption, Distribution, Metabolism, Excretion and Toxicity) properties prediction, such as partition coefficient, solubility, dissociation coefficients, and acute toxicity.

Directed synthesis of new small molecule libraries can provide a variety of compounds structurally related to the initial lead compound which may be screened to choose optimal structures. Preferably, a library of compounds is selected that are predicted to be "drug-like" based on properties such as pKa, log P, size, hydrogen bonding and polarity. The inventive multi-step approach which yields high affinity peptides in the first step, and small molecules in a subsequent step reduces the number of artificial hits by eliminating the lower affinity small molecules that would be selected and have to be assayed in a normal high throughput screening method.

To purify a FAM83A polypeptide or peptide to measure a biological binding or ligand binding activity, the source may be a whole cell lysate that can be prepared by successive freeze-thaw cycles (e.g., one to three) in the presence of standard protease inhibitors. The FAM83A polypeptide may be partially or completely purified by standard protein purification methods, e.g., affinity chromatography using specific antibody described infra, or by ligands specific for an epitope tag engineered into the recombinant FAM83A polypeptide molecule, also as described herein. Binding activity can then be measured as described.

Various embodiments relate to compounds that are identified according to the methods described herein, and which modulate or regulate the biological activity or physiology of FAM83A polypeptides. It is contemplated that such modulatory compounds may be employed in treatment and therapeutic methods for treating a condition that is associated with the novel FAM83A polypeptides by administering to a subject in need of such treatment a therapeutically effective amount of the compound identified by the methods described herein.

The examples provided herein give those of ordinary skill in the art a disclosure and description of how to make and use the preferred embodiments, and are not intended to limit the scope of what the inventors regard as their invention. Modifications of the above-described modes for carrying out the described embodiments that are obvious to persons of skill in the art are intended to be within the scope of the following claims.

X. Formulation and Administration of Fam83A Inhibitors

The terms "pharmaceutically acceptable salts" and "a pharmaceutically acceptable salt thereof" as used herein are broad terms, and are to be given their ordinary and customary meaning to a person of ordinary skill in the art (and are not to be limited to a special or customized meaning), and refer without limitation to salts prepared from pharmaceutically acceptable, non-toxic acids or bases. Suitable pharmaceutically acceptable salts include metallic salts, e.g., salts of aluminum, zinc, alkali metal salts such as lithium, sodium, and potassium salts, alkaline earth metal salts such as calcium and magnesium salts; organic salts, e.g., salts of lysine, N,N'-dibenzylethylenediamine, chloroprocaine, choline, diethanolamine, ethylenediamine, meglumine (N-methylglucamine), procaine, and tris; salts of free acids and bases; inorganic salts, e.g., sulfate, hydrochloride, and hydrobromide; and other salts which are currently in widespread pharmaceutical use and are listed in sources well known to those of skill in the art, such as, for example, The Merck Index. Any suitable constituent can be selected to make a salt of the therapeutic agents discussed herein, provided that it is non-toxic and does not substantially interfere with the desired activity. In addition to salts, pharmaceutically acceptable precursors and derivatives of the compounds can be employed. Pharmaceutically acceptable amides, lower alkyl esters, and protected derivatives can also be suitable for use in compositions and methods of preferred embodiments. While it may be possible to administer the compounds of the preferred embodiments in the form of pharmaceutically acceptable salts, it is generally preferred to administer the compounds in neutral form.

It is generally preferred to administer the compounds of preferred embodiments in an intravenous or subcutaneous unit dosage form; however, other routes of administration are also contemplated. Contemplated routes of administration include but are not limited to oral, parenteral, intravenous, and subcutaneous. The compounds of preferred embodiments can be formulated into liquid preparations for, e.g., oral administration. Suitable forms include suspensions, syrups, elixirs, and the like. Particularly preferred unit dosage forms for oral administration include tablets and capsules. Unit dosage forms configured for administration once a day are particularly preferred; however, in certain embodiments it can be desirable to configure the unit dosage form for administration twice a day, or more.

The pharmaceutical compositions of preferred embodiments are preferably isotonic with the blood or other body fluid of the recipient. The isotonicity of the compositions can be attained using sodium tartrate, propylene glycol or other inorganic or organic solutes. Sodium chloride is particularly preferred. Buffering agents can be employed, such as acetic acid and salts, citric acid and salts, boric acid and salts, and phosphoric acid and salts. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. In certain embodiments it can be desirable to maintain the active compound in the reduced state. Accordingly, it can be desirable to include a reducing agent, such as vitamin C, vitamin E, or other reducing agents as are known in the pharmaceutical arts, in the formulation.

Viscosity of the pharmaceutical compositions can be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the thickening agent selected. An amount is preferably used that will achieve the selected viscosity. Viscous compositions are normally prepared from solutions by the addition of such thickening agents.

A pharmaceutically acceptable preservative can be employed to increase the shelf life of the pharmaceutical compositions. Benzyl alcohol can be suitable, although a variety of preservatives including, for example, parabens, thimerosal, chlorobutanol, or benzalkonium chloride can also be employed. A suitable concentration of the preservative is typically from about 0.02% to about 2% based on the total weight of the composition, although larger or smaller amounts can be desirable depending upon the agent selected. Reducing agents, as described above, can be advantageously used to maintain good shelf life of the formulation.

The compounds of preferred embodiments can be in admixture with a suitable carrier, diluent, or excipient such as sterile water, physiological saline, glucose, or the like, and can contain auxiliary substances such as wetting or emulsifying agents, pH buffering agents, gelling or viscosity enhancing additives, preservatives, flavoring agents, colors, and the like, depending upon the route of administration and the preparation desired. See, e.g., "Remington: The Science and Practice of Pharmacy", Lippincott Williams & Wilkins; 20th edition (Jun. 1, 2003) and "Remington's Pharmaceutical Sciences," Mack Pub. Co.; 18th and 19th editions (December 1985, and June 1990, respectively). Such preparations can include complexing agents, metal ions, polymeric compounds such as polyacetic acid, polyglycolic acid, hydrogels, dextran, and the like, liposomes, microemulsions, micelles, unilamellar or multilamellar vesicles, erythrocyte ghosts or spheroblasts. Suitable lipids for liposomal formulation include, without limitation, monoglycerides, diglycerides, sulfatides, lysolecithin, phospholipids, saponin, bile acids, and the like. The presence of such additional components can influence the physical state, solubility, stability, rate of in vivo release, and rate of in vivo clearance, and are thus chosen according to the intended application, such that the characteristics of the carrier are tailored to the selected route of administration.

For oral administration, the pharmaceutical compositions can be provided as a tablet, aqueous or oil suspension, dispersible powder or granule, emulsion, hard or soft capsule, syrup or elixir. Compositions intended for oral use can be prepared according to any method known in the art for the manufacture of pharmaceutical compositions and can include one or more of the following agents: sweeteners, flavoring agents, coloring agents and preservatives. Aqueous suspensions can contain the active ingredient in admixture with excipients suitable for the manufacture of aqueous suspensions.

Formulations for oral use can also be provided as hard gelatin capsules, wherein the active ingredient(s) are mixed with an inert solid diluent, such as calcium carbonate, calcium phosphate, or kaolin, or as soft gelatin capsules. In soft capsules, the active compounds can be dissolved or suspended in suitable liquids, such as water or an oil medium, such as peanut oil, olive oil, fatty oils, liquid paraffin, or liquid polyethylene glycols. Stabilizers and microspheres formulated for oral administration can also be used. Capsules can include push-fit capsules made of gelatin, as well as soft, sealed capsules made of gelatin and a plasticizer, such as glycerol or sorbitol. The push-fit capsules can contain the active ingredient in admixture with fillers such as lactose, binders such as starches, and/or lubricants such as talc or magnesium stearate and, optionally, stabilizers. In instances where it is desirable to maintain a compound of a preferred embodiment in a reduced form (in the case of certain active metabolites), it can be desirable to include a reducing agent in the capsule or other dosage form.

Tablets can be uncoated or coated by known methods to delay disintegration and absorption in the gastrointestinal tract and thereby provide a sustained action over a longer period of time. For example, a time delay material such as glyceryl monostearate can be used. When administered in solid form, such as tablet form, the solid form typically comprises from about 0.001 wt. % or less to about 50 wt. % or more of active ingredient(s), preferably from about 0.005, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, or 1 wt. % to about 2, 3, 4, 5, 6, 7, 8, 9, 10, 15, 20, 25, 30, 35, 40, or 45 wt. %.

Tablets can contain the active ingredients in admixture with non-toxic pharmaceutically acceptable excipients including inert materials. For example, a tablet can be prepared by compression or molding, optionally, with one or more additional ingredients. Compressed tablets can be prepared by compressing in a suitable machine the active ingredients in a free-flowing form such as powder or granules, optionally mixed with a binder, lubricant, inert diluent, surface active or dispersing agent. Molded tablets can be made by molding, in a suitable machine, a mixture of the powdered compound moistened with an inert liquid diluent.

Preferably, each tablet or capsule contains from about 10 mg or less to about 1,000 mg or more of a compound of the preferred embodiments, more preferably from about 20, 30, 40, 50, 60, 70, 80, 90, or 100 mg to about 150, 200, 250, 300, 350, 400, 450, 500, 550, 600, 650, 700, 750, 800, or 900 mg. Most preferably, tablets or capsules are provided in a range of dosages to permit divided dosages to be administered. A dosage appropriate to the patient and the number of doses to be administered daily can thus be conveniently selected. In certain embodiments it can be preferred to incorporate two or more of the therapeutic agents to be administered into a single tablet or other dosage form (e.g., in a combination therapy); however, in other embodiments it can be preferred to provide the therapeutic agents in separate dosage forms.

Suitable inert materials include diluents, such as carbohydrates, mannitol, lactose, anhydrous lactose, cellulose, sucrose, modified dextrans, starch, and the like, or inorganic salts such as calcium triphosphate, calcium phosphate, sodium phosphate, calcium carbonate, sodium carbonate, magnesium carbonate, and sodium chloride. Disintegrants or granulating agents can be included in the formulation, for example, starches such as corn starch, alginic acid, sodium starch glycolate, Amberlite, sodium carboxymethylcellulose, ultramylopectin, sodium alginate, gelatin, orange peel, acid carboxymethyl cellulose, natural sponge and bentonite, insoluble cationic exchange resins, powdered gums such as agar, karaya or tragacanth, or alginic acid or salts thereof.

Binders can be used to form a hard tablet. Binders include materials from natural products such as acacia, tragacanth, starch and gelatin, methyl cellulose, ethyl cellulose, carboxymethyl cellulose, polyvinyl pyrrolidone, hydroxypropylmethyl cellulose, and the like.

Lubricants, such as stearic acid or magnesium or calcium salts thereof, polytetrafluoroethylene, liquid paraffin, vegetable oils and waxes, sodium lauryl sulfate, magnesium lauryl sulfate, polyethylene glycol, starch, talc, pyrogenic silica, hydrated silicoaluminate, and the like, can be included in tablet formulations.

Surfactants can also be employed, for example, anionic detergents such as sodium lauryl sulfate, dioctyl sodium sulfosuccinate and dioctyl sodium sulfonate, cationic such as benzalkonium chloride or benzethonium chloride, or non-ionic detergents such as polyoxyethylene hydrogenated castor oil, glycerol monostearate, polysorbates, sucrose fatty acid ester, methyl cellulose, or carboxymethyl cellulose.

Controlled release formulations can be employed wherein the amifostine or analog(s) thereof is incorporated into an inert matrix that permits release by either diffusion or leaching mechanisms. Slowly degenerating matrices can also be incorporated into the formulation. Other delivery systems can include timed release, delayed release, or sustained release delivery systems.

Coatings can be used, for example, nonenteric materials such as methyl cellulose, ethyl cellulose, hydroxyethyl cellulose, methylhydroxy-ethyl cellulose, hydroxypropyl cellulose, hydroxypropyl-methyl cellulose, sodium carboxy-methyl cellulose, providone and the polyethylene glycols, or enteric materials such as phthalic acid esters. Dyestuffs or pigments can be added for identification or to characterize different combinations of active compound doses When administered orally in liquid form, a liquid carrier such as water, petroleum, oils of animal or plant origin such as peanut oil, mineral oil, soybean oil, or sesame oil, or synthetic oils can be added to the active ingredient(s). Physiological saline solution, dextrose, or other saccharide solution, or glycols such as ethylene glycol, propylene glycol, or polyethylene glycol are also suitable liquid carriers. The pharmaceutical compositions can also be in the form of oil-in-water emulsions. The oily phase can be a vegetable oil, such as olive or arachis oil, a mineral oil such as liquid paraffin, or a mixture thereof. Suitable emulsifying agents include naturally-occurring gums such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsions can also contain sweetening and flavoring agents.

When a compound of the preferred embodiments is administered by intravenous, parenteral, or other injection, it is preferably in the form of a pyrogen-free, parenterally acceptable aqueous solution or oleaginous suspension. Suspensions can be formulated according to methods well known in the art using suitable dispersing or wetting agents and suspending agents. The preparation of acceptable aqueous solutions with suitable pH, isotonicity, stability, and the like, is within the skill in the art. A preferred pharmaceutical composition for injection preferably contains an isotonic vehicle such as 1,3-butanediol, water, isotonic sodium chloride solution, Ringer's solution, dextrose solution, dextrose and sodium chloride solution, lactated Ringer's solution, or other vehicles as are known in the art. In addition, sterile fixed oils can be employed conventionally as a solvent or suspending medium. For this purpose, any bland fixed oil can be employed including synthetic mono or diglycerides. In addition, fatty acids such as oleic acid can likewise be used in the formation of injectable preparations. The pharmaceutical compositions can also contain stabilizers, preservatives, buffers, antioxidants, or other additives known to those of skill in the art.

The duration of the injection can be adjusted depending upon various factors, and can comprise a single injection administered over the course of a few seconds or less, to 0.5, 0.1, 0.25, 0.5, 0.75, 1, 2, 3, 4, 5, 6, 7, 8, 9, 10, 11, 12, 13, 14, 15, 16, 17, 18, 19, 20, 21, 22, 23, or 24 hours or more of continuous intravenous administration.

The compounds of the preferred embodiments can be provided to an administering physician or other health care professional in the form of a kit. The kit is a package which houses a container which contains the compound(s) in a suitable pharmaceutical composition, and instructions for administering the pharmaceutical composition to a subject. The kit can optionally also contain one or more additional therapeutic agents, e.g., a chemotherapeutic agent. For example, a kit containing one or more compositions comprising compound(s) of the preferred embodiments in combination with one or more additional antiretroviral, antibacterial, anti-neoplastic, and/or anti-infective agents can be provided, or separate pharmaceutical compositions containing a compound of the preferred embodiments and additional therapeutic agents can be provided. The kit can also contain separate doses of a compound of the preferred embodiments for serial or sequential administration. The kit can optionally contain one or more diagnostic tools and instructions for use. The kit can contain suitable delivery devices, e.g., syringes, and the like, along with instructions for administering the compound(s) and any other therapeutic agent. The kit can optionally contain instructions for storage, reconstitution (if applicable), and administration of any or all therapeutic agents included. The kits can include a plurality of containers reflecting the number of administrations to be given to a subject.

The preferred embodiments provide one or more compounds of the preferred embodiments for use as a pharmaceutical; or the use of one or more compounds of the preferred embodiments as a pharmaceutical (e.g., for the treatment of disorders which are mediated by FAM83A activity). For pharmaceutical use, one or more compounds of the preferred embodiments can be used, e.g., one, or a combination of two or more compounds of the preferred embodiments; however, preferably one compound is used. The compounds of preferred embodiments can be used as a pharmaceutical in the form of a pharmaceutical composition.

The FAM83A inhibitors can be employed therapeutically in compositions formulated for administration by any conventional route, including enterally (e.g., buccal, oral, nasal, rectal), parenterally (e.g., intravenous, intracranial, intraperitoneal, subcutaneous, or intramuscular), or topically (e.g., epicutaneous, intranasal, or intratracheal). Within other embodiments, the compositions described herein may be administered as part of a sustained release implant.

Within yet other embodiments, compositions of preferred embodiments may be formulized as a lyophilizate, utilizing appropriate excipients that provide stability as a lyophilizate, and subsequent to rehydration.

Pharmaceutical compositions containing the FAM83A inhibitors of preferred embodiments can be manufactured according to conventional methods, e.g., by mixing, granulating, coating, dissolving or lyophilizing processes.

In another embodiment, pharmaceutical compositions containing one or more FAM83A inhibitors are provided. For the purposes of administration, the compounds of preferred embodiments may be formulated as pharmaceutical compositions. Pharmaceutical compositions of preferred embodiments comprise one or more FAM83A inhibitors of preferred embodiments and a pharmaceutically acceptable carrier and/or diluent.

The FAM83A inhibitor is preferably employed in pharmaceutical compositions in an amount which is effective to treat a particular disorder, that is, in an amount sufficient to achieve decreased FAM83A levels or activity, symptoms, and/or preferably with acceptable toxicity to the patient. For such treatment, the appropriate dosage will, of course, vary depending upon, for example, the chemical nature and the pharmacokinetic data of a compound of the present invention used, the individual host, the mode of administration and the nature and severity of the conditions being treated. However, in general, for satisfactory results in larger mammals, for example humans, an indicated daily dosage is preferably from about 0.001 g to about 1.5 g, more preferably from about 0.01 g to 1.0 g; or from about 0.01 mg/kg body weight to about 20 mg/kg body weight, more preferably from about 0.1 mg/kg body weight to about 10 mg/kg body weight, for example, administered in divided doses up to four times a day. The compounds of preferred embodiments can be administered to larger mammals, for example humans, by similar modes of administration at similar dosages than conventionally used with other mediators, e.g., low molecular weight inhibitors, of FAM83A activity.

In certain embodiments, the pharmaceutical compositions of preferred embodiments can include FAM83A inhibitor(s) in an amount of about 0.5 mg or less to about 1500 mg or more per unit dosage form depending upon the route of administration, preferably from about 0.5, 0.6, 0.7, 0.8, or 0.9 mg to about 150, 200, 250, 300, 350, 400, 450, 500, 600, 700, 800, 900, or 1000 mg, and more preferably from about 1, 2, 3, 4, 5, 6, 7, 8, 9, 10, 15, 20, or 25 mg to about 30, 35, 40, 45, 50, 55, 60, 65, 70, 75, 80, 85, 90, 95, or 100 mg. In certain embodiments, however, lower or higher dosages than those mentioned above may be preferred. Appropriate concentrations and dosages can be readily determined by one skilled in the art.

Pharmaceutically acceptable carriers and/or diluents are familiar to those skilled in the art. For compositions formulated as liquid solutions, acceptable carriers and/or diluents include saline and sterile water, and may optionally include antioxidants, buffers, bacteriostats, and other common additives. The compositions can also be formulated as pills, capsules, granules, tablets (coated or uncoated), (injectable) solutions, solid solutions, suspensions, dispersions, solid dispersions (e.g., in the form of ampoules, vials, creams, gels, pastes, inhaler powder, foams, tinctures, lipsticks, drops, sprays, or suppositories). The formulation can contain (in addition to one or more FAM83A inhibitors and other optional active ingredients) carriers, fillers, disintegrators, flow conditioners, sugars and sweeteners, fragrances, preservatives, stabilizers, wetting agents, emulsifiers, solubilizers, salts for regulating osmotic pressure, buffers, diluents, dispersing and surface-active agents, binders, lubricants, and/or other pharmaceutical excipients as are known in the art. One skilled in this art may further formulate the FAM83A in an appropriate manner, and in accordance with accepted practices, such as those described in Remington's Pharmaceutical Sciences, Gennaro, Ed., Mack Publishing Co., Easton, Pa. 1990.

The compounds of preferred embodiments, including compounds of formula I, formula Ip, or other formulae above can include isomers, racemates, optical isomers, enantiomers, diastereomers, tautomers, and cis/trans conformers. All such isomeric forms are included within preferred embodiments, including mixtures thereof. The compounds of preferred embodiments may have chiral centers, for example, they may contain asymmetric carbon atoms and may thus exist in the form of enantiomers or diastereoisomers and mixtures thereof, e.g., racemates. Asymmetric carbon atom(s) can be present in the (R)-, (S)-, or (R,S)-configuration, preferably in the (R)- or (S)-configuration, or can be present as mixtures. Isomeric mixtures can be separated, as desired, according to conventional methods to obtain pure isomers. The compounds of preferred embodiments, e.g., formula I, can also include tautomers, where such tautomers can exist.

Furthermore, some of the crystalline forms of the compounds of preferred embodiments can exist as polymorphs, which are included in preferred embodiments. In addition, some of the compounds of preferred embodiments may also form solvates with water or other organic solvents. Such solvates are similarly included within the scope of the preferred embodiments.

In another embodiment, a method is provided for treating a variety of disorders or illnesses as described herein. Such methods include administering of a compound of preferred embodiments to a patient in an amount sufficient to treat the disorder or illness. Such methods include systemic administration of a FAM83A inhibitor of preferred embodiments, preferably in the form of a pharmaceutical composition. As used herein, systemic administration includes oral and parenteral methods of administration. For oral administration, suitable pharmaceutical compositions of an FAM83A inhibitor include powders, granules, pills, tablets, and capsules as well as liquids, syrups, suspensions, and emulsions. These compositions may also include flavorants, preservatives, suspending, thickening, and emulsifying agents, and other pharmaceutically acceptable additives. For parental administration, the compounds of preferred embodiments can be prepared in aqueous injection solutions that may contain, in addition to the FAM83A inhibitor, buffers, antioxidants, bacteriostats, and other additives commonly employed in such solutions.

As mentioned above, administration of a compound of preferred embodiments can be employed to treat a wide variety of disorders or illnesses. In particular, the compounds of preferred embodiments may be administered to a patient for the treatment of diseases and disorders as described above.

FAM83A inhibitors can be used alone, or in combination therapies with one, two, or more other pharmaceutical compounds or drug substances, and/or with one or more pharmaceutically acceptable excipient. The compounds of preferred embodiments and the additional pharmaceutical compounds or drug substances can be present in the same unit dosage form, or in two or more separate dosage forms. A method for treating disorders mediated by of FAM83A activity in a subject in need thereof is provided, comprising co-administering, concomitantly or in sequence, a therapeutically effective amount of a compound of the present invention and at least one second drug substance, e.g., in the form of a pharmaceutical combination or composition. Also provided is a compound of the preferred embodiments in combination with at least one second drug substance, e.g., in the form of a pharmaceutical combination or composition, for use in the preparation of a medicament for use in disorders mediated by FAM83A activity.

In preferred embodiments, the FAM83A inhibitor is present in combination with conventional drugs used to treat diseases or conditions wherein FAM83A is pathogenic or wherein FAM83A plays a pivotal or other role in the disease process. In particularly preferred embodiments, pharmaceutical compositions are provided comprising one or more FAM83A inhibitors, including, but not limited to compounds of the preferred embodiments in combination with one or more additional pharmaceutical compounds, including, but not limited to drugs for the treatment of various cancers. For example, FAM83A inhibitors may be used alone, or together with any number of EGFR tyrosine kinase inhibitor(s). Several embodiments relate to combination therapies including one or more FAM83A inhibitors and any combination of one or more of AG1478, gefitinib, and/or lapatinib. In one embodiment, a FAM83A inhibitor may be combined with AG1478. In another embodiment, a FAM83A inhibitor may be combined with gefitinib. In another embodiment, a FAM83A inhibitor may be combined with lapatinib. In another embodiment, a FAM83A inhibitor may be combined with AG1478 and gefitinib. In another embodiment, a FAM83A inhibitor may be combined with AG1478 and lapatinib. In another embodiment, a FAM83A inhibitor may be combined with gefitinib and lapatinib. It will be understood that these combinations including a FAM83A inhibitor and one or more of AG1478, gefitinib, and lapatinib may be co-administered, concomitantly or in any sequence. The FAM83A inhibitor in these various combinations may be effective for treating or restoring sensitivity of cancer cells resistant to AG1478, gefitinib, and/or lapatinib.

Combination therapies can include fixed combinations, in which two or more pharmaceutically active agents are in the same formulation; kits, in which two or more pharmaceutically active agents in separate formulations are sold in the same package, e.g., with instructions for co-administration; and free combinations in which the pharmaceutically active agents are packaged separately, but instruction for simultaneous or sequential administration are provided. Other kit components can include diagnostics, assays, multiple dosage forms for sequential or simultaneous administration, instructions and materials for reconstituting a lyophilized or concentrated form of the pharmaceutical composition, apparatus for administering the pharmaceutically active agents, and the like. For example, a pharmaceutical package is provided comprising a first drug substance which is a compound of the preferred embodiments and at least one second drug substance, along with instructions for combined administration. A pharmaceutical package is also provided comprising a compound of the preferred embodiments along with instructions for combined administration with at least one second drug substance. Also provided is a pharmaceutical package comprising at least one second drug substance along with instructions for combined administration with a compound of the present invention.

Treatment with combinations according to the preferred embodiments may provide improvements or superior outcome compared with treatments by either component of the combination alone. For example, a pharmaceutical combination comprising an amount of a compound of the preferred embodiments and an amount of a second drug substance can be employed, wherein the amounts are appropriate to produce a synergistic therapeutic effect. A method for improving the therapeutic utility of a compound of the preferred embodiments is also provided, comprising co-administering, e.g., concomitantly or in sequence, a therapeutically effective amount of a compound of the preferred embodiments and a second drug substance. A method for improving the therapeutic utility of a second drug substance is also provided comprising co-administering, e.g., concomitantly or in sequence, a therapeutically effective amount of a compound of the preferred embodiments and a second drug substance. A combination of the present invention and a second drug substance as a combination partner can be administered by any conventional route, for example as set out above for a compound of the preferred embodiments. A second drug can be administered in dosages as appropriate, e.g., in dosage ranges which are similar to those used for single treatment, or, e.g., in case of synergy, even below conventional dosage ranges.

Suitable second drug substances include chemotherapeutic drugs, especially any chemotherapeutic agent other than the FAM83A inhibitors of preferred embodiments. Such second drug substances can include, e.g., anti-inflammatory and/or immunomodulatory drugs, anticancer drugs, and the like.

These compounds of preferred embodiments can generally be employed as the free acid or the free base. Alternatively, the compounds of preferred embodiments can preferably be in the form of acid or base addition salts. The term "pharmaceutically acceptable salt" of compounds of the preferred embodiments is intended to encompass any and all acceptable salt forms. While salt forms of the preferred embodiments are preferably pharmaceutically acceptable salts, in certain embodiments pharmaceutically unacceptable salts can be employed (e.g., for preparation, isolation, and/or purification purposes). The compounds of preferred embodiments can also be employed in the form of a solvate, or in various combinations of forms (free acid, free base, salt, and/or solvate). A compound of the preferred embodiments in free form can be converted into a corresponding compound in the form of a salt; and vice versa. A solvate of a compound of preferred embodiments in free form or in the form of a salt can be converted into a corresponding non-solvate form of the compound in free form or in the form of a salt; and vice versa.

EXAMPLES

Example 1

Construction of Retroviral cDNA Library from Human Breast Cancer HMT3522 T4-2 Cell Line A retroviral cDNA library was generated using the pESY-NeoII vector system. The pESY-NeoII vector is a modified version of the pEYK3.1 vector. The pEYK3.1 vector was modified by subcloning a Neomycin resistance gene for ease of selection of clone and multi-cloning sites to allow directional cloning of cDNA inserts.

To construct the retroviral library, cDNA was prepared from T4-2 cells, size-fractionated and subcloned into the modified retroviral vector, pESY-NeoII. The complexity of the library was estimated by counting the number of colonies of transformed *E. coli* on the plates using an auto count program of phosphoimager, and the representation and average insert size was assessed by PCR using primers to flanking sequences of the cloning vector. The resulting retroviral cDNA library consists of a complexity of approximately $5\times10^4$ independent colonies and an average insert size of 1.2 kb. The average insert size detected by PCR is consistent with the size found by restriction enzyme digestion of mini-prep DNA of random colonies. The retroviruses bearing each cDNA in the library were produced in the *Phoenix* amphotropic retrovirus packaging cell line for subsequent transduction into HMT3422 T4-2 cells for phenotypic screening.

Example 2

Phenotypic Screening for Identification of Candidate Genes Responsible for Mediating Breast Cancer Cell Reversion FIG. 1 illustrates the experimental procedure of phenotypic screening to identify candidate genes responsible for mediating breast cancer cell reversion. To discover new genes that regulate this phenotypic reversion of human breast cancer cell to non-malignant phenotype, a functional screen was performed as illustrated in FIG. 1.

Figure 2A:
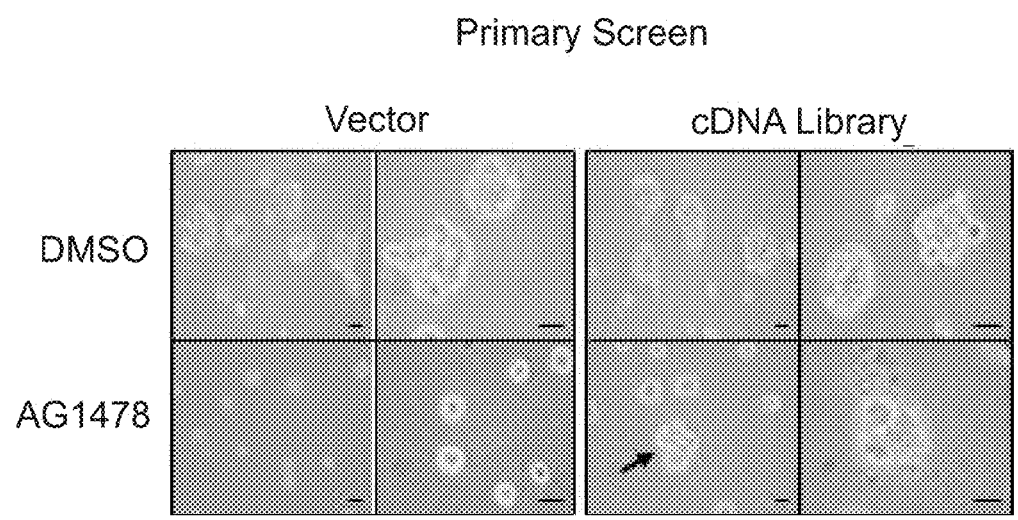
FIGS. 2A and 2B are microscopic visual fields showing cDNA expressing T4-2 cells treated with DMSO control or AG1478.
Figure 2B:
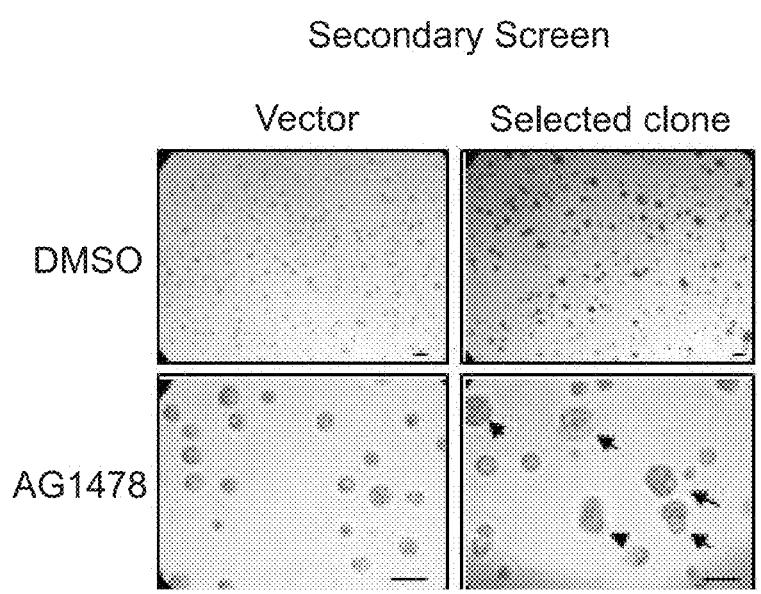

The retroviral cDNA library from malignant T4-2 cells was re-introduced into T4-2 cells. Retrovirus transduced T4-2 cells were subsequently grown on 3D1rECM with one of the small molecule inhibitors, AG1478 (EGFR inhibitor), PD98059 (mitogen-activated protein kinase inhibitor), or LY294002 (PI3K inhibitor), for 4 days to induce phenotypic reversion. FIG. 2A shows microscopic visual fields of a number of big and disorganized colonies that failed to form acinar structure in the cDNA library transduced population when cells were plated in 3D1rECM. By contrast, FIG. 2A also shows control vehicle transduced control cells completely reverted and exhibited growth arrested phenotypes upon inhibitor treatment. FIG. 2B shows microscopic visual fields of those non-reverted colonies which were isolated from the Matrigel, independently expanded, and subsequently plated on 3D 1rECM in the presence of the same inhibitor for elimination of false positives. After the second round of screening, the cDNA inserts were recovered from genomic DNA by PCR using primers to the flanking sequences of the retroviral cloning vector. Genomic DNA was isolated from selected clones grown on the monolayer.

Cells were trypsinized and subjected to extraction of genomic DNA. Polymerase Chain Reaction (PCR) amplification of genomic DNA was performed to recover retroviral inserts using primers: 5'-TGGACCATCCTCTAGACTGC-3' (SEQ ID NO: 17) and 5'-TCAGGGTTATTGTCTCATGA-3' (SEQ ID NO:18) flanking sequences in the retroviral cloning vector, pESY-Neo. The genomic DNA PCR reaction was one cycle of 94° C. for 120 sec, 30 cycles at 94° C. for 30 sec, 60° C. for 30 sec, and 72° C. for 5 minutes, and finally one cycle of 72° C. for 10 minutes. The DNA amplicons were visualized on 0.7% agarose electrophoresis.

Each amplified cDNA fragment from genomic DNA PCR was excised, then ligated to pGEM cloning vector and subjected to nucleotide sequencing from both ends using $T_7$ and $SP_6$ sequencing primers. cDNA sequence homology was analyzed and identified by BLASTN search at National Center for Biotechnology Information (NCBI) database.

Figure 3:
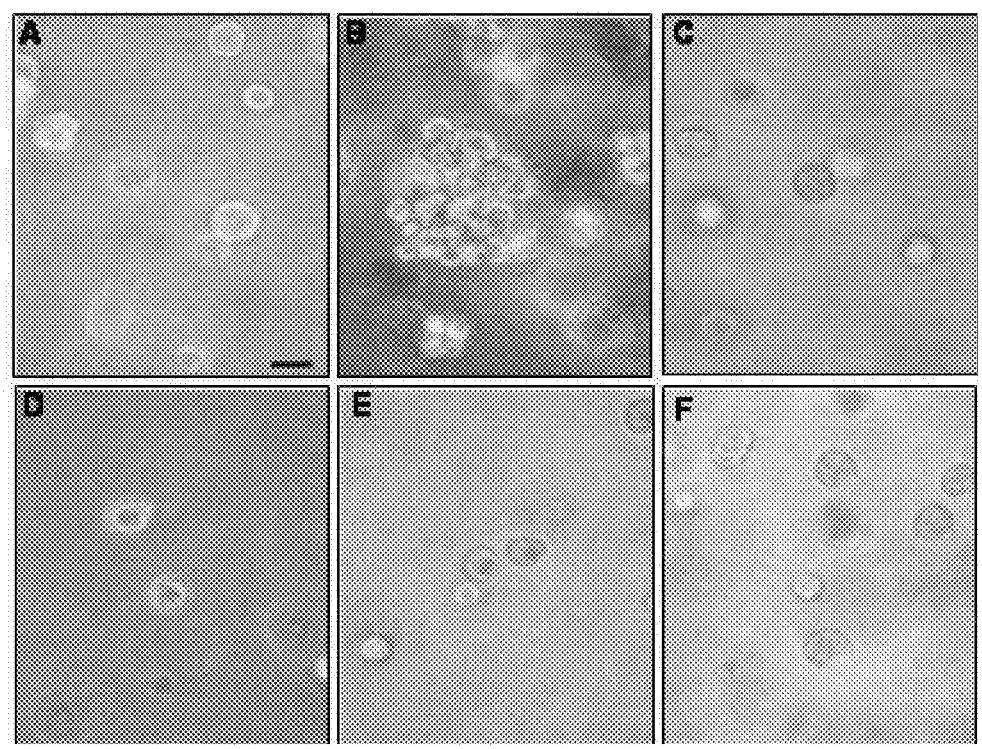
FIG. 3A is a microscopic visual field showing non-malignant S1 cells cultured in 3D 1rECM.
FIG. 3B is a microscopic visual field showing T4-2 cells cultured in 3D 1rECM.
FIG. 3C is a microscopic visual field showing T4-2 cells treated with AG1478 and cultured in 3D 1rECM.
FIG. 3D is a microscopic visual field showing T4-2 cells treated with LU294002 and cultured in 3D 1rECM.
FIG. 3E is a microscopic visual field showing T4-2 cells treated with PD98059 and cultured in 3D 1rECM
FIG. 3F is a microscopic visual field showing T4-2 cells treated with AIIB2 and cultured in 3D 1rECM.

Microscopic visual fields of FIG. 3 show non-malignant HMT3522 S1 cells form polarized acinar structures (FIG. 3A) resembling normally differentiated acinus in vivo, whereas malignant T4-2 cells form disorganized colonies constantly growing on 3D 1rECM (FIG. 3B). Moreover, when T4-2 cells are cultured in 3D 1rECM with signaling inhibitors of EGFR (100 nM AG1478 Tyrphostin), PI3K (6 µM LY294002), MEK (20 µM PD98059) or β-integrin blocking antibody (0.15 mg/mL AIIB2), phenotypically normal acinus-like structures were induced (FIG. 3C-3F).

Five genes were identified from the phenotypic screen which conferred resistance to signaling inhibitors in preventing phenotypic reversion of malignant T4-2 cells in 3D cultures. FAM83A and Rab32 conferred resistance to the EGFR inhibitor AG1478. MRGBP, PTBP1, and ZFPL1 conferred resistance to the PI3K inhibitor LY294002.

Example 3

Molecular Cloning of FAM83A

Retroviral pESY-Neor and pBM-IRES-puror vector were used for expression of FAM83A in human mammary epithelial cells. The full length of human FAM83A cDNA was amplified using LA Taq™ DNA polymerase with the following primers: 5'-GAATTCATGAGCCGGTCAAGGCGCCT-3' (SEQ ID NO: 9) and 5'-CTCGAGTCAGAAGTGAGGG-GAGGCCTGCA-3' (SEQ ID NO: 10). The full-length FAM83A PCR product was subcloned to pGEM cloning vector, verified by sequence analysis and FAM83A cDNA was inserted to retroviral vector pBM-IRES-Puror using EcoRI-XhoI restriction sites. The FLAG-tagged FAM83A cDNA was generated by RT-PCR using the following primers: 5'-AATTCATGAGCCGGTCAAGGCACCT3' (SEQ ID NO: 11) and 5'-GAATTCTCGAGCTACT-TGTCGTCGTCGTCCTTGTAGTCGAAGT-GAGGGGAGGC CTG-3' (SEQ ID NO: 12).

Example 4

Figure 4A:
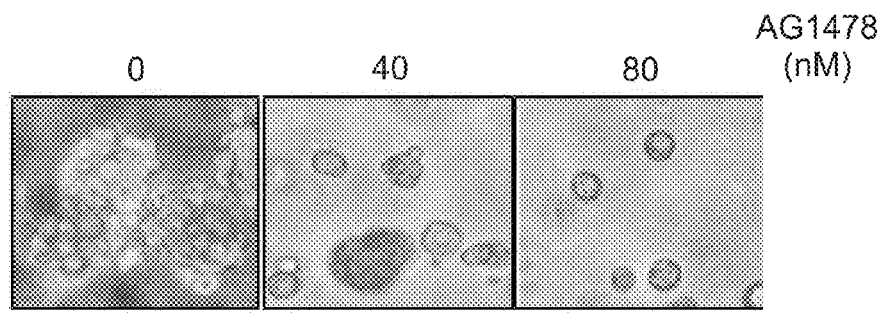
FIG. 4A is a microscopic visual field showing T4-2 cells grown with different concentrations of AG1478 in 3D 1rECM.
Figure 4B:
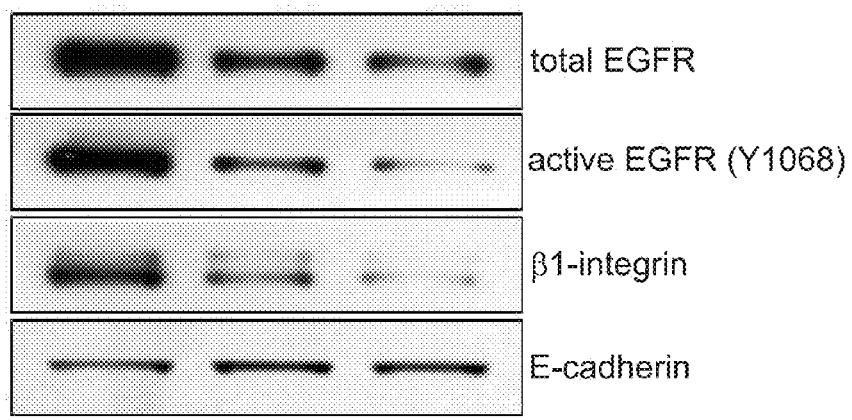
FIG. 4B is a western blot showing total EFGR, active phosphorylated EGFR, β-1 integrin, and E-cadherin levels.
Figure 6A:
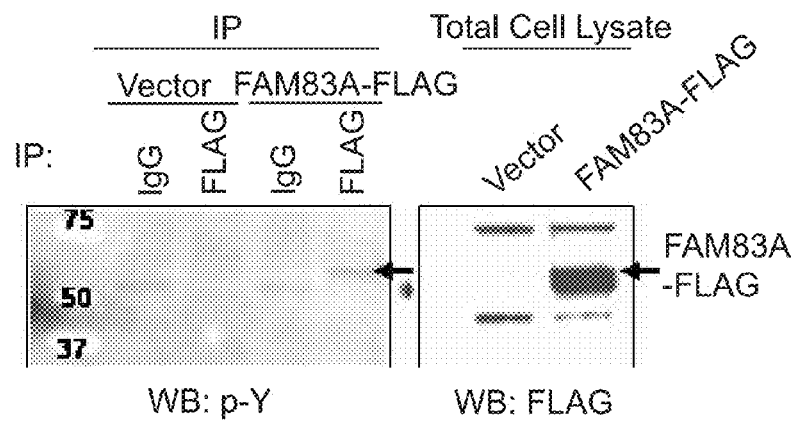
FIG. 6A is a western blot showing immunoprecipitation of FAM83A-FLAG and blotting with anti-phosphotyrosine antibody.
Figure 6B:
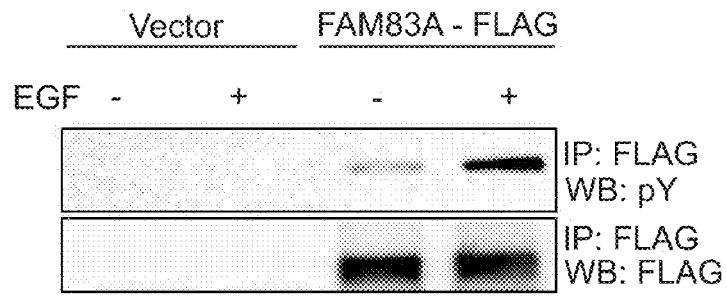
FIG. 6B is a western blot showing immunoprecipitation of FAM83A-FLAG and blotting with anti-phosphotyrosine antibody from lysates of T4-2 cells stimulated with EGF for 6 hours.
Figure 6C:
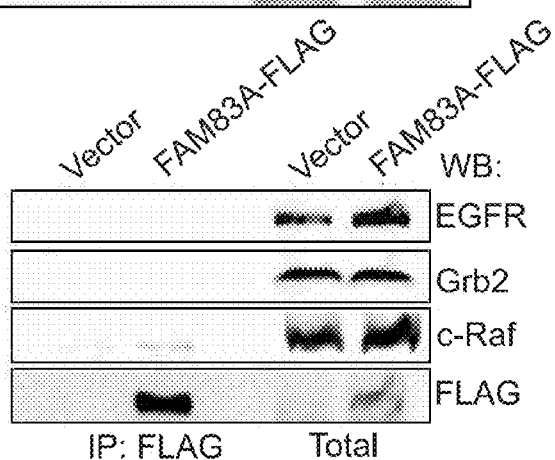
FIG. 6C is a western blot showing immunoprecipitation of FAM83A-FLAG and blotting with anti-EGFR, Grb2, c-Raf, and FLAG antibodies.
Figure 6D:
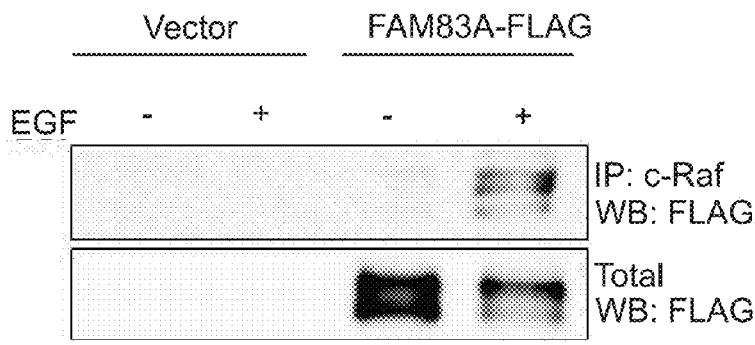
FIG. 6D is a western blot showing immunoprecipitation of FAM83A-FLAG and blotting with anti-c-Raf antibodies from lysates of T4-2 cells stimulated with EGF for 1 hour.

FAM83A Confers Resistance to EGFR Inhibitor and Functions within EGFR Signaling Pathway in 3D Culture FIG. 4A shows microscopic visual fields of T4-2 cells grown for 10 days with different concentrations of EGF receptor kinase inhibitor AG1478 in 3D 1rECM. FIG. 4B is a western blot of extracted cell lysates blotted with antibodies against EGFR, β-integrin, phosphorylated EGFR, and E-cadherin, which was used as a loading control. FIG. 4 indicates that T4-2 cells treated with AG1478 form growth arrested acinus-like structures, have decreased levels of EGFR and β1-integrin proteins, and lower levels of phosphorylated EGFR.

FIG. 5 shows microscopic visual fields of vector control, full-length FAM83A, or truncated FAM83A overexpressing T4-2 cells in the presence of various inhibitors. FIG. 5A shows full-length or truncated FAM83A-expressing T4-2 cells cultured on 3D 1rECM in the absence (top panel) or presence (bottom panel) of the EGFR inhibitor AG1478 (100 nM for 4 days). FIG. 5B shows full-length FAM83A overexpressing T4-2 cells undergo phenotypic reversion in the presence of LY294002 or PD98059, but not AG1478, indicating that FAM83A confers resistance to EGFR inhibition. Indeed, FIG. 6 shows FAM83A is phosphorylated and interacts with c-Raf, a mediator of the EGFR signaling pathway, in response to EGF stimulation.

The effect of FAM83A overexpression in conferring resistance to other EGFR inhibitors was determined FIG. 17C shows vector control and FAM83A-overexpressing T4-2 cells treated with the EGFR inhibitors lapatinib or gefitinib. Control T4-2 cells were reverted by lapatinib and gefitinib similar to AG1478. In contrast, FAM83A-overexpressing cells maintained disorganized structures in the presence of lapatinib or gefitinib. These results indicate that FAM83A confers resistance to a variety of EGFR inhibitors.

Example 5

Endogenous FAM83A is Down-Regulated During the Formation of Acinus-Like Structures in Reverted T4-2 Cells and Non-Malignant S1 Cells The expression level of endogenous FAM83A in non-reverted and reverted T4-2 cells was analyzed by RT-PCR and western blot with antibody against endogenous FAM83A. FIG. 7A shows RT-PCR analysis of FAM83A RNA levels in T4-2 cells cultured in both 2D monolayer and 3D 1rECM treated with AG1478 or vehicle control DMSO for 4 days. FIG. 7B is a bar graph quantification of the results from FIG. 7A. FIG. 7C shows RT-PCR analysis of FAM83A RNA levels in S1 cells growing in 2D or 3D cultures. FIG. 7C is a western blot comparison of FAM83A protein levels in S1 and T4-2 cells growing in 2D or 3D cultures in the presence or absence of AG1478.

Results shown in FIG. 7 indicate that FAM83A mRNA and protein expression is decreased in T4-2 cells induced to undergo phenotypic reversion by AG1478 treatment.

Example 6

Figure 8A:
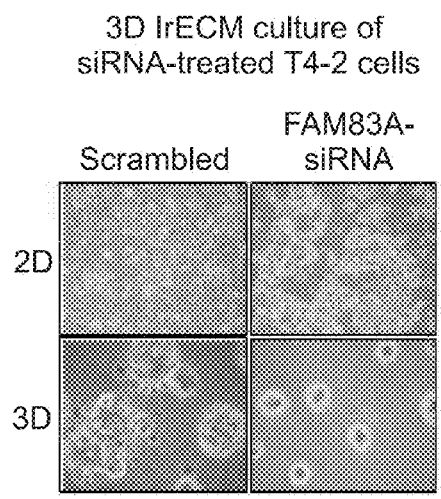
FIG. 8A is a panel of microscopic visual fields showing T4-2 cells treated with control or FAM83A-siRNA in 3D 1rECM.
Figure 8B:
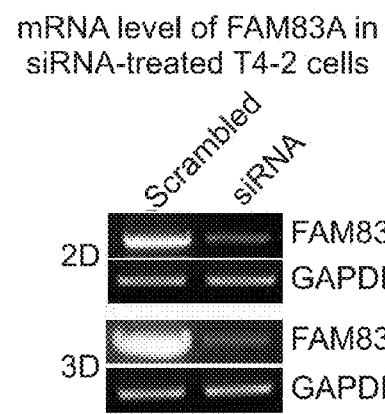
FIG. 8B is a RT-PCR analysis of FAM83A RNA levels in T4-2 cells treated with control or FAM83A-siRNA in 3D 1rECM.
Figure 8C:
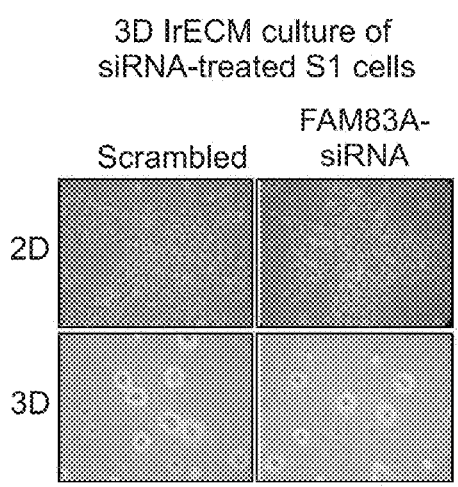
FIG. 8C is a panel of microscopic visual fields showing S1 cells treated with control or FAM83A-siRNA in 3D 1rECM.
Figure 8D:
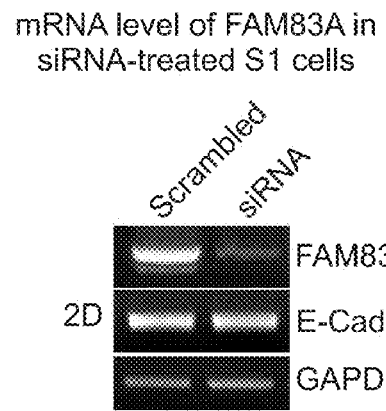
FIG. 8D is a RT-PCR analysis of FAM83A RNA levels in S1 cells treated with control or FAM83A-siRNA in 3D 1rECM.
Figure 8E:
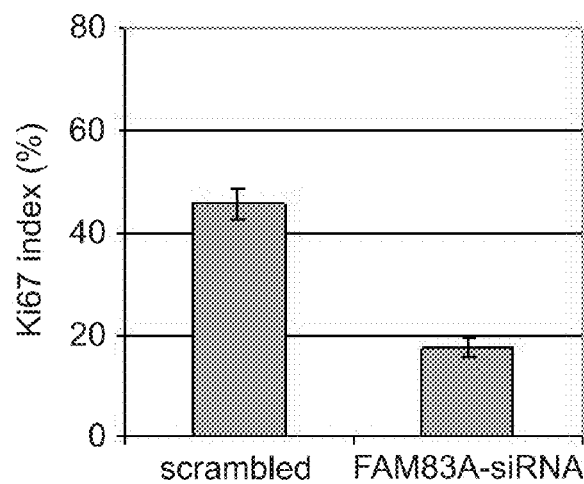
FIG. 8E is a bar graph measurement of Ki67 positive siRNA-treated cells in 3D 1rECM.
Figure 8F:
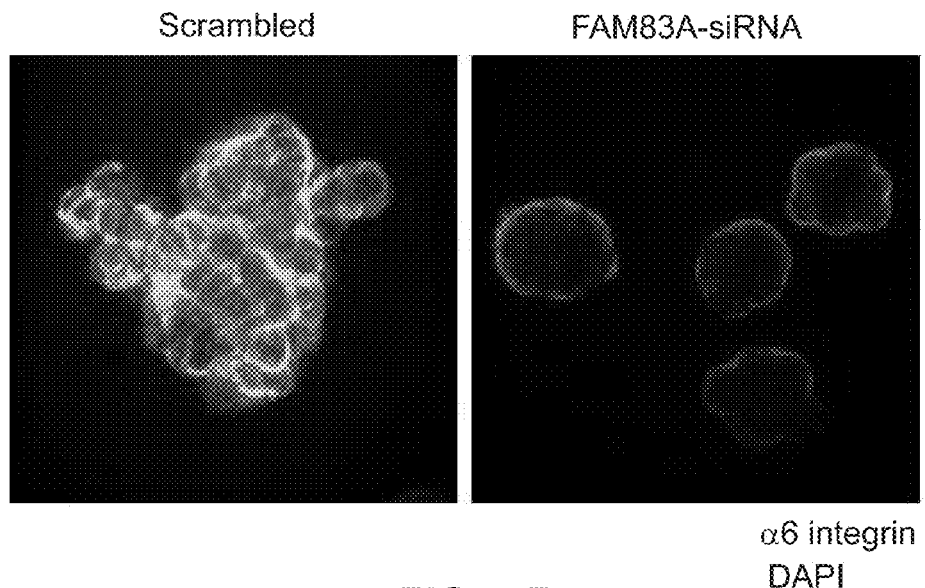
FIG. 8F is a panel of confocal microscopic images of α6 integrin and DAPI staining of negative control and FAM83A-siRNA treated T4-2 cells cultured in 3D 1rECM.

Knocking-Down FAM83A Restores Acinar Morphology of Human Breast Cancer T4-2 Cells T4-2 cells were treated with short interfering RNA (siRNA) to reduce FAM83A expression. FIG. 8A shows phase-contrast morphology of T4-2 cells treated with scrambled negative control and FAM83A-specific siRNA for 48 hours cultured in 1rECM or in monolayer without reverting agents for 4 days. FIG. 8B shows mRNA levels of FAM83A measured by RT-PCR in both 2D and 3D culture in siRNA-treated T4-2 cells. FIG. 8C shows phase-contrast morphology of S1 cells treated with scrambled or FAM83A-specific siRNA in 2D for 48 hours and placed on top of 1rECM for 3 days. FIG. 8D shows RT-PCR assessment of FAM83A reduction by siRNA treatment in S1 cells. FIG. 8E shows measurement of cell proliferation rate by counting Ki-67 positive cells in 3D culture. FIG. 8F shows confocal images of α6 integrin and DAPI staining of negative control and siRNA-treated T4-2 cells on 3D 1rECM culture.

These data demonstrate that FAM83A-siRNA reduces the growth of T4-2 cells in 2D culture and induces phenotypic reversion in 3D 1rECM. FAM83A-specific siRNA-treated T4-2 cells, but not those treated with a scrambled negative control, formed phenotypically normalized acinus-like structures in 3D 1rECM (FIGS. 8A, B). In contrast, siRNA-mediated down regulation of FAM83A in non-malignant S1 cells had no significant phenotypic effect in 3D culture (FIGS. 8C, D).

The phenotypic reversion of T4-2 cell with FAM83A-specific siRNA was accompanied by a 70% decrease in proliferation compared to scrambled negative control (FIG. 8E). Moreover, FAM83A-specific siRNA-treated T4-2 cells established basal polarity in 3D 1rECM (FIG. 8F), suggesting that decreased expression of FAM83A is necessary and sufficient to form the polarized acinus-like structures of T4-2 cells in 3D culture. This result is consistent with the RT-PCR data that FAM83A mRNA was expressed at lower level in the phenotypically normalized T4-2 cells than in continuously growing non-reverted T4-2 cells (FIG. 7A, B).

Example 7

Reduction of FAM83a Affects Actin Cytoskeleton Organization in Human Breast Cancer T4-2 Cells but not S1 Cells Integrins and the cytoskeleton crosstalk with each other reciprocally and regulate cellular organization and function. Integrin receptors form links between extracellular matrix and the actin cytoskeleton, and cytoskeletal organization regulates integrin-mediated adhesion. The effect of reducing FAM83A on actin cytoskeleton organization was tested by treating T4-2 cells with FAM83A-specific or scrambled negative control siRNA.

Figure 9:
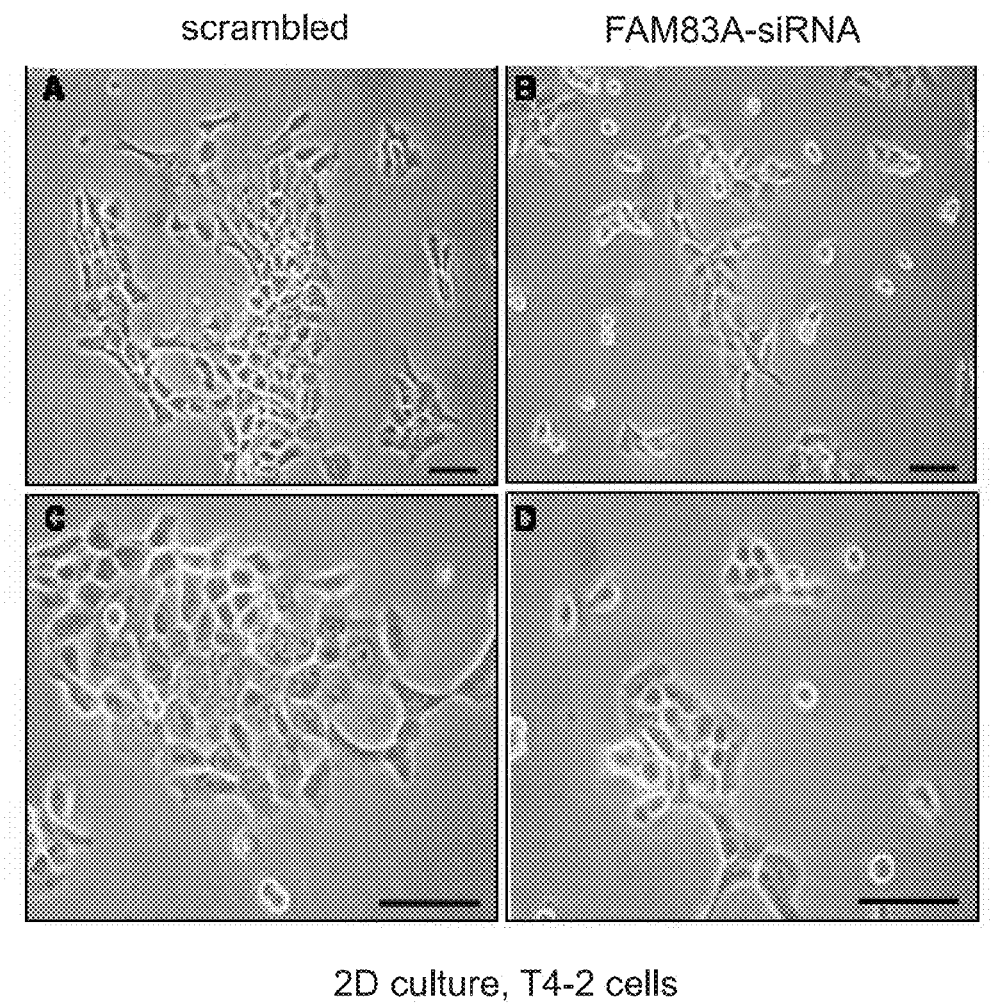
FIG. 9 is a panel of phase contrast microscopic visual fields showing T4-2 cells treated with control or FAM83A-siRNA cultured in 2D.

FIG. 9 shows phase contrast images of scrambled negative control siRNA (FIGS. 9A, C) and FAM83A-specific siRNA treated T4-2 cells (FIGS. 9B, D) for 48 hours. These data indicate that knocking down FAM83A significantly reduced cell spreading.

Figure 10A:
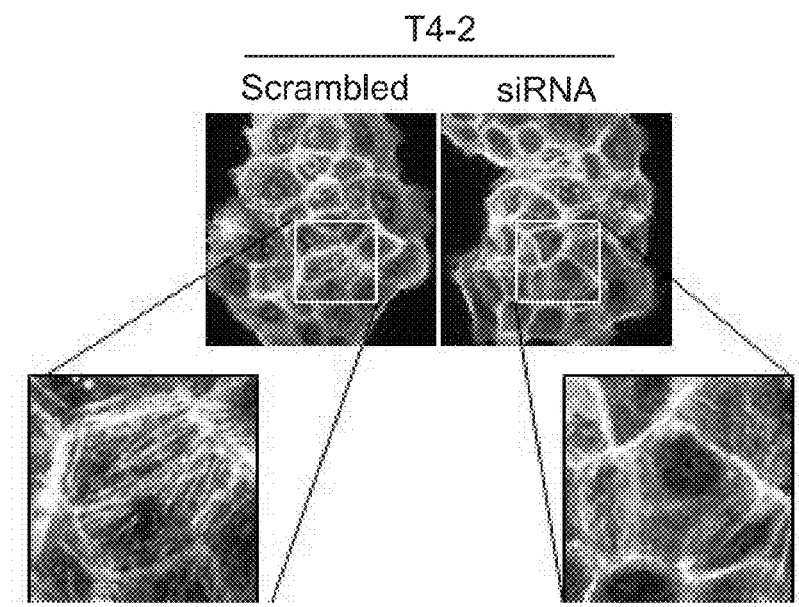
FIG. 10A is a panel of confocal images of T4-2 cells treated with control or FAM83A-siRNA and stained for F-actin with phalloidin.
Figure 10B:
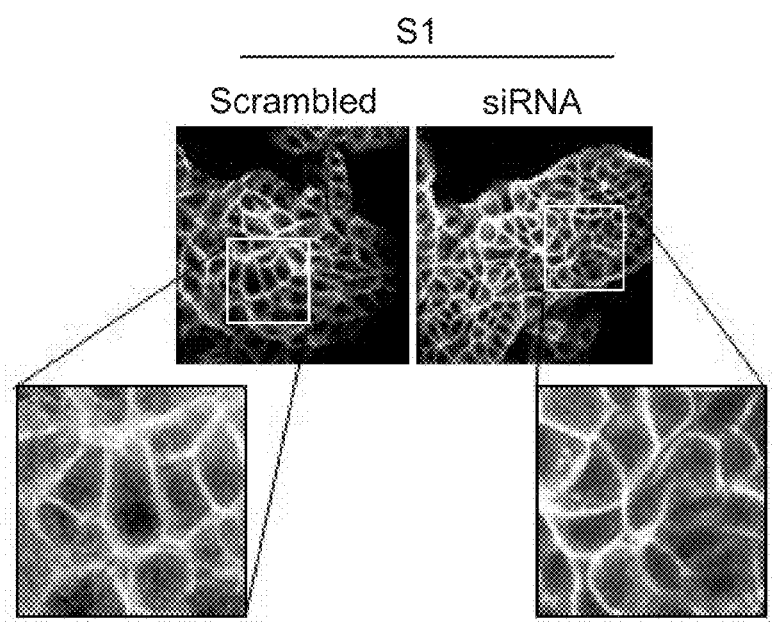
FIG. 10B is a panel of confocal images of S1 cells treated with control or FAM83A-siRNA and stained for F-actin with phalloidin.

FIG. 10 shows confocal images of F-actin staining with phalloidin in control or FAM83A siRNA-treated T4-2 cells (FIG. 10A) and S1 cells (FIG. 10B). Control T4-2 cells formed abundant stress fibers, whereas FAM83A siRNA-treated cells had a decrease in stress fibers, but increased staining in cortical actin (FIG. 10A). siRNA-mediated depletion of FAM83A in non-malignant HMT3522 S1 had no significant effect on stress fiber formation, but cells grew as compact islands and exhibited strong cortical actin (FIG. 10B).

Example 8

FAM83A is Involved in Invasive Behavior in Human Breast Cancer T4-2 Cells

The role of FAM83A in cell invasion was investigated by testing the effect of knocking down FAM83A by siRNA or overexpressing FAM83A in T4-2 cells using a Matrigel-coated transwell chamber assay.

Figure 11A:
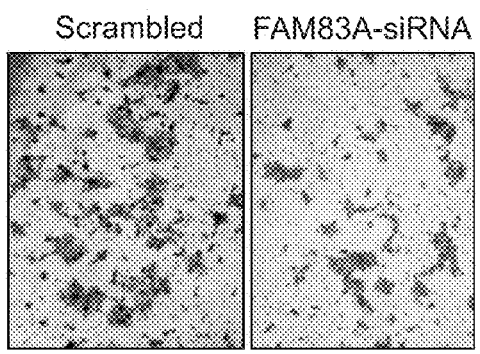
FIG. 11A is an invasion assay using Matrigel-coated transwell filters showing TF-2 cells treated with control or FAM83A-siRNA.
Figure 11B:
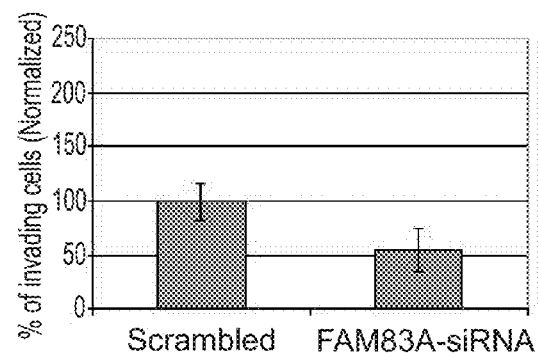
FIG. 11B is a bar graph measurement of the percentage of invading cells from FIG. 11A.
Figure 11C:
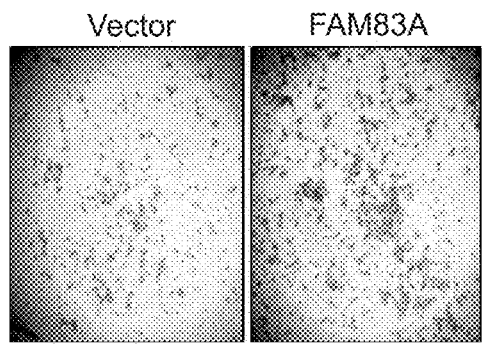
FIG. 11C is an invasion assay using Matrigel-coated transwell filters showing TF-2 cells overexpressing vector control or FAM83A.
Figure 11D:
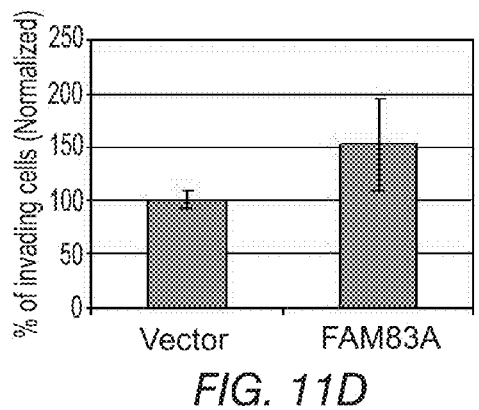
FIG. 11D is a bar graph measurement of the percentage of invading cells from FIG. 11C.

FIG. 11A shows T4-2 cells treated with scrambled siRNA or FAM83A siRNA for 72 hours and subjected to invasion assay using Matrigel-coated transwell filters. After 48 hours, cells were fixed, stained and quantified. FIG. 11B is a graph quantifying the percentage of invading cells from FIG. 11A. FIG. 11C shows T4-2 cells transduced to overexpress vesicle control or FAM83A and assayed for invasion. FIG. 11D is a graph quantifying the percentage of invading cells from FIG. 11C.

These results show that FAM83A-specific siRNA-treated T4-2 cells were less invasive compared to scrambled negative control. Conversely, FAM83A overexpressing T4-2 cells showed about 50% increase in the invasiveness compared to vector control. These results indicate a role of FAM83A in the invasiveness of breast cancer cells.

Example 9

Overexpression of FAM83A in Non-Malignant S1 Cells

The ability of FAM83A overexpression to disturb acinar morphogenesis in non-malignant S1 cells cultured 3D 1rECM was determined FIG. 12A shows introduction and expression of full-length FLAG-tagged FAM83A into S1 cells confirmed by western blotting using FLAG antibody. FIG. 12B shows microscopic visual fields of FAM83A-expressing S1 cells cultured in 2D culture (top panel) and 3D 1rECM (bottom panel). FIG. 12C shows confocal images of α6-integrin staining of S1 cells expressing FAM83A or vector control on 3D 1rECM.

These results reveal that FAM83A expressing S1 cells formed disorganized acini in 3D1rECM (FIG. 12B). FAM83A expressing S1 cells showed disorganized basal polarity approximately 2 fold more frequently than compared empty vector containing cells in 3D culture (FIG. 12C).

Example 10

Generation of Anti-FAM83A Polyclonal Antibody and Analysis of FAM83A Protein Expression A 14 amino acid peptide fragment of FAM83A (SEQ ID NO:6) was used to raise rabbit anti-sera specific for FAM83A. FIG. 13 shows western blot analysis to detect FAM83A in naïve T4-2 cells using the polyclonal FAM83A antibody (FIG. 13A) and a schematic presentation of putative FAM83A isoforms (FIG. 13B). The observed molecular immunoreactive bands were 99, 49, 23-kDa, respectively (FIG. 13A), whereas the predicted molecular weight are about 48 for isoform A, and 40-kDa for isoform B (FIG. 13B).

The specificity of FAM83A polyclonal antibody was tested by performing western blot and immunofluorescence analysis in two different sets of FAM83A-specific siRNA-treated T4-2 cells (siRNA#1, SEQ ID NO:1; and siRNA#2, SEQ ID NO:2) using the FAM83A polyclonal antibody.

Figure 14A:
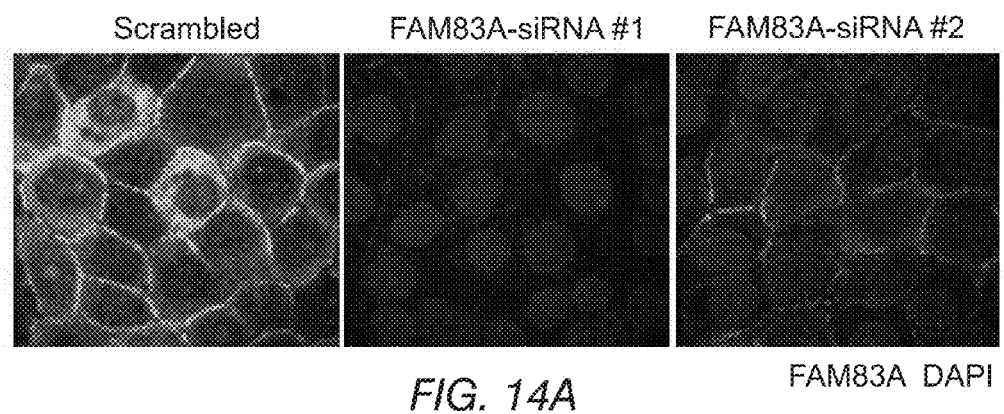
FIG. 14A is a panel of immunofluorescence visual fields showing staining of FAM83A using a polyclonal antibody against FAM83A in T4-2 cells treated with control or FAM83A-siRNA.
Figure 14B:
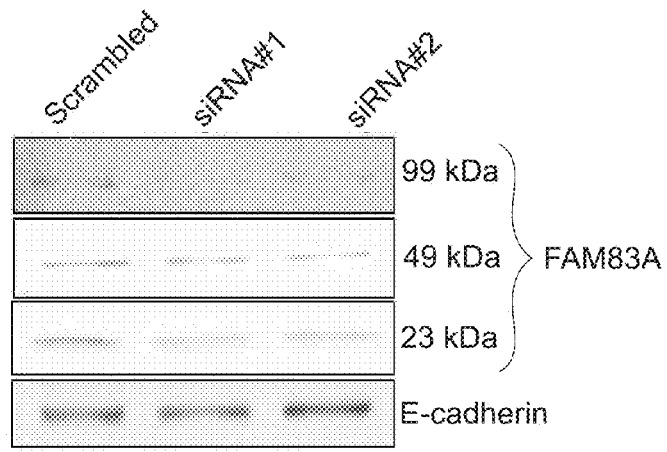
FIG. 14B is a western blot showing detection of FAM83A using a polyclonal antibody against FAM83A in lysates from T4-2 cells treated with control or FAM83A-siRNA.

FIG. 14A shows immunofluorescence visual fields which demonstrated that FAM83A was highly expressed in the plasma membrane and cytoplasm of the scrambled siRNA treated T4-2 cells, but greatly reduced in the siRNA treated cells. FIG. 14B shows western blot analysis using anti-FAM83A polyclonal antibody and lysates from the cells treated with the two different sets of siRNA or the scrambled control. These results indicated that the 99 and 23 kDa bands were reduced in both sets of siRNA-treated cells (siRNA#1 and #2) compared to scrambled control, whereas the 49 kDa band was downregulated in only one set of siRNA-treated cells (siRNA#2) (FIG. 14B).

Example 11

Expression of FAM83A in Non-Malignant and Malignant Cell Lines

Figure 15A:
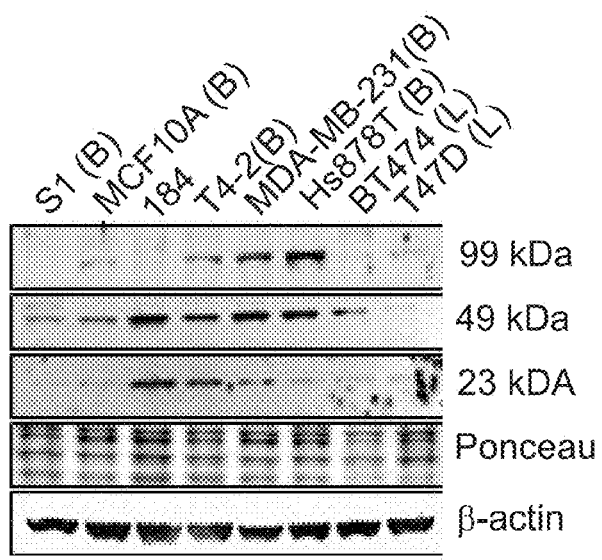
FIG. 15A is a western blot showing FAM83A levels in normal and cancer cell lines.
Figure 15B:
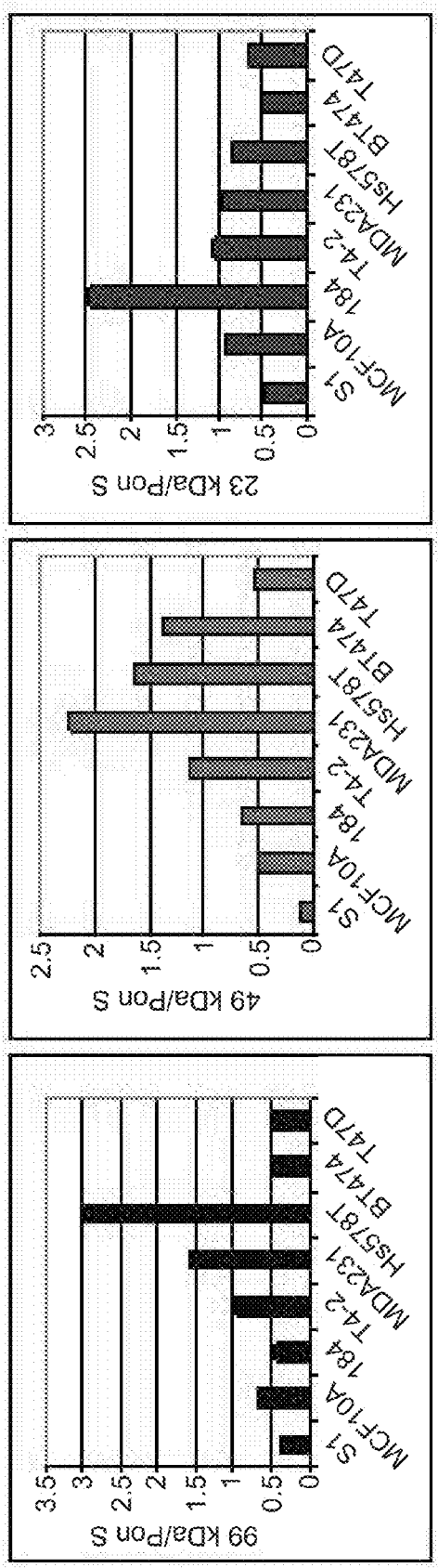
FIG. 15B is a panel of bar graphs showing quantification of FAM83A levels from FIG. 15A normalized with protein stained by Ponceau S.
Figure 15C:
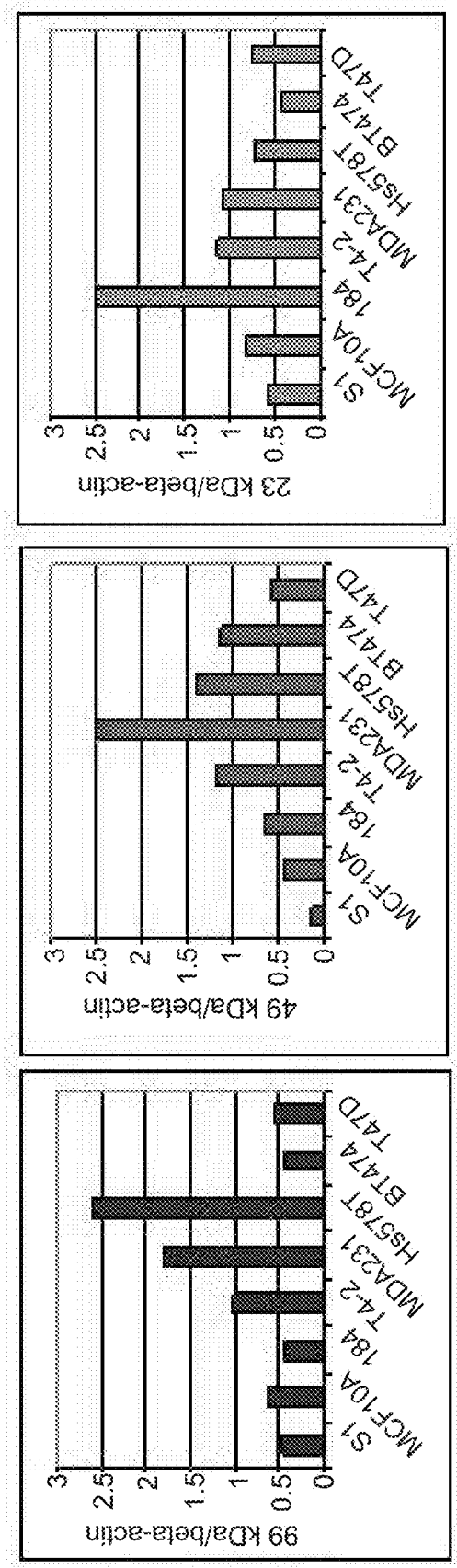
FIG. 15C is a panel of bar graphs showing quantification of FAM83A levels from FIG. 15A normalized with β-actin.

The expression pattern of FAM83A in normal and cancer cell lines was surveyed by performing western blot analysis with polyclonal FAM83A antibody. FIG. 15A is a western blot showing that the 99 and 49 kDa FAM83A were expressed more highly in malignant cells than non-malignant mammary epithelial cells including S1, MCF10A, and HMEC 184. The subtype of cell is indicated as L, luminal, and B, Basal epithelial cell. FIGS. 15B and 15C are graphs showing quantification of each FAM83A protein band displayed on the western blotting. Total proteins stained with Ponceau S (FIG. 15B) and β-actin (FIG. 15C) were used for loading control.

These data demonstrate that the 23 kDa FAM83A expresses at a similar level in the first two non-malignant cell lines, except for HMEC 184, and cancer cell lines (FIGS. 15A, B). In particular, the 99 kDa FAM83A was highly expressed in basal epithelial cells (T4-2, MDA-MB-231, and Hs578T) but not luminal epithelial cells (BT474 and T47D).

Figures 16A, 16B:
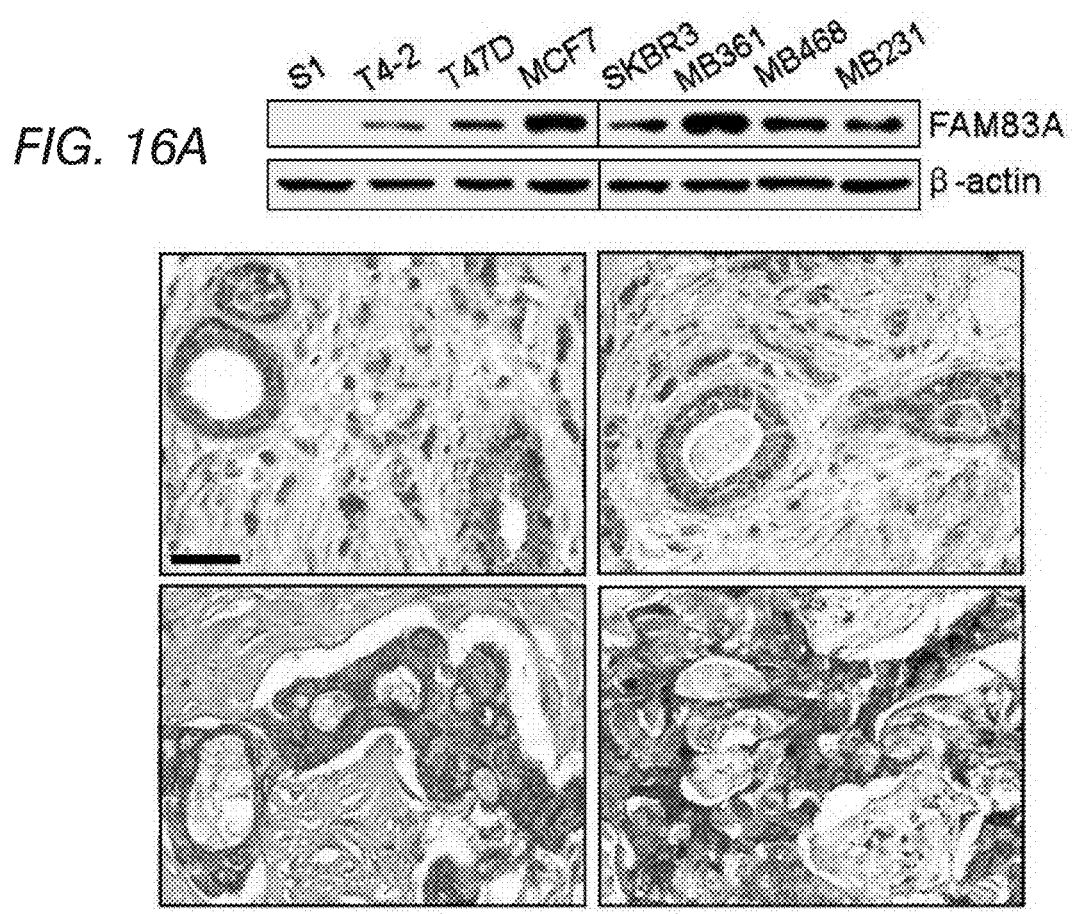
FIG. 16A is a western blot showing FAM83A levels in a panel of breast epithelial cell lines.
FIG. 16B is a panel of microscopic visual fields showing staining of FAM83A in normal (top panel) and malignant (bottom panel) breast tissue specimens.

The expression pattern of FAM83A in a panel of breast epithelial cell lines was determined. FIG. 16A is a western blot showing that FAM83A was highly expressed in MCF-7 and T47D cells and in aggressive cell lines including SKBR3, MDA-MB-361, MDA-MB-468, and MDA-MB-231. FIG. 16B shows that FAM83A staining was mostly weak just above the background level in normal cells, whereas malignant cells showed strong cytosolic staining. Overall, only 6% (1/16) of normal tissues were positive for FAM83A staining while 94% (45/48) of malignant tissues showed positive staining.

Example 12

FAM83A Expression is Important for the Growth and Lapatinib-Resistance of Breast Cancer Cell Xenografts In Vivo To establish the relevance of the above findings in an in vivo setting, T4-2 cells treated with control scrambled siRNA or FAM83A siRNA-treated were injected subcutaneously into the rear flank of nude mice.

Animal experiments were performed under federal guidelines and approved by Institutional Animal Welfare and Research Committee at LBN. Exponentially growing T4-2 cells or MDA-MB-468 cells were suspended at the density of $5 \times 10^6$ or $10 \times 10^6$, respectively, in 100 µl medium containing DMEM/F12 medium (50%) and Matrigel (50%). Cell suspension was subcutaneously injected into the rear flank of 6-8 wk old athymic female BALB/c-nude mice (nu/nu) (Charles River Laboratories) (n=8 per group). Tumor volumes were measured every other day. ANOVA 2-way analysis with Bonferroni post test was used to determine p-value. At the end of experiments, mice were sacrificed and subjected to pathological examinations.

Despite that tumor take was not significantly different between both groups (controls: 8 of 8; siFAM83A: 6 of 8), FIG. 17A shows that tumor growth of FAM83A siRNA-treated cells was reduced to ⅓ of the control cells.

To confirm this observation for cells with stable FAM83A-depletion and a different genetic background, control or FAM83A shRNA-treated MDA-MB468 cells were subcutaneously injected into the rear flank of nude mice and monitored for their growth. For FAM83A shRNA production, a double-stranded DNA oligonucleotide was generated from the following sequences: sense, 5'-GATCC GTGTGGAAGGAGAGATATACTTCCTGTCAGATATA-TCTCTCCTTCCAC ACTTTTTG-3' (SEQ ID NO:7); antisense, 5'-AATTCAAAAA GTGTGGAAGGAGAGATATATCTGACAGGAAGTAT-ATCTCTCCT TCCACACG-3' (SEQ ID NO:8) (target sequence underlined; BamH1/EcoR1 cohesive ends italicized). Both oligonucleotides were annealed and ligated into BamH1/EcoR1 site of pGreen puro lentival vector (System Biosciences).

FIG. 17B shows that tumor growth of FAM83A-depleted MDA-MB468 cells was reduced to ¼ of the control cells. These results suggest that FAM83A may be a therapeutic target to suppress tumor growth.

The ability of FAM83A to confer cancer cell resistance to EGFR inhibitor in vivo was determined Vector control or FAM83A-overexpressing T4-2 cells were xenografted into mice, which were orally administered lapatinib by oral gavage at 30 mg/kg or 100 mg/kg twice daily for 3 weeks. Tumors derived from T4-2 cells were grown to 100 mm$^3$ (day 5). Then, mice were randomized into vehicle (0.5% hydroxypropylmethylcellulose with 0.1% Tween 80 in water; n=8) and experimental treatment groups (n=8) to receive oral gavage of lapatinib at 30 mg/kg or 100 mg/kg twice daily for 3 weeks. FIG. 17D shows that without treatment, the sizes of tumors derived from both control and FAM83A-overexpressing cells had little difference. With lapatinib treatment, however, the growth of control tumors was significantly inhibited, whereas the growth of FAM83A-overexpressing tumors was not affected and reached the size 5 times larger than controls. FIG. 18A shows that tumor inhibitory action of lapatinib on control cells was independent of the dose above 30 mg/kg. As shown in FIG. 18B, pathological examination of sectioned tumors revealed that lapatinib-treated control tumors were well-circumscribed and distinctly separated from the stromal regions, suggesting their reduced invasiveness. In contrast, lapatinib-treated FAM83A-overexpressing tumors had been invading the stromal regions, suggesting their invasive phenotype indistinguishable from cells untreated with lapatinib. These observations suggest that FAM83A-overexpression impairs the tumor inhibitory action of lapatinib.

Example 13

FAM83A Expression is Associated with Clinically Higher Mortality from Breast-Cancer The association between FAM83A expression and clinical outcome of breast cancer was determined using a microarray gene-expression dataset and generating a Kaplan-Meier survival curve. As shown in FIG. 17E, patients whose tumors had above median levels of FAM83A expression displayed significantly higher breast-cancer related mortality relative to patients carrying tumors with lower levels of expression (p=0.022; log-rank test), suggesting that high levels of FAM83A may contribute to poor clinical outcome.

Example 14

Diagnosing Cancer Resistance to an EGFR Tyrosine Kinase Inhibitor

A biological sample containing cancer cells is taken from a patient. FAM83A levels are detected in the patient's cancer cells and compared to control levels. The patient is diagnosed as having cancer resistant to an EGFR tyrosine kinase inhibitor upon detection of increased FAM83A levels in the patient's cancer cells relative to control levels.

Example 15

Diagnosing Breast Cancer Resistance to an EGFR Tyrosine Kinase Inhibitor

A biological sample containing breast cancer cells is taken from a patient. FAM83A levels are detected in the patient's breast cancer cells and compared to control levels. The patient is diagnosed as having breast cancer resistant to an EGFR tyrosine kinase inhibitor upon detection of increased FAM83A levels in the patient's breast cancer cells relative to control levels.

Example 16

Identification of a Therapeutic Compound for Treating Cancer Resistant to an EGFR Tyrosine Kinase Inhibitor A gene that confers cancer resistance to an EGFR tyrosine kinase inhibitor is identified by screening for inhibition of breast cancer cell reversion to a phenotypically normal structure in response to EGFR tyrosine kinase inhibitor. A therapeutic compound that inhibits expression of the identified gene or activity of its encoded protein is generated. The compound is tested for its ability to induce breast cancer cell reversion to a phenotypically normal structure. A therapeutic compound for treating cancer resistant to an EGFR tyrosine kinase inhibitor is discovered.

Example 17

Identification of a Therapeutic Compound for Treating Breast Cancer Resistant to an EGFR Tyrosine Kinase Inhibitor A gene that confers breast cancer resistance to an EGFR tyrosine kinase inhibitor is identified by screening for inhibition of breast cancer cell reversion to a phenotypically normal structure in response to EGFR tyrosine kinase inhibitor. A therapeutic compound that inhibits expression of the identified gene or activity of its encoded protein is generated. The compound is tested for its ability to induce breast cancer cell reversion to a phenotypically normal structure. A therapeutic compound for treating breast cancer resistant to an EGFR tyrosine kinase inhibitor is discovered.

The invention now being fully described, it will be apparent to one of ordinary skill in the art that many changes and modifications can be made thereto without departing from the spirit or scope of the appended claims.

What is claimed is:

1. A method of predicting a clinical outcome for a patient having breast cancer, comprising:
   providing a biological sample comprising breast cancer cells from the patient;
   contacting said breast cancer cells with an antibody specific for FAM83A;
   detecting a FAM83A expression level in the breast cancer cells by measuring the level of binding between the antibody and the breast cancer cells; and
   predicting the clinical outcome of the patient based on the FAM83A expression level, wherein the FAM83A expression level is positively correlated with the breast-cancer related mortality.

2. The method of claim 1, wherein predicting the clinical outcome comprises generating a Kaplan-Merier survival curve.

3. The method of claim 1, wherein the antibody specific for FAM83A is a polyclonal antibody against FAM83A.

4. The method of claim 3, wherein the polyclonal antibody is raised against a peptide having an amino acid sequence of SEQ ID NO: 6.

5. The method of claim 3, wherein the polyclonal antibody is raised against a peptide having an amino acid sequence of SEQ ID NO: 2.

6. The method of claim 1, wherein the antibody specific for FAM83A protein is a monoclonal antibody against FAM83A.

7. The method of claim 1, wherein high expression level of FAM83A in said patient is indicative of high clinical mortality as compared to patients carrying tumors with lower expression levels of FAM83A.

8. The method of claim 1, wherein the biological sample is a biopsy sample from the patient.

* * * * *

SEQUENCE LISTING

<160> NUMBER OF SEQ ID NOS: 18

<210> SEQ ID NO 1
<211> LENGTH: 1305
<212> TYPE: DNA

-continued

<213> ORGANISM: Homo sapien

<400> SEQUENCE: 1

```
atgagccggt caaggcacct gggcaaaatc cggaagcgtc tggaagatgt caagagccag      60
tgggtccggc cagccagggc tgactttagt gacaacgaga gtgcccggct ggccacggac     120
gccctcttgg atggggttc tgaagcctac tggcgggtgc tcagccagga aggcgaggtg     180
gacttcttgt cctcggtgga ggcccagtac atccaggccc aggccaggga gccccgtgt     240
cccccagaca ccctgggagg ggcggaagca ggccctaagg gactggactc cagctcccta     300
cagtccggca cctacttccc tgtggcctca gagggcagcg agccggccct actgcacagc     360
tgggcctcag ctgagaagcc ctacctgaag gaaaaatcca gcgccactgt gtacttccag     420
accgtcaagc acaacaacat cagagacctc gtccgccgct gcatcacccg gactagccag     480
gtcctggtca tcctgatgga tgtgttcacg gatgtggaga tcttctgtga cattctagag     540
gcagccaaca gcgtggggt gttcgtttgt gtgctcctgg accagggagg tgtgaagctc     600
ttccaggaga tgtgtgacaa agtccagatc tctgacagtc acctcaagaa catttccatc     660
cggagtgtgg aaggagagat atactgtgcc aagtcaggca ggaaattcgc tggccaaatc     720
cgggagaagt tcatcatctc ggactggaga tttgtcctgt ctggatctta cagcttcacc     780
tggctctgcg gacacgtgca ccggaacatc ctctccaagt tcacaggcca ggcggtggag     840
ctgtttgaca aggagttccg ccacctctac gcctcctcca gcctgtgat gggcctgaag     900
tccccgcggc tggtcgcccc cgtcccgccc ggagcagccc cggccaatgg ccgccttagc     960
agcagcagtg gctccgccag tgaccgcacg tcctccaacc ccttcagcgg ccgctcggca    1020
ggcagccacc ccggtacccg aagtgtgtcc gcgtcttcag ggccctgtag ccccgcggcc    1080
ccacacccgc ctccaccgcc ccggttccag ccccaccaag gcccttgggg agccccgagt    1140
ccccaggccc acctctcccc gcggccccac gacggcccgc cgccgctgt ctacagcaac    1200
ctggggggcct acaggcccac gcggctgcag ctggagcagc tgggcctggt gccgaggctg    1260
actccaacct ggaggccctt cctgcaggcc tcccctcact tctga                   1305
```

<210> SEQ ID NO 2
<211> LENGTH: 434
<212> TYPE: PRT
<213> ORGANISM: Homo sapien

<400> SEQUENCE: 2

```
Met Ser Arg Ser Arg His Leu Gly Lys Ile Arg Lys Arg Leu Glu Asp
  1               5                  10                  15

Val Lys Ser Gln Trp Val Arg Pro Ala Arg Ala Asp Phe Ser Asp Asn
                 20                  25                  30

Glu Ser Ala Arg Leu Ala Thr Asp Ala Leu Leu Asp Gly Gly Ser Glu
             35                  40                  45

Ala Tyr Trp Arg Val Leu Ser Gln Glu Gly Glu Val Asp Phe Leu Ser
         50                  55                  60

Ser Val Glu Ala Gln Tyr Ile Gln Ala Gln Ala Arg Glu Pro Pro Cys
 65                  70                  75                  80

Pro Pro Asp Thr Leu Gly Gly Ala Glu Ala Gly Pro Lys Gly Leu Asp
                 85                  90                  95

Ser Ser Ser Leu Gln Ser Gly Thr Tyr Phe Pro Val Ala Ser Glu Gly
                100                 105                 110

Ser Glu Pro Ala Leu Leu His Ser Trp Ala Ser Ala Glu Lys Pro Tyr
            115                 120                 125
```

```
Leu Lys Glu Lys Ser Ser Ala Thr Val Tyr Phe Gln Thr Val Lys His
    130                 135                 140

Asn Asn Ile Arg Asp Leu Val Arg Arg Cys Ile Thr Arg Thr Ser Gln
145                 150                 155                 160

Val Leu Val Ile Leu Met Asp Val Phe Thr Asp Val Glu Ile Phe Cys
                165                 170                 175

Asp Ile Leu Glu Ala Ala Asn Lys Arg Gly Val Phe Val Cys Val Leu
            180                 185                 190

Leu Asp Gln Gly Gly Val Lys Leu Phe Gln Glu Met Cys Asp Lys Val
        195                 200                 205

Gln Ile Ser Asp Ser His Leu Lys Asn Ile Ser Ile Arg Ser Val Glu
    210                 215                 220

Gly Glu Ile Tyr Cys Ala Lys Ser Gly Arg Lys Phe Ala Gly Gln Ile
225                 230                 235                 240

Arg Glu Lys Phe Ile Ile Ser Asp Trp Arg Phe Val Leu Ser Gly Ser
                245                 250                 255

Tyr Ser Phe Thr Trp Leu Cys Gly His Val His Arg Asn Ile Leu Ser
            260                 265                 270

Lys Phe Thr Gly Gln Ala Val Glu Leu Phe Asp Glu Glu Phe Arg His
        275                 280                 285

Leu Tyr Ala Ser Ser Lys Pro Val Met Gly Leu Lys Ser Pro Arg Leu
    290                 295                 300

Val Ala Pro Val Pro Pro Gly Ala Ala Pro Ala Asn Gly Arg Leu Ser
305                 310                 315                 320

Ser Ser Ser Gly Ser Ala Ser Asp Arg Thr Ser Ser Asn Pro Phe Ser
                325                 330                 335

Gly Arg Ser Ala Gly Ser His Pro Gly Thr Arg Ser Val Ser Ala Ser
            340                 345                 350

Ser Gly Pro Cys Ser Pro Ala Ala Pro His Pro Pro Pro Pro Pro Arg
        355                 360                 365

Phe Gln Pro His Gln Gly Pro Trp Gly Ala Pro Ser Pro Gln Ala His
    370                 375                 380

Leu Ser Pro Arg Pro His Asp Gly Pro Ala Ala Val Tyr Ser Asn
385                 390                 395                 400

Leu Gly Ala Tyr Arg Pro Thr Arg Leu Gln Leu Glu Gln Leu Gly Leu
                405                 410                 415

Val Pro Arg Leu Thr Pro Thr Trp Arg Pro Phe Leu Gln Ala Ser Pro
            420                 425                 430

His Phe

<210> SEQ ID NO 3
<211> LENGTH: 19
<212> TYPE: DNA
<213> ORGANISM: Homo sapien

<400> SEQUENCE: 3
gcccuaccug aaggaaaaa                                                19

<210> SEQ ID NO 4
<211> LENGTH: 19
<212> TYPE: DNA
<213> ORGANISM: Homo sapien

<400> SEQUENCE: 4
ggagagauau acugugcca                                                19
```

<210> SEQ ID NO 5
<211> LENGTH: 19
<212> TYPE: DNA
<213> ORGANISM: Homo sapien

<400> SEQUENCE: 5
ggaaauucgc uggccaaau                                                19

<210> SEQ ID NO 6
<211> LENGTH: 14
<212> TYPE: PRT
<213> ORGANISM: Homo sapien

<400> SEQUENCE: 6

Asp Ser His Leu Lys Asn Ile Ser Ile Arg Ser Val Glu Gly
 1               5                  10

<210> SEQ ID NO 7
<211> LENGTH: 61
<212> TYPE: DNA
<213> ORGANISM: Homo sapien

<400> SEQUENCE: 7
gatccgtgtg aaggagaga tatacttcct gtcagatata tctctccttc cacactttt    60 g                                                                  61

<210> SEQ ID NO 8
<211> LENGTH: 61
<212> TYPE: DNA
<213> ORGANISM: Homo  sapien

<400> SEQUENCE: 8
aattcaaaaa gtgtggaagg agagatatat ctgacaggaa gtatatctct ccttccacac  60
g                                                                  61

<210> SEQ ID NO 9
<211> LENGTH: 26
<212> TYPE: DNA
<213> ORGANISM: Homo sapien

<400> SEQUENCE: 9
gaattcatga gccggtcaag gcgcct                                       26

<210> SEQ ID NO 10
<211> LENGTH: 29
<212> TYPE: DNA
<213> ORGANISM: Homo sapien

<400> SEQUENCE: 10
ctcgagtcag aagtgagggg aggcctgca                                    29

<210> SEQ ID NO 11
<211> LENGTH: 25
<212> TYPE: DNA
<213> ORGANISM: Homo sapien

<400> SEQUENCE: 11
aattcatgag ccggtcaagg cacct                                        25

<210> SEQ ID NO 12
<211> LENGTH: 56

```
<212> TYPE: DNA
<213> ORGANISM: Homo sapien

<400> SEQUENCE: 12
gaattctcga gctacttgtc gtcgtcgtcc ttgtagtcga agtgagggga ggcctg      56

<210> SEQ ID NO 13
<211> LENGTH: 26
<212> TYPE: DNA
<213> ORGANISM: Homo sapien

<400> SEQUENCE: 13
gaattcatga gccggtcaag gcgcct                                       26

<210> SEQ ID NO 14
<211> LENGTH: 21
<212> TYPE: DNA
<213> ORGANISM: Homo sapien

<400> SEQUENCE: 14
cgagcggccg ctgaaggggt t                                            21

<210> SEQ ID NO 15
<211> LENGTH: 24
<212> TYPE: DNA
<213> ORGANISM: Homo sapien

<400> SEQUENCE: 15
cccctggcca aggtcatcca tgac                                         24

<210> SEQ ID NO 16
<211> LENGTH: 26
<212> TYPE: DNA
<213> ORGANISM: Homo sapien

<400> SEQUENCE: 16
gaaacagttc gagtaaagga ccatac                                       26

<210> SEQ ID NO 17
<211> LENGTH: 20
<212> TYPE: DNA
<213> ORGANISM: Homo sapien

<400> SEQUENCE: 17
tggaccatcc tctagactgc                                              20

<210> SEQ ID NO 18
<211> LENGTH: 20
<212> TYPE: DNA
<213> ORGANISM: Homo sapien

<400> SEQUENCE: 18
tcagggttat tgtctcatga                                              20
```